(12) United States Patent
Sadhasivam et al.

(10) Patent No.: US 11,597,978 B2
(45) Date of Patent: Mar. 7, 2023

(54) PERSONALIZED PAIN MANAGEMENT AND ANESTHESIA: PREEMPTIVE RISK IDENTIFICATION AND THERAPEUTIC DECISION SUPPORT

(71) Applicant: CHILDREN'S HOSPITAL MEDICAL CENTER, Cincinnati, OH (US)

(72) Inventors: Senthilkumar Sadhasivam, Mason, OH (US); Vidya Chidambaran, Cincinnati, OH (US); John McAuliffe, Cincinnati, OH (US); Kejian Zhang, Cincinnati, OH (US); Jaroslaw Meller, Cincinnati, OH (US); Cynthia A. Prows, Cincinnati, OH (US); Tsuyoshi Fukuda, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 539 days.

(21) Appl. No.: 16/850,537

(22) Filed: Apr. 16, 2020

(65) Prior Publication Data
US 2020/0308648 A1 Oct. 1, 2020

Related U.S. Application Data

(63) Continuation of application No. 15/915,581, filed on Mar. 8, 2018, now Pat. No. 10,662,476, which is a continuation of application No. 14/361,946, filed as application No. PCT/US2012/067111 on Nov. 29, 2012, now Pat. No. 9,944,985.

(60) Provisional application No. 61/661,073, filed on Jun. 18, 2012, provisional application No. 61/565,400, filed on Nov. 30, 2011.

(51) Int. Cl.
| | |
|---|---|
| *C12Q 1/68* | (2018.01) |
| *C07H 21/04* | (2006.01) |
| *C12Q 1/6883* | (2018.01) |
| *C12Q 1/6806* | (2018.01) |

(52) U.S. Cl.
CPC ......... *C12Q 1/6883* (2013.01); *C12Q 1/6806* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,675,904 A | 6/1987 | Silverman |
| 5,148,483 A | 9/1992 | Silverman |
| 5,288,644 A | 2/1994 | Beavis et al. |
| 5,445,934 A | 8/1995 | Fodor et al. |
| 5,700,637 A | 12/1997 | Southern |
| 5,744,305 A | 4/1998 | Fodor et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,429,027 B1 | 8/2002 | Chee et al. |
| 6,733,977 B2 | 5/2004 | Besemer et al. |
| 6,858,394 B1 | 2/2005 | Chee et al. |
| 7,364,858 B2 | 4/2008 | Barany et al. |
| 7,754,428 B2 | 7/2010 | Lo et al. |
| 7,858,313 B2 | 12/2010 | Ikeda et al. |
| 9,691,411 B2 | 6/2017 | Scherer et al. |
| 9,944,985 B2 | 4/2018 | Sadhasivam et al. |
| 10,662,476 B2 | 5/2020 | Sadhasivam et al. |
| 10,878,939 B2 | 12/2020 | Sadhasivam |

(Continued)

FOREIGN PATENT DOCUMENTS

| | | |
|---|---|---|
| EP | 0619321 A1 | 10/1994 |
| EP | 0619321 B1 | 1/1999 |

(Continued)

OTHER PUBLICATIONS

Bedini, et al. (2008). "Transcriptional Activation of Human mu-opioid Receptor Gene by Insulin-like Growth Factor-I in Neuronal Cells is Modulated by the Transcription Factor REST." Journal of Neurochemistry 105(6):2166-2178.

(Continued)

*Primary Examiner* — Jeanine A Goldberg
(74) *Attorney, Agent, or Firm* — KDB Firm PLLC

(57) ABSTRACT

Methods and compositions disclosed herein generally relate to methods of improving clinical and economic outcomes to address adverse effects related to anesthesia, analgesics, opioids, and inadequate pain relief. Embodiments of the invention relate to the association between genes, specific polymorphisms of genes, and non-genetic factors with inadequate pain relief and anesthesia-, analgesic-, and/or opioid-related adverse effects. Embodiments of the invention can be used to determine and manage patient risk factors for development of adverse perioperative effects and can allow for personalized anesthesia and pain management for improvement of pain control and reduction of anesthesia-, analgesic-, and opioid-related adverse outcomes. These methods and compositions apply to non-surgical pain management with opioids. Therefore, patients who are genetically predisposed to risk of inadequate pain relief and/or serious side effects from anesthesia, analgesics, and/or opioids can be identified and individualized treatment plans developed for implementation by the clinician to improve clinical and economic outcomes.

7 Claims, 28 Drawing Sheets

(56) References Cited

U.S. PATENT DOCUMENTS

| | | |
|---|---|---|
| 2002/0077825 A1 | 6/2002 | Silverman et al. |
| 2002/0110823 A1 | 8/2002 | Hogan |
| 2003/0078768 A1 | 4/2003 | Silverman et al. |
| 2003/0092019 A1 | 5/2003 | Meyer et al. |
| 2003/0167189 A1 | 9/2003 | Lutgen et al. |
| 2007/0233468 A1 | 10/2007 | Ozdas et al. |
| 2007/0233498 A1 | 10/2007 | Silverman et al. |
| 2008/0201280 A1 | 8/2008 | Martin et al. |
| 2009/0253585 A1 | 10/2009 | Diatchenko et al. |
| 2010/0143929 A1 | 6/2010 | Levenson et al. |
| 2010/0240552 A1 | 9/2010 | Ikeda et al. |
| 2010/0262603 A1 | 10/2010 | Odom et al. |
| 2011/0257098 A1 | 10/2011 | Tuefferd et al. |
| 2012/0041911 A1 | 2/2012 | Pestian et al. |
| 2012/0283117 A1 | 11/2012 | Rothenberg |
| 2012/0288068 A1 | 11/2012 | Jaiswal et al. |
| 2013/0035961 A1 | 2/2013 | Yegnanarayanan |
| 2013/0310549 A1 | 11/2013 | Shuber |
| 2014/0371256 A1 | 12/2014 | Sadhasivam et al. |
| 2016/0180041 A1 | 6/2016 | Pestian et al. |
| 2017/0061073 A1 | 3/2017 | Sadhasivam |
| 2017/0233813 A1 | 8/2017 | Rothenberg et al. |
| 2018/0334717 A1 | 11/2018 | Sadhasivam et al. |
| 2019/0367988 A1 | 12/2019 | Chidambaran et al. |
| 2020/0318194 A1 | 10/2020 | Sadhasivam et al. |
| 2020/0340061 A1 | 10/2020 | Sadhasivam et al. |
| 2021/0205346 A1 | 9/2021 | Chidambaran et al. |

FOREIGN PATENT DOCUMENTS

| | | |
|---|---|---|
| EP | 2785874 B1 | 9/2018 |
| JP | 2012-070732 A | 4/2012 |
| WO | 89/10977 A1 | 11/1989 |
| WO | 03/054166 A2 | 7/2003 |
| WO | 2003/054166 A3 | 3/2004 |
| WO | 2005/095601 A1 | 10/2005 |
| WO | 2005/105093 A2 | 11/2005 |
| WO | 2005/105093 A3 | 9/2006 |
| WO | 2009/067473 A2 | 5/2009 |
| WO | 2010/126867 A1 | 11/2010 |
| WO | 2012/025765 A1 | 3/2012 |
| WO | 2012/177945 A2 | 12/2012 |
| WO | 2012/177945 A3 | 2/2013 |
| WO | 2013/082308 A1 | 6/2013 |
| WO | 2013/126834 A1 | 8/2013 |
| WO | 2013/155010 A1 | 10/2013 |
| WO | 2014/059178 A1 | 4/2014 |
| WO | 2014/190269 A1 | 11/2014 |
| WO | 2015/017731 A1 | 2/2015 |
| WO | 2015/127379 A1 | 8/2015 |
| WO | 2016/023026 A1 | 2/2016 |
| WO | 2018136728 A1 | 7/2018 |
| WO | 2020/006175 A1 | 1/2020 |

OTHER PUBLICATIONS

Chidambaran, et al. (2017). "DNA Methylation at the mu-l Opioid Receptor Gene (OPRM I) Promoter Predicts Preoperative, Acute, and Chronic Postsurgical Pain After Spine Fusion." Pharmacogenomics and Personalized Medicine 10:157-168.

Doehring, et al. (2013). "Chronic Opioid Use is Associated with Increased DNA Methylation Correlating with Increased Clinical Pain." Pain 154(1):15-23.

Knothe, et al. (2016). "Pharmacoepigenetics of the Role of DNA Methylation in µ-opioid Receptor Expression in Different Human Brain Regions." Epigenetics 8(12):1583-1599.

Sun, et al. (Nov. 4, 2015). "DNA Methylation Modulates Nociceptive Sensitization after Incision." PloS One 10(11):1-16.

Viet, et al. (Jun. 24, 2014). "Demethylating Drugs as Novel Analgesics for Cancer Pain." Clinical Cancer Research 20(18):4882-4893.

Viet, et al. (Sep. 2017). "OPRM1 Methylation Contributes to Opioid Tolerance in Cancer Patients." The Journal of Pain 18(9):1046-1059.

Zhou, et al. (2014). "Increased Methylation of the RIOR Gene Proximal Promoter in Primary Sensory Neurons Plays a Crucial Role in the Decreased Analgesic Effect of Opioids in Neuropathic Pain." Molecular Pain 10(1):51-64.

Extended European Search Report dated Oct. 28, 2020 for EP Application No. 18741087.3, filed Jan. 19, 2018 in the International Application No. PCT/US2018/014405. 9 pages.

Wu et al., "Treatment of acute postoperative pain". Lancet 2011; 377 : 2215-25.

Extended European Search Report issued in European Application No. 12854522.5, dated Jul. 21, 2015, 8 pages.

Extended European Search Report issued in European Application No. 18196397.6, dated May 8, 2019, 12 pages.

International Preliminary Report on Patentability received for PCT International Application No. PCT/US18/14405, dated Aug. 1, 2019, 10 pages.

International Preliminary Report on Patentability received for PCT International Application No. PCT/US2012/067111, dated Jun. 12, 2014, 7 pages.

International Preliminary Report on Patentability received for PCT International Application No. PCT/US2015/017134, dated Sep. 9, 2016, 9 pages.

International Search Report and Written Opinion received for PCT Patent International Application No. PCT/US18/14405, dated May 10, 2018, 15 pages.

International Search Report and Written Opinion received for PCT Patent International Application No. PCT/US19/39411, dated Oct. 24, 2019, 10 pages.

International Search Report received for PCT Patent International Application No. PCT/US2012/067111, dated Mar. 20, 2013, 9 pages.

International Search Report received for PCT Patent International Application No. PCT/US2014/039357, dated Sep. 24, 2014, 8 pages.

International Search Report received for PCT Patent International Application No. PCT/US2014/049301, dated Dec. 8, 2014, 8 pages.

International Search Report received for PCT Patent International Application No. PCT/US2015/017134, dated May 6, 2015, 11 pages.

Partial European Search Report issued in European Application No. 18196397.6, dated Feb. 2, 2019, 12 pages.

Extended European Search Report for EP Application No. 15828951.2, dated Nov. 16, 2017, 8 pages.

Anderson et al. (Sep. 2011) "Evaluation of a morphine maturation model for the prediction of morphine clearance in children", British Journal of Clinical Pharmacology, 72(3):518-520.

Anonymous (Apr. 24, 2018) "Illumina_top_bot_strand".

Barratt et al. (Apr. 18, 2012) "ABCB1 haplotype and OPRM1 118A>G genotype interaction in methadone maintenance treatment pharmacogenetics", 5(1):53-62.

Biesiada et al. (Nov. 2014) "Genetic risk signatures of opioid-induced respiratory depression following pediatric tonsillectomy", Pharmacogenomics, 15(14):1749-1762.

Branford et al. (Jul. 27, 2012) "Opioid Genetics: The Key to Personalized Pain Control?", Clinical Genetics, 82(4):301-310.

Buchheit et al. (Sep. 14, 2012) "Epigenetics and the Transition from Acute to Chronic Pain.", Pain Medicine, 13(11):1474-1490.

Campa et al. (Sep. 26, 2007) "Association of ABCB1/MDR1 and OPRM1 gene polymorphisms with morphine pain relief", Clinical Pharmacology & Therapeutics, 83(4):559-566.

Chang et al. (Apr. 8, 2010) "SNP-RFLPing 2: An Updated and Integrated PCR-RFLP Tool for SNP Genotyping", BMC Bioinformatics, 11(1):7 pages.

Chidambaran et al. (Mar. 2017) "ABCC3 Genetic Variants Are Associated With Postoperative Morphine-Induced Respiratorydepression and Morphine Pharmacokinetics in Children", Pharmacogenomics Journal, 17(2):162-169.

Choi et al. (Oct. 2010) "Association of ABCB1 polymorphisms with the efficacy of ondansetron for postoperative nausea and vomiting", Anaesthesia, 65(10):996-1000.

(56) References Cited

OTHER PUBLICATIONS

Chorbov et al. (2011) "Elevated Levels of DNA Methylation at the OPRM1 Promoter in Blood and Sperm from Male Opioid Addicts.", Journal of Opioid Management, 7(4):258-264.
Clavijo et al. (Mar. 12, 2011) "A sensitive assay for the quantification of morphine and its active metabolites in human plasma and dried blood spots using high-performance liquid chromatography-tandem mass spectrometry", Analytical and Bioanalytical Chemistry, 400(3):715-728.
Cohen et al. (Aug. 2012) "Pharmacogenetics in perioperative medicine", Current opinion in anaesthesiology, 25(4):419-427.
Collins et al. (Oct. 2005) "Online Selection of Discriminative Tracking Features", IEEE Transactions on Pattern Analysis and Machine Intelligence, 27(10):1631-1643.
Coulbault et al. (Apr. 1, 2006) "Environmental and genetic factors associated with morphine response in the postoperative period", Clinical Pharmacology & Therapeutics, 79(4):316-324.
Crews et al. (Jan. 29, 2014) "Clinical Pharmacogenetics Implementation Consortium Guidelines for Cytochrome P450 2d6 Genotype and Codeine Therapy", Clinical Pharmacology & Therapeutics, 95(4):376-382.
De Gregori et al. (Nov. 1, 2010) "Individualizing pain therapy with opioids: The rational approach based on pharmacogenetics and pharmacokinetics", European Journal of Pain Supplements, 4(4):245-250.
Dellon et al. (May 1, 2014) "Immunohistochemical Evidence of Inflammation Is Similar in Patients with Eosinophilic Esophagitis and PPI-Responsive Esophageal Eosinophilia: A Prospective Cohort Study", Gastroenterology, 146(5):S17.
Dellon et al. (Oct. 22, 2013) "Clinical and Endoscopic Characteristics Do Not Reliably Differentiate PPI-Responsive Esophageal Eosinophilia and Eosinophilic Esophagitis in Patients Undergoing Upper Endoscopy: A Prospective Cohort Study", The American Journal of Gastroenterology, 108(12):1854-1860.
Eissing et al. (Feb. 1, 2012) "Pharmacogenomics of Codeine, Morphine, and Morphine-6-Glucuronide: Model-Based Analysis of the Influence of CYP2D6 Activity, UGT2B7 Activity, Renal Impairment, and CYP3A4 Inhibition", Molecular Diagnosis & Therapy, 16(1):43-53.
Fukada et al. (Jul. 2013) "OCT1 Genetic Variants Influence the Pharmacokinetics of Morphine in Children", Pharmacogenomics, 14(10):1141-1151.
Fukada et al. (Feb. 2013) "Oral Session II-A (OII-A) Special Populations 3:45 pm-4:45 pm", Clinical Pharmacology & Therapeutics, 93:S49-S51.
Gasche et al. (Dec. 30, 2004) "Codeine Intoxication Associated with Ultrarapid CYP2D6 Metabolism", The New England Journal of Medicine, 351(27):2827-2831.
Gong et al. (May 30, 2013) "Gene polymorphisms of OPRM1 A118G and ABCB1 C3435T may influence opioid requirements in Chinese patients with cancer pain", Asian Pacific Journal of Cancer Prevention, 14(5):2937-2943.
Guyon et al. (Jan. 2002) "Gene Selection for Cancer Classification using Support Vector Machines", Machine Learning, 46:389-422.
Hacker et al. (1997) "Lack of association between an interleukin-1 receptor antagonist gene polymorphism and ulcerative colitis", Gut, 40:623-627.
Himes et al. (Mar. 4, 2009) "Prediction of Chronic Obstructive Pulmonary Disease (COPD) in Asthma Patients Using Electronic Medical Records", Journal of the American Medical Informatics Association, 16(3):371-379.
Hirschhorn et al. (Mar. 2002) "A comprehensive review of genetic association studies", Genetics in Medicine, 4(2):45-61.
Ioannidis et al. (Oct. 15, 2001) "Replication Validity of Genetic Association Studies", Nature Genetics, 15:306-309.
Jannetto et al. (May 18, 2011) "Pain management in the 21st century: Utilization of Pharmacogenomics and Therapeutic Drug Monitoring", Expert Opinion on Drug Metabolism & Toxicology, 7(6):745-752.

Juffali et al. (2010) "The WiNAM project: Neural data analysis with applications to epilepsy", Biomedical Circuits and Systems Conference, 45-48.
Kelly et al. (Apr. 9, 2012) "More Codeine Fatalities After Tonsillectomy in North American Children", Pediatrics, 129(5):e1343-1347.
Kim et al. (2006) "Genetic Predictors for Acute Experimental Cold and Heat Pain Sensitivity in Humans", Journal of Medical Genetics, e40, 43(8):8 pages.
Kleine-Brueggeney et al. (Dec. 15, 2010) "Pharmacogenetics in palliative care", Forensic science international, 203(1-3):63-70.
Larkin et al. (2010) "A Candidate Gene Study of Obstructive Sleep Apnea in European Americans and African Americans", American Journal of Respiratory and Critical Care Medicine, 182:947-953.
Laugsand et al. (Apr. 11, 2011) "Clinical and genetic factors associated with nausea and vomiting in cancer patients receiving opioids", European Journal of Cancer, 47(11):1682-1691.
Leschziner et al. (Sep. 12, 2006) "ABCB1 Genotype and PGP Expression, Function and Therapeutic Drug Response: A Critical Review and Recommendations for Future Research", The Pharmacogenomics Journal, 7(3):154-179.
GABA Receptor, Wikipedia 12 pages, Nov. 25, 2021.
Partial European Search Report dated Feb. 28, 2022 from International Patent Application No. 19826435.0, dated Feb. 28, 2022; 4 pages.
Lirk, et al. Epigenetics in the Perioperative Period, British Journal of Pharmacology 172(11):2748-55, Jun. 2015.
Mauck, et al. Epigenetics of Chronic Pain after Thoracic Surgery, Current Opinion in Anaesthesiology 27(1):1-5., Feb. 2014.
Stephens, et al. Associations Between Genetic and Epigenetic Variations in Cytokine Genes and Mild Persistent Breast Pain in Women Following Breast Cancer Surgery, Cytokine 99:203-213, Nov. 2017.
Si et al., Correlations Between Inflammatory Cytokines, Muscle Damage Markers and Acute Postoperative Pain Following Primary Total Knee Arthroplasty, BMC Musculoskeletal Disorders, 18(1):265, Jun. 17, 2017.
Kesimci et al. "Association between ABCB1 gene polymorphisms and fentanyl's adverse effects in Turkish patients undergoing spinal anesthesia" Gene 493 (2012) 273-277.
Berde et al. "Comparison of morphone and methadone for prevention of postoperative pain in 3-7 year old children" Journal of Pediatrics, vol. 119, No. 1, Part 1, 1991.
Coller et al., "ABCB1 genetic variability and methadone dosage requirements in opioid-dependent individuals" Clininical Pharmacology and Therapeutics, 2006; 80(6):682-90.
International Preliminary Report received for PCT International Application No. PCT/US2019/039411, dated Jan. 7, 2021, 7 pages.
Lucentini (Dec. 20, 2004) "Gene Association Studies Typically Wrong", The Scientist, 18(24):20.
Meineke et al. (Dec. 2002) "Pharmacokinetic modelling of morphine, morphine-3-glucuronide and morphine-6-glucuronide in plasma and cerebrospinal fluid of neurosurgical patients after short-term infusion of morphine", British Journal of Clinical Pharmacology, 54(6):592-603.
Mizuno et al. (2013) "Genotype of Abcc3-211c > T Influences the Pharmacokinetics of Morphine Glucuronide in Children", Clinical Pharmacology & Therapeutics, 93:S63.
Mogil et al. (Jul. 6, 1999) "The genetic mediation of individual differences in sensitivity to pain and its inhibition", PNAS, 96(14):7744-7751.
Muller et al. (Jan. 1, 2010) "Mutation Screen and Association Studies for the Fatty Acid Amide Hydrolase (Faah) Gene and Early Onset and Adult Obesity", BMC Medical Genetics, 11:2, 9 Pages.
Nies et al. (2009) "Expression of organic cation transporters OCT1 (SLC22A 1) and OCT3 (SLC22A3) is affected by genetic factors and cholestasis in human liver", Hepatology, 50(4):1227-1240.
Ozdas et al. (Sep. 2004) "Investigation of Vocal Jitter and Glottal Flow Spectrum as Possible Cues for Depression and Near-Term Suicidal Risk", Transactions on Biomedical Engineering, 51(9):1530-1540.

(56) References Cited

OTHER PUBLICATIONS

Park et al. (Dec. 27, 2006) "Genetic polymorphisms in the ABCB1 gene and the effects of fentanyl in Koreans", Clinical Pharmacology & Therapeutics, 81(4):539-546.

Pattinson (May 1, 2008) "Opioids and the control of respiration", British Journal of Anaesthesia, 100(6):747-758.

International Search Report dated Nov. 9, 2015 for International Application No. PCT/US2015/044461, 11 pages.

Pennisi (Sep. 18, 1998) "A Closer Look at SNPs Suggests Difficulties", Science, 281(5384):1787-1789.

Prows et al. (Nov. 13, 2013) "Codeine-related adverse drug reactions in children following tonsillectomy: A prospective study", Laryngoscope, 124(5):1242-1250.

Ray et al. (May 16, 2011) "Human Mu Opioid Receptor (OPRM1 A 118G) polymorphism is associated with brain mu-opioid receptor binding potential in smokers", PNAS, 108(22):9268-9273.

Ross et al. (Mar. 2008) "Genetic variation and response to morphine in cancer patients—Catechol-0-methyltransferase and multidrug resistance-1 gene polymorphisms are associated with central side effects", Cancer, 112(6):1390-1403.

Sadhasivam et al. (2014) "Genetics of pain perception, COMT and postoperative pain management in children", The Pharmacogenomics Journal, 15(3):277-284.

Sadhasivam et al. (Jul.-Aug. 2012) "Morphine clearance in children: does race or genetics matter?", Journal of Opioid Management, 8(4):217-226.

Sadhasivam et al. (2015) "Novel Associations between FAAH Genetic Varients an Postoperative Central Opioid Related Adverse Effects", The Pharmacogenomics Journal, 15(5):436-442.

Sadhasivam et al. (Apr. 1, 2010) "Pharmacogenetics and personalizing perioperative analgesia in children", Journal of Pain, 11(4):01 page.

Sadhasivam et al. (Jun. 13, 2012) "Preventing Opioid-Related Deaths in Children Undergoing Surgery", Pain Medicine, 13(7):982-983.

Sadhasivam et al. (Apr. 23, 2012) "Race and unequal burden of perioperative pain and opioid related adverse effects in children", Pediatrics, 129(5):832-838.

Scherer et al. (2013) "Investigating the Speech Characteristics of Suicidal Adolescents", International Conference on Acoustics, Speech and Signal Processing, 5 pages.

Shi et al. (Sep. 15, 2010) "Biological pathways and genetic variables involved in pain", Quality of Life Research, 19(10):1407-14717.

Shrestha et al. (Feb. 10, 2016) "Epigenetic Regulations of GABAergic Neurotransmission: Relevance for Neurological Disorders and Epigenetic Therapy", Medical Epigenetics, 4(1):1-19.

Shu et al. (2007) "Effect of Genetic Variation in the Organic Cation Transporter 1 (OCT1) on Metformin Action", Journal of Clinical Investigation, 117(5):1422-1431.

Sloan et al. (May 10, 2012) "Genetic Variations and Patient-Reported Quality of Life Among Patients With Lung Cancer", Journal of Clinical Oncology, 30(14):1699-1704.

SNPDEV (May 2, 2018) "Reference SNP (refSNP) Cluster Report: r5967935", https://www.ncbi.nlm.nih.gov/snp/rs967935.

Stamer et al. (Jun. 1, 2010) "Personalized therapy in pain management: Where do we stand?", Pharmacogenomics, 11(6):843-864.

Stamer et al. (Sep. 2008) "Respiratory Depression with Tramadol in a Patient with Renal Impairment and CYP2D6 Gene Duplication", International Anesthesia Research Society, 107(3):926-929.

Tzvetkov et al. (Jul. 5, 2013) "Morphine is a substrate of the organic cation transporter OCT1 and polymorphisms in OCT1 gene affect morphine pharmacokinetics after codeine administration", Biochemical Pharmacology, 86(5):666-678.

Venek et al. (2014) "Adolescent Suicidal Risk Assessment in Clinician-Patient Interaction: A Study of Verbal and Acoustic Behaviors", Spoken Language Technology Workshop, 6 pages.

Venkatasubramanian et al. (Jul. 2014) "ABCC3 and OCT1 genotypes influence pharmacokinetics of morphine in children", Pharmacogenomics, 15(10):1297-1309.

Verspoor et al. (Jun. 15, 2009) "The textual characteristics of traditional and Open Access scientific journals are similar", BMC Bioinformatics, 10:183.

Wen et al. (Aug. 23, 2013) "Molecular diagnosis of eosinophilic esophagitis by gene expression profiling", Gastroenterology, 145(6):1289-1299.

Wen et al. (Oct. 19, 2014) "Transcriptome analysis of proton pump inhibitor-responsive esophageal eosinophilia reveals proton pump inhibitor-reversible allergic inflammation", Journal of Allergy and Clinical Immunology, 135(1):187-197.

Zheng et al. (Jul. 26, 2006) "Extracting Principal Diagnosis, Co-Morbidity and Smoking Status for Asthma Research: Evaluation of a Natural Language Processing System", BMC Medical Informatics and Decision Making, 6:30.

Zwisler et al. (Aug. 2010) "The antinociceptive effect and adverse drug reactions of oxycodone in human experimental pain in relation to genetic variations in the OPRM1 and ABCB1 genes", Fundamental & Clinical Pharmacology, 24(4):517-524.

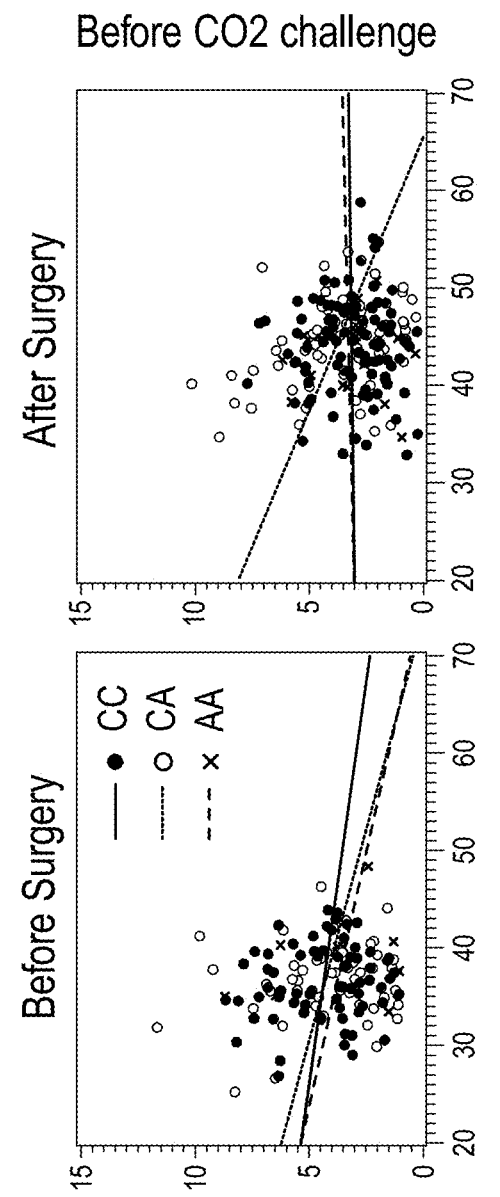

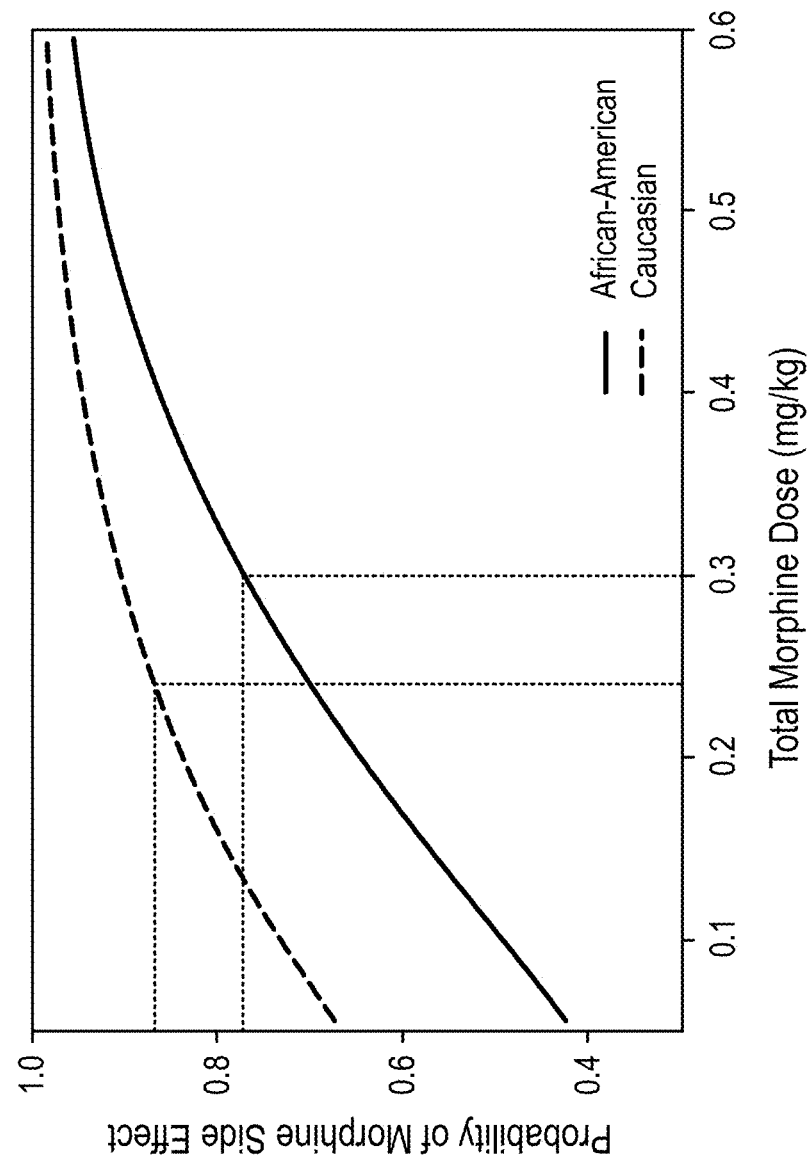

FIG. 18
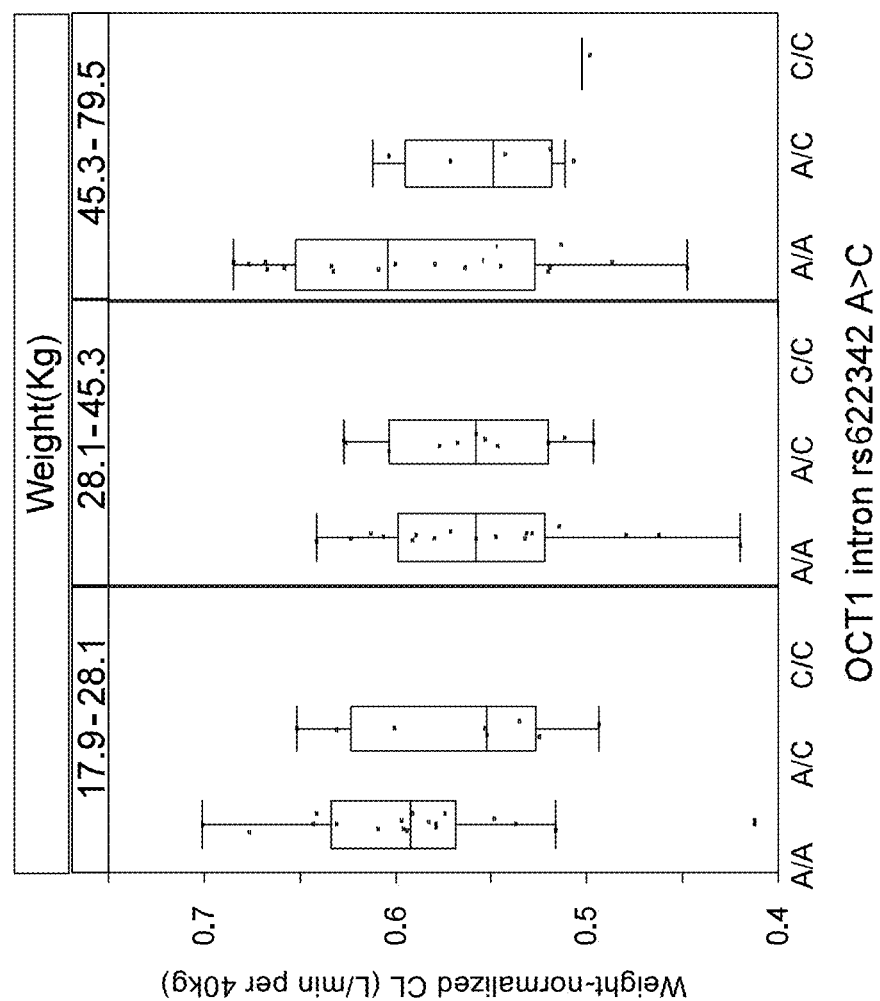
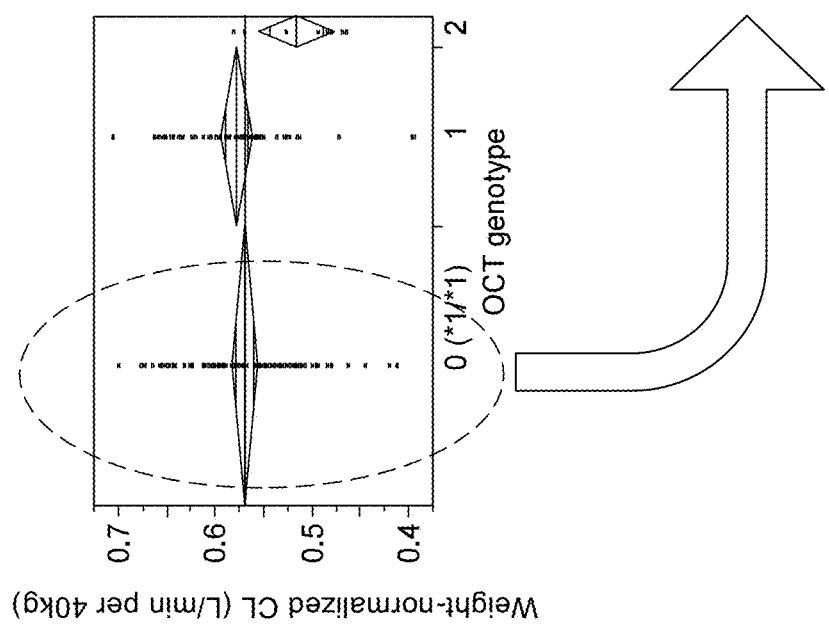

PERSONALIZED PAIN MANAGEMENT AND ANESTHESIA: PREEMPTIVE RISK IDENTIFICATION AND THERAPEUTIC DECISION SUPPORT

CROSS-REFERENCE TO RELATED APPLICATIONS

The present application is a continuation of U.S. patent application Ser. No. 15/915,581, filed on Aug. 9, 2018, which is a continuation of U.S. patent application Ser. No. 14/361,946, filed on May 30, 2014, now U.S. Pat. No. 9,944,985, which is a U.S. National Stage entry under 35 U.S.C. § 371 of International Application No. PCT/US2012/067111, filed on Nov. 29, 2012, designating the United States of America and published in English on Jun. 6, 2013, which in turns claims turn the benefit of priority under 35 U.S.C. § 119(e) to U.S. Provisional Application No. 61/565,400, METHODS AND COMPOSITIONS FOR CONDUCTING GENETIC PROFILING AND PERSONALIZATION OF SURGICAL ANALGESIA, filed on Nov. 30, 2011, and U.S. Provisional Application No. 61/661,073, PERSONALIZING PERIOPERATIVE OPIOID ANALGESIA-PREDICTIVE MODELS AND DECISION ALGORITHMS, filed on Jun. 18, 2012, which are incorporated by reference in their entirety.

STATEMENT REGARDING FEDERALLY-SPONSORED RESEARCH

This invention was made with government support awarded under RR026314, awarded by the National Institutes of Health. The government has certain rights in the invention.

FIELD OF THE INVENTION

The invention disclosed herein generally relates to methods and compositions comprising genetic markers for modulating surgical pain, anesthesia, post-surgical pain relief, and opioid-related adverse effects in a patient.

BACKGROUND

Safe and effective analgesia is an important medical and economic problem (Caldas, J. et al., *Paediatr. Anaesth.*, 14:910-5 (2004); Duedahl, T. and Hansen, E., *Paediatr. Anaesth.*, 17:756-74 (2007)). Approximately 28 million anesthetized surgical procedures are performed each year in the United States, many patients of which experience serious side-effects related to anesthesia, pain medications, and inadequate surgical pain relief. A significant fraction of the approximately 5 million children who undergo a painful surgery in the US each year experience inadequate pain relief and serious opioid-related side-effects (Cepeda, M., et al., *Clin. Pharmacol. Ther.*, 74:102-12 (2003); Sadhasivam S., et al., *Pediatrics*, 129:832-8 (2012); Esclamado, R., et al., *The Laryngoscope*, 99:1125-9 (1989)). Safe and effective analgesia is an important unmet medical need, and its continued existence is an important clinical and perioperative safety and economic problem.

Adverse effects are observed throughout all classes of anesthetic treatments due to the narrow therapeutic indices of anesthetic and opioid pain medications. Moreover, a high degree of inter-individual variability in drug response underscores the challenges inherent to anesthetic treatment. Morphine, the most commonly used perioperative opioid, has a narrow therapeutic index and large inter-patient variations in analgesic response and serious side effects. Frequent inter-individual variations in responses to morphine have significant clinical and economic impact, with inadequate pain relief at one end of the spectrum of responses and serious adverse effects such as respiratory depression at the other end.

This inter-individual variability to drug response is presumed to be the result of a complex interaction of multiple factors. However, this complexity has stymied efforts to elucidate how genetic variability affects surgical pain and adverse responses to opioids. Accordingly, efforts to predict patient response to anesthesia can have a great impact in enabling clinicians to personalize analgesia to maximize pain relief while minimizing its adverse effects.

SUMMARY OF THE INVENTION

Embodiments of the invention encompass methods of determining a risk or a susceptibility to developing one or more adverse effects from administered anesthesia, analgesic, and/or opioid in a subject, the method including: obtaining a nucleic acid sample from a subject; analyzing the sample for presence or absence of at least one allele of at least one polymorphism associated with pain perception, persistent postoperative/chronic pain, and/or one or more anesthetic-, analgesic-, and/or opioid-related adverse effects; evaluating the subject for presence or absence of at least one non-genetic risk factor for suffering one or more adverse effects from administered anesthesia, analgesic, and/or opioid; determining the subject's risk or susceptibility to developing one or more adverse effects from administered anesthesia, analgesic, and/or opioid, wherein the presence of at least one non-genetic risk factor and/or the presence of absence of the at least one allele of the at least one polymorphism indicates that the patient has an elevated risk for suffering an one or more adverse anesthesia-, analgesic-, and/or opioid-related effects.

In some embodiments of the methods, the at least one non-genetic risk factor can be, for example, race, sex, age, weight, body mass index (BMI), or obstructive sleep apnea disease status. In some embodiments, the at least one non-genetic risk factor can be, for example, sleep disordered breathing, allergy status, sensitivity, a medical condition that affects an administrative route for delivered anesthetic, analgesic, and/or opioid, ethnicity, medical history, a drug interaction, psychological anxiety, stress level, or lifestyle.

In some embodiments of the methods, the at least one polymorphism associated with pain perception, persistent postoperative/chronic pain and/or one or more anesthetic adverse effects can be, for example, ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKKI rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, V158M rs4680, the CYP2D6*2, *2A, *3, *4, *5, *6, *7, *8, *9, *10, *11, *14, *15, *17, *18, *19, *20, *35, *40, *41, *42, and *44 alleles, the PGRN-Seq genetic markers (Table 16), or markers in linkage disequilibrium therewith having $r^2$ value of at least 0.1 and/or |D'| value of at least 0.2.

In some embodiments, the sample can be analyzed for presence or absence of at least two polymorphisms associated with pain perception, persistent postoperative/chronic pain, and/or one or more anesthetic-, analgesic-, and/or opioid-related adverse effects. In some embodiments, the sample can be analyzed for the presence or absence of at least three polymorphisms associated with pain perception, persistent postoperative/chronic pain, and/or one or more anesthetic adverse effects. In some embodiments, the sample can be analyzed for the presence or absence of at least four polymorphisms associated with pain perception, persistent postoperative/chronic pain, and/or one or more anesthetic adverse effects.

In some embodiments, the subject can be a pediatric patient. In some embodiments, the subject can be at risk of inadequate pain relief and/or one or more serious side effects from administered anesthesia, analgesic, and/or opioids.

Embodiments of the invention also encompass compositions for identifying a patient at risk for suffering one or more adverse effects from administered anesthesia, analgesic, and/or opioid, including at least one polymorphism associated with pain perception, persistent postoperative/chronic pain, and/or one or more anesthetic-, analgesic-, and/or opioid-related adverse effects.

In some embodiments, the composition includes a gene chip. In some embodiments, the gene chip includes a low density array. In some embodiments, the composition includes a surface with a DNA array.

Embodiments of the invention also encompass methods of determining a risk or a susceptibility to developing obstructive sleep apnea (OSA) and/or a risk of OSA patients having increased pain and/or increased anesthetic-, analgesic-, and/or opioid-related adverse effects, the method including: obtaining a nucleic acid sample from a subject; analyzing the sample for the presence or absence of at least one allele of at least one polymorphism associated with pain perception and/or anesthetic-, analgesic-, and/or opioid-related adverse effects; evaluating the subject for the presence or absence of at least one non-genetic risk factor for suffering adverse effects from administered anesthesia, analgesic, and/or opioid; determining the subject's risk of suffering adverse effects from administered anesthesia, analgesic, and/or opioid, wherein the presence of at least one non-genetic risk factor and/or the presence of absence of the at least one allele of the at least one polymorphism indicates that the patient has an elevated risk for susceptibility to developing OSA and/or a risk of OSA patients having increased pain and/or increased anesthetic-, analgesic-, and/ or opioid-related adverse effects.

Embodiments of the invention also encompass methods of carrying out personalized treatment to maximize pain relief while minimizing adverse effects in a subject, the method including: identifying a subject in need of pain relief; obtaining a nucleic acid sample from the subject; analyzing the sample for the presence or absence of at least one allele of at least one polymorphism associated with pain perception, persistent postoperative/chronic pain, and/or anesthetic-, analgesic-, and/or opioid-related adverse effects; evaluating the subject for the presence or absence of at least one non-genetic risk factor for suffering adverse effects from administered anesthesia, analgesic, and/or opioid; determining the subject's risk of suffering adverse effects from administered anesthesia, analgesic, or opioid, wherein the presence of at least one non-genetic risk factor and/or the presence of absence of the at least one allele of the at least one polymorphism indicates that the patient has an elevated risk for suffering an adverse anesthesia-, analgesic-, and/or opioid-related effect; selecting one or more preferred therapeutics and/or alternatives and preferred dosage ranges based upon the determination; avoiding high-risk therapeutics based upon the determination; administering to the subject the one or more preferred therapeutics in the preferred dosage ranges, wherein administration of the one or more preferred therapeutics results in personalized treatment by maximizing pain relief while minimizing adverse effects.

In some embodiments, the therapeutic can be an analgesic, anesthetic, and/or opioid. In some embodiments, the analgesic, anesthetic, and/or opioid can be, for example, morphine or codeine. In some embodiments, the analgesic, anesthetic, and/or opioid can be, for example, benzocaine, chloroprocaine, cocaine, cyclomethycaine, dimethocaine/ loracaine, piperocaine, propoxycaine, procaine/novocaine, proparacaine, tetracaine/amethocaine, articaine, bupivacaine, cinchocaine/dibucaine, etidocaine, levobupivacaine, lidocaine/lignocaine, mepivacaine, prilocaine, ropivacaine, trimecaine, saxitoxin, tetrodotoxin, menthol, eugenol, desflurane, enflurane, halothane, isoflurane, methoxyflurane, nitrous oxide, sevoflurane, xenon, amobarbital, methohexital, thiamylal, thiopental, diazepam, lorazepam, midazolam, etomidate, ketamine, propofol, alfentanil, fentanyl, remifentanil, sufentanil, buprenorphine, butorphanol, diamorphine, hydromorphone, levorphanol, meperidine, methadone, nalbuphine, oxycodone, hydrocodone, tramadol, ondansetron, dexamethasone, oxymorphone, pentazocine, succinylcholine, decamethonium, mivacurium, rapacuronium, atracurium, cisatracurium, rocuronium, vecuronium, alcuronium, doxacurium, gallamine, metocurine, pancuronium, pipecuronium, tubocurarine, morphine, fentanyl, hydromorphone, oxycodone, methadone, alfentanil, remifentanil, acetaminophen, NSAIDs, dexmedetomidine, clonidine, or combinations and derivatives thereof.

In some embodiments of the methods, the personalized treatment to maximize pain relief while minimizing adverse effects can be developed preemptively, prior to and/or during procedures and/or clinical care that involve administration of anesthetic, analgesic, and/or opioid. In some embodiments, the personalized treatment to maximize pain relief while minimizing adverse effects can be carried out postoperatively and in non-surgical pain management clinical settings.

BRIEF DESCRIPTION OF THE DRAWINGS

Those of skill in the art will understand that the drawings, described below, are for illustrative purposes only. The drawings are not intended to limit the scope of the present teachings in any way.

FIG. 5A, before morphine administration; FIG. 5B, after morphine administration; FIG. 5C, resting minute ventilation, before and after surgery; and FIG. 5D, after $CO_2$ challenge, before and after surgery.

FIGS. 7A-7D depict genetic variations of FAAH and hypercapnic ventilatory response in children and demonstrates that postoperative minute ventilation and ventilatory response to carbon dioxide were significantly lower compared to preoperative baseline values. Minute ventilation reduction differed between FAAH genotypes (p=0.007). FIG. 7A, before surgery and before $CO_2$ challenge; FIG. 7B after surgery but before $CO_2$ challenge; FIG. 7C before surgery but after $CO_2$ challenge; and FIG. 7D after surgery and after $CO_2$ challenge.

FIG. 8 depicts a plot illustrating the racial differences and predicted probabilities of postoperative morphine-induced adverse effects in children.

FIG. 9A depicts the significant increase in PONV with increasing perioperative doses of morphine among Caucasian girls compared to Caucasian boys (p=0.0005); Caucasian boys were resistant to PONV and paradoxically had lower probability of PONV with increasing morphine doses. FIG. 9B depicts the significant increase in prolonged PACU stays due to opioid-related adverse effects among Caucasian girls compared to Caucasian boys (p=0.0113).

FIG. 18 depicts the contribution of the rs622342 single nucleotide polymorphism (SNP) to the weight-normalized morphine clearance of OCT1 genotypes.

FIG. 27A, pain score=30; FIG. 27B, pain score=60. POD, postoperative days.

DETAILED DESCRIPTION OF THE INVENTION

Definitions

Figure 1:
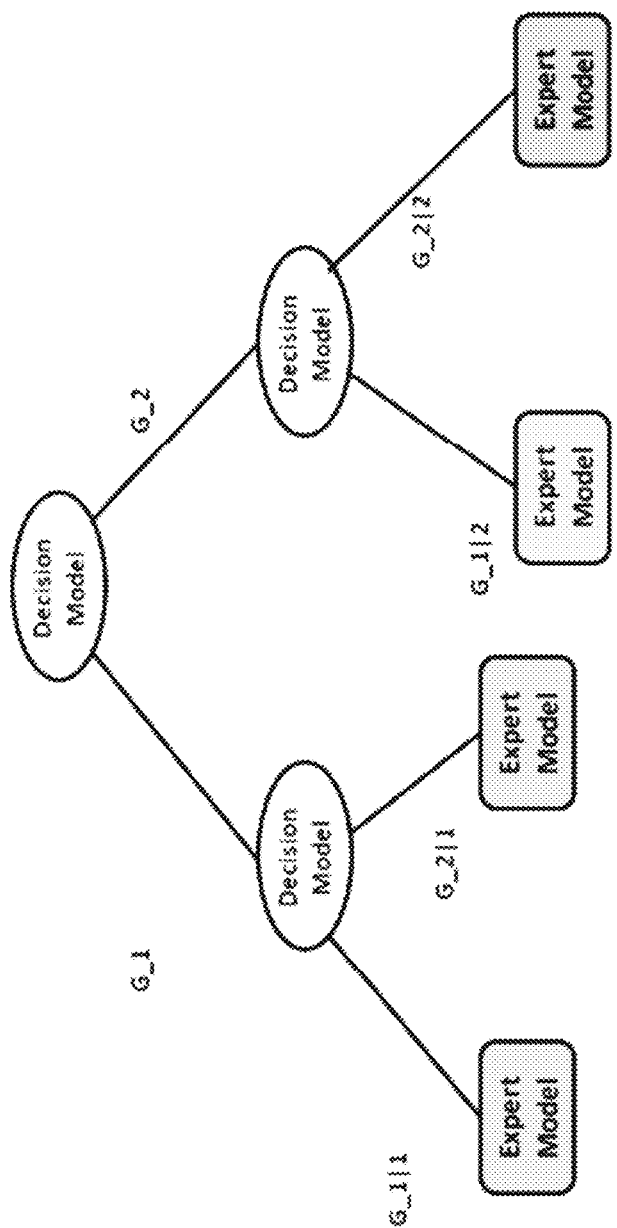
FIG. 1 depicts an exemplary hierarchical mixtures of experts (HME) decision tree, wherein the terminal nodes are called "experts" (or expert networks) that provide individual (and context dependent) prediction of the response.

Unless otherwise noted, terms are to be understood according to conventional usage by those of ordinary skill in the relevant art.

A "single nucleotide polymorphism," or "SNP," is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI) or identifies the residue change associated with the identified polymorphism. SNP genotyping arrays have become an important tool for cohort identification and stratification, phenotype-genotype association studies, discovery of disease markers, prediction of molecular phenotypes, and clinical decision support.

As used herein, the term "variant" refers to a segment of DNA that differs from the reference DNA.

As used herein, the term "marker" or a "polymorphic marker" refers to a variant. Alleles that differ from the reference are referred to as "variant" alleles.

A "microsatellite" is a polymorphic marker that has multiple small repeats of bases that are typically 2-8 nucleotides in length (such as CA repeats) at a particular site, in which the number of repeat lengths varies in the general population. An "indel" is a common form of polymorphism comprising a small insertion or deletion that is typically only a few nucleotides long.

As used herein, the term "haplotype" refers to a segment of genomic DNA that is characterized by a specific combination of a series of polymorphic markers arranged along the segment. For diploid organisms such as humans, a haplotype comprises one member of the pair of alleles for each polymorphic marker or locus along the segment. In some embodiments, the haplotype can comprise an allele for each of two or more markers, three or more markers, four or more markers, or five or more markers. As used herein, the term "susceptibility" refers to the proneness of an individual towards the development of a certain state (e.g. a certain trait, phenotype, or disease), or towards being less able to resist a particular state than the average individual. The term encompasses both increased susceptibility and decreased susceptibility. Thus, particular alleles at polymorphic markers and/or haplotypes of the invention as described herein can be characteristic of increased susceptibility (i.e. increased risk) of adverse anesthetic effects, as characterized by a relative risk (RR) or odds ratio (OR) of greater than one for the particular allele or haplotype. Alternatively, some markers and/or haplotypes of the invention can be characteristic of decreased susceptibility (i.e. decreased risk) of adverse anesthetic effects, as characterized by a relative risk of less than one.

As used herein, the term "and/or" shall in the present context be understood to indicate that either or both of the items connected by it are involved. In other words, the term herein shall be taken to mean "one or the other or both."

As used herein, the term "look-up table" is a table that correlates one form of data to another form, or one or more forms of data to a predicted outcome to which the data is relevant, such as a phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or they can contain information about multiple markers; they can also comprise other factors, such as particulars about diseases diagnoses, racial information, biomarkers, biochemical measurements, therapeutic methods, or drugs, etc.

A "nucleic acid sample" as described herein, refers to a sample obtained from an individual that contains nucleic acid (DNA or RNA). In certain embodiments, such as, for example, the detection of specific polymorphic markers and/or haplotypes, the nucleic acid sample comprises genomic DNA. Such a nucleic acid sample can be obtained from any source that contains genomic DNA, including a blood sample, sample of amniotic fluid, sample of cerebrospinal fluid, or tissue sample from skin, muscle, buccal or conjunctival mucosa, placenta, gastrointestinal tract, or other organs.

As used herein, the term "decision tree" refers to a standard machine learning technique for multivariate data analysis and classification (Hastie, T., et al. *The Elements of Statistical Learning*, Second Edition, Springer (2009); Witten, I. and Frank, E. *Data Mining: Practical Machine Learning Tools and Techniques*, Second Edition, Morgan Kaufmann, San Francisco (2005); Hothorn, T. *Journal of Computational and Graphical Statistics*, 15:651-74 (2010)). Decision trees can be used to derive easily interpretable and intuitive rules for decision support systems.

"Therapeutic" and "therapeutics" as used herein refers primarily to one or more anesthetic, analgesic, and/or opioid compositions having an actual or potential beneficial effect for a patient. In some embodiments, the term can also include accompanying modes of treatment and/or administration and/or co-administration with other compositions and/or treatments, as recognized by those of skill in the art of anesthesia and analgesia.

"Alternative" and "alternatives" as used herein refers to one or more compositions and/or treatment and/or administration and/or co-administration that is generally considered by those of skill in the art to be an alternative to a given therapeutic.

A "high risk therapeutic" as used herein refers to a therapeutic and/or alternative that, in comparison to other therapeutics and/or alternatives, implicates an elevated risk of adverse effects, side effects, and/or other negative risks or eventualities.

Inter-individual variability to drug response is a significant clinical and perioperative safety and economic problem. Embodiments of the invention described herein include methods and compositions for carrying out personalized analgesia treatment to maximize pain relief while minimizing its adverse effects for patients.

Approximately 50% of the inter-individual variability in clinical response to morphine can be explained by SNPs in the genes involved in pain mechanisms and opioid metabolism, transport, and receptor signaling. Though previous research has identified individual genes contributing to the pain processing pathway by looking at single genotype-phenotype associations, no work has heretofore investigated how the interplay of multiple genes, gene-gene interactions, and non-genetic factors, including demographic, phenotypic and other data, affect analgesic response, nor has any research demonstrated the ability to predict a patient's level of pain upon treatment, or to facilitate both basic and translational clinical research using such information.

Embodiments of the invention are directed to the identification and management of risk factors of adverse postoperative outcomes, and personalized anesthesia, opioid administration, and pain management for improvement of pain control, analgesia, and reduction of anesthesia- and opioid-related adverse outcomes. This can include examining the influence of specific polymorphisms of genes involved in pain perception, opioid transport, and liver drug metabolism, amongst others, on postoperative pain and the analgesia and adverse effects of opioids and anesthesia. Steps and benchmarks can include: 1. Identifying patients who are genetically predisposed to risk of inadequate pain relief and/or serious side effects from anesthesia and opioids including morphine. 2. Exploring the effects of race and associated genetic profile on postoperative pain control and adverse effects with morphine and other opioids in patients. 3. Developing and validating a predictive and personalized clinical decision model to improve clinical, perioperative, and economic outcomes.

Embodiments of the invention are also directed to methods of identifying a patient at risk for suffering adverse effects from administered anesthesia, analgesic, or opioid, comprising obtaining a sample from the patient and analyzing the sample for the presence or absence of at least one polymorphism associated with pain perception, persistent postoperative/chronic pain, and/or anesthetic adverse effects, wherein the presence of absence of the at least one polymorphism indicates that the patient has an elevated risk for suffering an adverse opioid- and/or anesthesia-related effect.

Embodiments of the invention are also directed to methods of identifying a patient at risk for suffering from obstructive sleep apnea (OSA), comprising obtaining a sample from the patient and analyzing the sample for the presence or absence of at least one polymorphism associated with pain perception, persistent postoperative/chronic pain, and/or anesthetic adverse effects and/or OSA, wherein the presence of absence of the at least one polymorphism indicates that the patient has an elevated risk for suffering from OSA.

In some embodiments, the sample is analyzed for the presence or absence of at least two polymorphisms associated with pain perception, persistent postoperative/chronic pain, and/or anesthetic-, analgesic-, and/or opioid-related adverse effects. In some embodiments, the sample is analyzed for the presence or absence of at least three polymorphisms associated with pain perception, persistent postoperative/chronic pain, and/or anesthetic-, analgesic-, and/or opioid-related adverse effects. In some embodiments, the sample is analyzed for the presence or absence of at least four polymorphisms associated with pain perception, persistent postoperative/chronic pain, and/or anesthetic-, analgesic-, and/or opioid-related adverse effects.

As disclosed herein, particular marker alleles or haplotypes (e.g. ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKKI rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, V158M rs4680, the CYP2D6*2, *2A, *3, *4, *5, *6, *7, *8, *9, *10, *11, *14, *15, *17, *18, *19, *20, *35, *40, *41, *42, and *44 alleles, the PharmacoGenomics Research Network (PGRN) genetic markers on the PGRN-Seq genetic markers platform (Table 16), and markers in linkage disequilibrium therewith can be associated with development of adverse effects to one or more administered anesthesia, analgesic, and/or opioid. In some embodiments, the marker allele or haplotype is one that confers a significant risk or susceptibility to developing such effects. Accordingly, in embodiments of the invention, a method of determining a risk or a susceptibility to developing adverse effects from administered anesthesia, analgesic, and/or opioid in a subject is provided, the method comprising determining the presence or absence of at least one allele of at least one polymorphic marker in a nucleic acid sample obtained from the subject, wherein the at least one polymorphic marker is selected from the group consisting of: ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKKI rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, V158M rs4680, the CYP2D6*2, *2A, *3, *4, *5, *6, *7, *8, *9, *10, *11, *14, *15, *17, *18, *19, *20, *35, *40, *41, *42, and *44 alleles, the PGRN-Seq genetic markers (Table 16), and markers in linkage disequilibrium therewith.

In some embodiments, a method of determining a risk or a susceptibility to developing adverse effects from administered anesthesia, analgesic, and/or opioid in a subject is provided, the method comprising screening for at least one marker selected from ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKKI rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, the CYP2D6*2, *2A, *3, *4,*5, *6, *7, *8, *9, *10, *11, *14, *15, *17, *18, *19, *20, *35, *40, *41, *42, and *44 alleles, the PGRN-Seq genetic markers (Table 16), and markers in linkage disequilibrium therewith. In some embodiments, the marker allele or haplotype is more frequently present in a subject having, or who is susceptible to, developing adverse effects from administered anesthesia (affected), as compared to the frequency of its presence in a healthy subject (control, such as population controls). In some embodiments, the significance of association of the at least one marker allele or haplotype is characterized by a p-value<0.05. In some embodiments, the significance of association is characterized by smaller p-values, such as <0.01, <0.001, <0.0001, <0.00001, <0.000001, <0.0000001, <0.00000001 or <0.000000001.

Embodiments of the invention are also directed to a composition for identifying a patient at risk for suffering adverse effects from administered anesthesia, analgesic, and/or opioid, comprising at least one polymorphism associated with pain perception, persistent postoperative/chronic pain, and/or analgesic and anesthetic adverse effects. In some embodiments, the composition comprises at least two polymorphisms associated with pain perception, persistent postoperative/chronic pain, and/or anesthetic adverse effects. In some embodiments, the composition comprises at least three polymorphisms associated with pain perception, persistent postoperative/chronic pain, and/or anesthetic adverse effects. In some embodiments, the composition comprises at least four polymorphisms associated with pain perception, persistent postoperative/chronic pain, and/or anesthetic adverse effects. In some embodiments, the composition comprises a gene chip. In some embodiments, the composition comprises a surface with a DNA array.

Embodiments of the invention include use of each gene or each polymorphism separately as a diagnostic or prognostic marker, or use of a few marker genes combined into a panel display format so that several marker genes can be detected to increase reliability and efficiency. Further, any of the genes or polymorphisms identified as disclosed herein can be used individually or as a set of genes in any combination with any of the other genes or other polymorphisms that are disclosed in the application.

Exemplary Markers

In relatively small adult studies, specific polymorphisms of the catechol-o-methyltransferase (COMT), mu opioid receptor (OPRM1), and the ATP binding cassette B1 (ABCB1) (also known as MCR1) genes have been associated with high pain sensitivity, increased morphine requirement and side effects. As disclosed herein, heretofore unknown genetic variations were identified that represent high risk factors of opioid-related adverse effects and poor pain control. These genetic variations and risk factors are predictive of potential outcomes and can be used to create decision trees and algorithms based upon these biomarkers to enable personalized interventions that can be clinically implemented. These decision trees and algorithms can be used to evaluate the efficacy and safety of administering opioids and/or analgesics.

The use of the decision trees and algorithms described herein can improve perioperative clinical outcomes by providing better analgesia with minimal adverse effects, as well as economic outcomes, by reducing prolonged PACU stays, emergency room visits for inadequate pain control, dehydration following opioid-induced vomiting, and respiratory depression requiring oxygen and intense respiratory support measures. These clinical decision algorithms can enable tailored opioid selection and dosing to maximize pain relief while minimizing serious adverse effects. These findings can be extrapolated to adults and children with surgical or non-surgical pain requiring opioids.

The results described herein disclose critically important findings regarding inter-individual variations in pain perception and opioid responses. This information provides the essential foundation for clinical decision algorithms that enable tailored opioid selection and dosing so as to maximize pain relief while minimizing serious adverse-effects in children. Millions of children have the potential to benefit from this research, which will improve safety, quality of care, and economics of perioperative care.

Drug transporters at the blood-brain barrier, including the ATP binding cassette B1 (ABCB1) transporter protein, have the potential to significantly influence the clinical efficacy and safety of opioids. SNPs can therefore impact inter-individual variability in response to opioids, and gene variants have been shown to modulate cerebral pharmacokinetics of morphine and increase its analgesic and side effects. For example, adult carriers of the GG variant of the mu opioid receptor (OPRM1) SNP, A118G, can require up to a 2-4 fold higher dose of morphine than AA variants.

As disclosed herein, preliminary experiments comparing genotypes of ABCB1 (rs1045642) from 150 children undergoing tonsillectomy showed 4 to 10 fold inter-individual variations in morphine's respiratory depression and postoperative nausea and vomiting (PONV). Furthermore, allelic frequency of the TT genotype in ABCB1, which correlates with a higher risk of respiratory depression and PONV, was 27%.

Fatty acid amide hydrolase (FAAH) is part of the endocannabinoid system, a neuromodulator of vomiting. FAAH degrades anandamide, as an endogenous agonist for CB1 receptors. Canniboid agonists are effective antiemetics against opioids through CB1 receptors. As disclosed herein, genetic variations in FAAH (rs4141964) can have strong associations with opioid adverse effects, especially PONV and prolonged PACU stays. As further disclosed herein, genetic variations in TRPA1 (rs1443952) can also have strong associations with opioid adverse effects.

Catechol-o-methyltransferase (COMT) is a key regulator of pain perception, cognitive function, and affective mood. COMT is also a pivotal regulator of catecholamines concentrations in the pain perception pathway. Haplotypes of four common COMT SNPs (rs6269, rs4633, rs4818, and rs4680) have been shown to be associated with three levels of pain perceptions (low, average, and high pain sensitivity). Additionally, the V158M polymorphism (rs4680) influences the human response to pain. As disclosed herein, there can be strong associations between COMT and inter-individual variations in pain scores and opioid requirements. Certain GCH1 and other genotypes are associated with persistent postoperative/chronic pain.

OSA is over-represented among African-American patients, who in turn are more likely to be at a higher risk of inadequate pain relief, as indicated by the efficacy tree described herein. OSA and race therefore represent important covariates; this is further highlighted by the finding that ADRB2 and FAAH gene polymorphisms can be used to relatively accurately predict race (with ~80% prediction accuracy). However, OSA itself seems to have a relatively strong, although poorly understood, genetic component (Larkin, E. et al. Resp. Crit. Care Med. 182:947-53 (2010)). As disclosed herein, OSA can be predicted using SNPs in just two genes (ADRB2 rs1042717 and ABCB1). A simple decision rule was developed that expresses the risk of OSA; this decision rule achieves about 73% classification accuracy (compared to 50% for a baseline classifier).

As described herein, a systematic study was conducted to identify much less understood genetic variants underlying clinical responses to opioids in children with the goal of improving and personalizing the postoperative care and pain management in children. A standardized site study protocol allowed for unambiguous assignment and accurate quantification of the observed phenotypes. Genotype data was collected using a specialized SNP panel. The candidate genes included ABCB1, COMT, OPRM1, FAAH, ADRB2 and a number of other genes that were chosen based on their allele frequencies and clinical evidences of important associations in adults with opioid analgesic and adverse effects.

Preliminary statistical analyses revealed several significant associations between genetic, as well as non-genetic factors and postoperative opioid adverse effects and inadequate analgesia. In particular, the TT genotype of the ABCB1 SNP rs1045642 (C3435T) was found (after adjusting for obstructive sleep apnea) to be associated with a higher risk of morphine-induced respiratory depression than the CC genotype. In the ABCB1 TT genotype, resting minute ventilation (MV) after morphine decreased by 47.5% compared to only 18.4% in CC and CT genotypes (p<0.05). At the same time, a number of other, relatively weak associations with SNPs in FAAH, COMT, and other genes, as well as indication of epistatic interactions between, e.g., ABCB1 and FAAH (as well as ABCB1 and ADRB2) SNPs were found.

Different strata with distinct patterns of such interactions (with ABCB1 playing a prominent role in some strata) were identified. These data also suggest that African American children had inadequate pain control, while Caucasian children had higher incidence of adverse effects from similar doses of morphine.

Significant differences were found in the allelic frequency of ABCB1 (and other genes). For example, the TT genotype of ABCB1 SNP rs1045642 that predisposes children to opioid induced respiratory depression (with >4 fold higher incidence than the CC genotype) was found to be as frequent as 27% in Caucasian children, as compared to 2-3% in our African-American children.

In some embodiments, the at least one polymorphism that is analyzed is one that is found in a gene from selected from the group of: ABCB1, ABCC2, ABCC3, ABCD1, ADRB2, ANKK1, beta-arrestin-2, COMT, CHRM3, CNR1, CNR2, CYP2D6, CYP3A4, CYP2C9, DRD2, eCNOS, FAAH, FLJ37396, GCH1, GRIN2B, HTR2A, IL1RN, IL2RB, KCNB2, KCNJ6, LOC100287246, MDR1, MC1R, NBPF22P, NTRK1, OCT1, OPRM1, PTGS1, PTGS2, SLC6A2, SLC6A4, SCN9A, Stat6, TANK, TRPA1, TRPV1, TNF-alpha, TACR1, UGT2B7, UGT2B14, UGT2B15, UGT2B17, UGT1A1, UGT1A3, UGT1A6, UGT1A8, V158M, and ZNF429.

In some embodiments, the at least one polymorphism that is analyzed is selected from the group of: ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKKI rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, V158M rs4680 activity, the CYP2D6*2, *2A, *3, *4, *5, *6, *7, *8, *9, *10, *11, *14, *15, *17, *18, *19, *20, *35, *40, *41, *42, and *44 alleles, and the PGRN-Seq genetic markers (Table 16).

The polymorphisms as disclosed herein can be correlated with pain perception, persistent postoperative/chronic pain, anesthetic or opioid requirement, and anesthetic or opioid adverse effects. In some embodiments, the polymorphisms as disclosed herein are correlated with pain perception, persistent postoperative/chronic pain, anesthetic or opioid requirement, and anesthetic-, analgesic-, and/or opioid-related adverse effects in a pediatric patient. In some embodiments, the polymorphisms as disclosed herein can be correlated with OSA.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome. For example, the human genome exhibits sequence variations which occur on average every 500 base pairs. The most common sequence variant consists of base variations at a single base position in the genome, and such sequence variants, or polymorphisms, are commonly called SNPs. These SNPs are believed to have occurred in a single mutational event, and therefore there are usually two possible alleles possible at each SNP site: the original allele and the mutated allele. Due to natural genetic drift and possibly also selective pressure, the original mutation has resulted in a polymorphism characterized by a particular frequency of its alleles in any given population. Many other types of sequence variants are found in the human genome, including mini- and microsatellites, and insertions, deletions, and inversions (also called copy number variations (CNVs)). A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus, in some embodiments of the invention, the polymorphism is characterized by the presence of two or more alleles in any given population. In some embodiments, the polymorphism is characterized by the presence of three or more alleles. In some embodiments, the polymorphism is characterized by four or more alleles, five or more alleles, six or more alleles, seven or more alleles, nine or more alleles, or ten or more alleles. All such polymorphisms can be utilized in the methods and kits as disclosed herein.

Reference can be made to different alleles at a polymorphic site without choosing a reference allele. Alternatively, a reference sequence can be referred to for a particular polymorphic site. The reference allele can be referred to as the "wild-type" allele, and it usually is chosen as either the first sequenced allele or as the allele from a "non-affected" individual (e.g. an individual that does not display a trait or disease phenotype).

Alleles for SNP markers as referred to herein refer to the bases A, C, G, or T as they occur at the polymorphic site in the SNP assay employed. The allele codes for SNPs used herein are as follows: 1=A, 2=C, 3=G, 4=T. However, the person skilled in the art will understand that by assaying or reading the opposite DNA strand, the complementary allele can in each case be measured. Thus, for a polymorphic site (polymorphic marker) characterized by an A/G polymorphism, the assay employed can be designed to specifically detect the presence of one or both of the two bases possible, i.e. A and G. Alternatively, by designing an assay that is designed to detect the complimentary strand on the DNA template, the presence of the complementary bases T and C can be measured. Quantitatively (for example, in terms of relative risk), identical results would be obtained from measurement of either DNA strand (+strand or −strand).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e. a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g. SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (e.g. Chen, X. et al., *Genome Res.* 9(5): 492-98 (1999); Kutyavin et al., *Nucleic Acid Res.* 34:e128 (2006)), utilizing PCR, LCR, Nested PCR, and other techniques for nucleic acid amplification. Specific commercial methodologies available for SNP genotyping include, but are not limited to, TaqMan genotyping assays and SNPlex platforms (Applied Biosystems), gel electrophoresis (Applied Biosystems), mass spectrometry (e.g. MassARRAY system from Sequenom), minisequencing methods, real-time PCR, Bio-Plex system (BioRad), CEQ and SNPstream systems (Beckman), array hybridization technology (e.g. Affymetrix GeneChip; Perlegen), BeadArray Technologies (e.g. Illumina GoldenGate and Infinium assays), array tag technology (e.g. Parallele), and endonuclease-based fluorescence hybridization technology (Invader; Third Wave). Thus, by use of these or other methods available to the person skilled in the art, one or more alleles at polymorphic markers, including microsatellites, SNPs, or other types of polymorphic markers, can be identified.

As disclosed herein, an individual who is at an increased susceptibility (i.e. increased risk) for a disease or trait is an individual in whom at least one specific allele at one or more polymorphic marker or haplotype conferring increased susceptibility (increased risk) for the disease or trait is identified (i.e. at-risk marker alleles or haplotypes). The at-risk marker or haplotype is one that confers an increased risk (increased susceptibility) of the disease. In some embodiments, significance associated with a marker or haplotype is measured by a relative risk (RR). In some embodiments, significance associated with a marker or haplotype is measured by an odds ratio (OR). In a further embodiment, the significance is measured by a percentage. In some embodiments, a significant increased risk is measured as a risk (relative risk and/or odds ratio) of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, and at least 5.0. In some embodiments, a risk (relative risk and/or odds ratio) of at least 1.2 is significant. In some embodiments, a risk of at least 1.3 is significant. In some embodiments, a risk of at least 1.4 is significant. In some embodiments, a relative risk of at least 1.5 is significant. In some embodiments, a significant increase in risk is at least 1.7 is significant. However, other cutoffs are also contemplated, e.g. at least 1.15, 1.25, 1.35, and so on, and such cutoffs are also within scope of the present invention. In some embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In some embodiments, a significant increase in risk is at least 20%. In some embodiments, a significant increase in risk is at least 30%, at least 40%, at least 50%, at least 60%, at least 70%, at least 80%, at least 90%, and at least 100%. Other cutoffs or ranges as deemed suitable by the person skilled in the art to characterize the invention are however also contemplated, and those are also within scope of the present invention. In some embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype as described herein is one where at least one allele of at least one marker or haplotype is more frequently present in an individual at risk for the disease (or trait) (affected), or diagnosed with the disease, compared to the frequency of its presence in a comparison group (control), such that the presence of the marker or haplotype is indicative of susceptibility to the disease. In some embodiments, the control group can be a population sample, i.e. a random sample from the general population. In some embodiments, the control group is represented by a group of individuals who are disease-free. In some embodiments, such disease-free controls can be characterized by the absence of one or more specific disease-associated symptoms. Alternatively, the disease-free controls are those that have not been diagnosed with the disease. In some embodiments, the disease-free control group is characterized by the absence of one or more disease-specific risk factors. In some embodiments, such risk factors include at least one environmental risk factor. Representative environmental factors are natural products, minerals, or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In some embodiments, the risk factors comprise at least one additional genetic risk factor.

An example of a simple test for correlation would be a Fisher-exact test on a two by two table. Given a cohort of chromosomes, the two by two table is constructed out of the number of chromosomes that include both of the markers or haplotypes, one of the markers or haplotypes but not the other, and neither of the markers or haplotypes. Other statistical tests of association known to the skilled person are also contemplated and are also within scope of the invention.

In some embodiments of the invention, an individual who is at a decreased susceptibility (i.e. at a decreased risk) for a disease or trait is an individual in whom at least one specific allele at one or more polymorphic marker or haplotype conferring decreased susceptibility for the disease or trait is identified. The marker alleles and/or haplotypes conferring decreased risk are also said to be protective. In some embodiments, the protective marker or haplotype is one that confers a significant decreased risk (or susceptibility) of the disease or trait. In some embodiments, significant decreased risk is measured as a relative risk (or odds ratio) of less than 0.9, including but not limited to less than 0.9, less than 0.8, less than 0.7, less than 0.6, less than 0.5, less than 0.4, less than 0.3, less than 0.2, and less than 0.1. In some embodiments, significant decreased risk is less than 0.7. In some embodiments, significant decreased risk is less than 0.5. In some embodiments, significant decreased risk is less than 0.3. In some embodiments, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, and at least 98%. In some embodiments, a significant decrease in risk is at least about 30%. In some embodiments, a significant decrease in risk is at least about 50%. In some embodiments, the decrease in risk is at least about 70%. Other cutoffs or ranges as deemed suitable by the person skilled in the art to characterize the invention are however also contemplated, and those are also within scope of embodiments of the invention.

The person skilled in the art will appreciate that for markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

A genetic variant associated with a disease or a trait can be used alone to predict the risk of the disease for a given genotype. For a biallelic marker, such as an SNP, there are three possible genotypes: homozygote for the at-risk variant, heterozygote, and non-carrier of the at-risk variant. Risk associated with variants at multiple loci can be used to estimate overall risk. For multiple SNP variants, there are k possible genotypes, with $k=3^n \times 2^p$; where n is the number autosomal loci, and p the number of gonosomal (sex chromosomal) loci. Overall risk assessment calculations for a plurality of risk variants typically assume that the relative risks of different genetic variants multiply, i.e. the overall risk (e.g. RR or OR) associated with a particular genotype combination is the product of the risk values for the genotype at each locus. If the risk presented is the relative risk for a person or a specific genotype for a person, compared to a reference population with matched gender and ethnicity, then the combined risk is the product of the locus-specific risk values and which also corresponds to an overall risk estimate compared with the population. If the risk for a person is based on a comparison to non-carriers of the at-risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e. non-carriers) of 1.0 but has an overall risk, compared with the population, of less than 1.0. It should be noted that the group of non-carriers can potentially be very small, especially for a large number of loci, and, in that case, its relevance is correspondingly small.

The multiplicative model is a parsimonious model that usually fits the data of complex traits reasonably well. Deviations from multiplicity have been rarely described in the context of common variants for common diseases and if reported are usually only suggestive, since very large sample sizes are typically required to be able to demonstrate statistical interactions between loci.

By way of example, consider a total of eight variants that have been described to associate with prostate cancer (Gudmundsson, et al., *Nat Genet* 39:631-7 (2007); Gudmundsson, et al., *Nat Genet* 39:977-83 (2007); Yeager, et al., *Nat Genet* 39:645-49 (2007); Amundadottir, et al., *Nat Genet* 38:652-8 (2006); Haiman, et al., *Nat Genet* 39:638-44 (2007)). Seven of these loci are on autosomes, and the remaining locus is on chromosome X. The total number of theoretical genotypic combinations is then $3^7 \times 2^1 = 4374$. Some of those genotypic classes are very rare but are still possible, and these can be considered for overall risk assessment. The multiplicative model applied in the case of multiple genetic variants can also be valid in conjugation with non-genetic risk variants, assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Using the same quantitative approach, the combined or overall risk associated with a plurality of variants associated with adverse anesthetic effects can be assessed, including combinations of any one of the markers and/or polymorphisms as disclosed herein or markers in linkage disequilibrium therewith.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as linkage disequilibrium (LD) blocks (Myers, et al., *Biochem Soc Trans* 34:526-30 (2006); Jeffreys, et al., *Nat Genet* 29:217-22 (2001); May, et al., *Nat Genet* 31:272-5 (2002)).

Linkage disequilibrium (LD) refers to a non-random assortment of two genetic elements. For example, if a particular genetic element (e.g. an allele of a polymorphic marker, or a haplotype) occurs in a population at a frequency of 0.50 (50%), and another element occurs at a frequency of 0.50 (50%), then the predicted occurrence of a person's having both elements is 0.25 (25%), assuming a random distribution of the elements. However, if it is discovered that the two elements occur together at a frequency higher than 0.25, then the elements are said to be in linkage disequilibrium, since they tend to be inherited together at a higher rate than what their independent frequencies of occurrence (e.g. allele or haplotype frequencies) would predict. Roughly speaking, LD is generally correlated with the frequency of recombination events between the two elements. Allele or haplotype frequencies can be determined in a population by genotyping individuals in a population and determining the frequency of the occurrence of each allele or haplotype in the population. For populations of diploids, e.g. human populations, individuals will typically have two alleles or allelic combinations for each genetic element (e.g. a marker, haplotype, or gene).

Many different measures have been proposed for assessing the strength of linkage disequilibrium (reviewed in Devlin, B. & Risch, N., *Genomics* 29:311-22 (1995)). Most capture the strength of association between pairs of bi-allelic sites. Two important pairwise measures of LD are $r^2$ (sometimes denoted $\Delta^2$) and |D'| (Lewontin, R., *Genetics* 49:49-67 (1964); Hill, W. G. & Robertson, A. *Theor. Appl. Genet.* 22:226-231 (1968)). Both measures range from 0 (no disequilibrium) to 1 ("complete" disequilibrium), but their interpretation is slightly different. |D'| is defined in such a way that it is equal to 1 if just two or three of the possible haplotypes are present, and it is <1 if all four possible haplotypes are present. Therefore, a value of |D'| that is <1 indicates that historical recombination can have occurred between two sites (recurrent mutation can also cause |D'| to be <1, but for SNPs, this is typically regarded as being less likely than recombination). The measure $r^2$ represents the statistical correlation between two sites and takes the value of 1 if only two haplotypes are present.

The $r^2$ measure is a relevant measure for association mapping because there is a simple inverse relationship between $r^2$ and the sample size sufficient to detect association between susceptibility loci and SNPs. These measures are defined for pairs of sites, but, for some applications, a determination of how strong LD is across an entire region that contains many polymorphic sites can be desirable (e.g. testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be sufficient under a particular population model to generate the LD that is seen in the data. This type of method can also provide a statistically rigorous approach to the problem of determining whether LD data provide evidence for the presence of recombination hotspots. For the methods described herein, a significant $r^2$ value can be at least 0.1, such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, or at least 0.99. In some embodiments, the significant $r^2$ value can be at least 0.2. Alternatively, linkage disequilibrium as described herein refers to linkage disequilibrium characterized by |D'| values of at least 0.2, such as 0.3, 0.4, 0.5, 0.6, 0.7, 0.8, 0.85, 0.9, 0.95, 0.96, 0.97, 0.98, or at least 0.99. Thus, linkage disequilibrium represents a correlation between alleles of distinct markers. It is measured by correlation coefficient or |D'| ($r^2$ up to 1.0 and |D'| up to 1.0). In some embodiments, linkage disequilibrium is defined in terms of values for both the $r^2$ and |D'| measures. In some embodiments, a significant linkage disequilibrium is defined as $r^2>0.1$ and |D'|>0.8. In some embodiments, a significant linkage disequilibrium is defined as $r^2>0.2$ and |D'|>0.9. Other combinations and permutations of values of $r^2$ and |D'| for determining linkage disequilibrium are also contemplated, and are also within the scope of embodiments of the invention. Linkage disequilibrium can be determined in a single human population, as defined herein, or it can be determined in a collection of samples comprising individuals from more than one human population. In some embodiments, LD is determined in a sample from one or more of the HapMap populations (Caucasian, African, Japanese, Chinese) (as defined at http<colon slash slash>www<dot>hapmap<dot>org).

If all polymorphisms in the genome were independent at the population level (i.e. no LD), then every single one of them would need to be investigated in association studies, to assess all the different polymorphic states. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms can give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, et al., *Proc Natl Acad Sci USA* 99:2228-2233 (2002); Reich, et al., *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, et al., *Nature Genet.* 29:229-232 (2001); Gabriel, et al., *Science* 296:2225-2229 (2002); Patil, et al., *Science* 294: 1719-1723 (2001); Dawson, et al., *Nature* 418:544-548 (2002); Phillips, et al., *Nature Genet.* 33:382-387 (2003)).

There are two main methods for defining these haplotype blocks: blocks can be defined as regions of DNA that have limited haplotype diversity (see, e.g., Daly, et al., *Nature Genet.* 29:229-232 (2001); Patil, et al., *Science* 294:1719-1723 (2001); Dawson, et al., *Nature* 418:544-548 (2002); Zhang, et al., *Proc. Natl. Acad. Sci. USA* 99:7335-7339 (2002)), or as regions between transition zones having extensive historical recombination, identified using linkage disequilibrium (see, e.g., Gabriel, et al., *Science* 296:2225-2229 (2002); Phillips, et al., *Nature Genet.* 33:382-387 (2003); Wang, et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, et al., Science 310:321-32324 (2005); Myers, et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks (LD blocks) can be used to map associations between phenotype and haplotype status, using single markers or haplotypes comprising a plurality of markers. The main haplotypes can be identified in each haplotype block, and a set of "tagging" SNPs or markers (the smallest set of SNPs or markers sufficient to distinguish among the haplotypes) can then be identified. These tagging SNPs or markers can then be used in assessment of samples from groups of individuals, in order to identify association between the phenotype and haplotype. If desired, neighboring haplotype blocks can be assessed concurrently, as there can also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait and as such are useful for use in the methods and kits of the present invention. One or more causative (functional) variants or mutations can reside within the region found to be associating to the disease or trait. The functional variant can be another SNP, a tandem repeat polymorphism (such as a minisatellite or a microsatellite), a transposable element, or a copy number variation, such as an inversion, deletion, or insertion. Such variants in LD with the variants described herein can confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in some embodiments of the invention, markers that are in LD with the markers and/or haplotypes of the invention, as described herein, can be used as surrogate markers. The surrogate markers have in some embodiments relative risk (RR) and/or odds ratio (OR) values smaller than for the markers or haplotypes initially found to be associating with the disease, as described herein. In some embodiments, the surrogate markers have RR or OR values greater than those initially determined for the markers initially found to be associating with the disease, as described herein. An example of such an embodiment would be a rare or relatively rare (such as <10% allelic population frequency) variant in LD with a more common variant (>10% population frequency) initially found to be associating with the disease, such as the variants described herein. Identifying and using such markers for detecting the association discovered by the inventors as described herein can be performed by routine methods well-known to the person skilled in the art and are therefore within the scope of the present invention.

Determination of Haplotype Frequency

The frequencies of haplotypes in patient and control groups can be estimated using an expectation-maximization algorithm (Dempster, et al., *J. R. Stat. Soc.* 8, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk haplotype, which can include the markers described herein, is allowed to have a higher frequency in patients than controls, while the ratios of the frequencies of other haplotypes are assumed to be the same in both groups. Likelihoods are maximized separately under both hypotheses, and a corresponding 1-df likelihood ratio statistic is used to evaluate the statistical significance.

To look for at-risk and protective markers and haplotypes within a susceptibility region, for example within an LD block, association of all possible combinations of genotyped markers within the region is studied. The combined patient and control groups can be randomly divided into two sets, equal in size to the original group of patients and controls. The marker and haplotype analysis is then repeated, and the most significant p-value registered is determined. This randomization scheme can be repeated, for example, over 100 times to construct an empirical distribution of p-values. In some embodiments, a p-value of <0.05 is indicative of a significant marker and/or haplotype association.

Risk Assessment and Diagnostics

Within any given population, there is an absolute risk of developing a disease or trait, defined as the chance of a person developing the specific disease or trait over a specified time period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of absolute risk (AR) and relative risk (RR). Relative risk is used to compare risks associated with two variants or the risks of two different groups of people. For example, it can be used to compare a group of people with a certain genotype with another group having a different genotype. For a disease or trait, a relative risk of 2 means that one group has twice the chance of developing the disease or trait as the other group. The risk presented is usually the relative risk for a person, or a specific genotype of a person, compared to the population with matched gender and ethnicity. Risks of two individuals of the same gender and ethnicity can be compared in a simple manner. For example, if, compared to the population, the first individual has a relative risk of 1.5, and the second has a relative risk of 0.5, then the risk of the first individual compared to the second individual is 1.5/0.5=3.

Risk Calculations

The creation of a model to calculate the overall genetic risk involves two steps: i) conversion of odds-ratios for a single genetic variant into relative risk, and ii) combination of risk from multiple variants in different genetic loci into a single relative risk value.

Deriving Risk from Odds-Ratios

Most gene discovery studies for complex diseases or traits that have been published to date in authoritative journals have employed a case-control design due to their retrospective setup. These studies sample and genotype a selected set of cases (people who have the specified disease condition) and control individuals. The interest is in genetic variants (alleles) whose frequency in cases and controls differ significantly.

The results are typically reported in odds ratios, which describe the ratio between the fraction (probability) with the risk variant (carriers) versus the non-risk variant (non-carriers) in the groups of affected versus the controls, i.e. expressed in terms of probabilities conditional on the affection status:

$$OR=(Pr(c|A)/Pr(nc|A))/(Pr(c|C)/Pr(nc|C))$$

In some embodiments, the absolute risk for the disease or trait is what is determined, i.e. the fraction of those individuals carrying the risk variant who get the disease or, in other words, the probability of getting the disease. This number cannot be directly measured in case-control studies, in part because the ratio of cases versus controls is typically not the same as that in the general population. However, under certain assumptions, the risk can be calculated from the odds ratio value.

Combining the Risk from Multiple Markers

When genotypes of many SNP variants are used to estimate the risk for an individual, unless otherwise stated, a multiplicative model for risk can be assumed. This means that the combined genetic risk relative to the population is calculated as the product of the corresponding estimates for individual markers, e.g. for two markers g1 and g2:

$$RR(g1,g2)=RR(g1)RR(g2)$$

The underlying assumption is that the risk factors occur and behave independently, i.e. that the joint conditional probabilities can be represented as products:

$$Pr(A|g1,g2)=Pr(A|g1)Pr(A|g2)/Pr(A) \text{ and}$$
$$Pr(g1,g2)=Pr(g1)Pr(g2)$$

In embodiments where markers are closely spaced on the genome, i.e. are in linkage disequilibrium such that the concurrence of two or more risk alleles is correlated, a haplotype modeling where the odds-ratios are defined for all allele combinations of the correlated SNPs can be employed.

As an example, consider an individual who has the following genotypes at four markers associated with risk of type-2 diabetes along with the risk relative to the population at each marker:

Chromo 3 PPARG CC Calculated risk: RR(CC)=1.03
Chromo 6 CDKAL1 GG Calculated risk: RR(GG)=1.30
Chromo 9 CDKN2A AG Calculated risk: RR(AG)=0.88
Chromo 11 TCF7L2 TT Calculated risk: RR(TT)=1.54

Combined, the overall risk relative to the population for this individual is:

$$1.03 \times 1.30 \times 0.88 \times 1.54 = 1.81.$$

Risk Assessment for Adverse Anesthetic Effects

As disclosed herein, certain polymorphic markers and haplotypes comprising such markers are found to be useful for risk assessment of adverse reactions to surgical anesthesia. Risk assessment can involve the use of the markers for determining a susceptibility to such adverse effects. Particular alleles of polymorphic markers (e.g. SNPs) are found more frequently in individuals with particular susceptibility to such adverse effects. Therefore, these marker alleles have predictive value for determining whether these individuals will suffer post-operative adverse effects from administered anesthesia, or a susceptibility to the same. Tagging markers in linkage disequilibrium with at-risk variants (or protective variants) as disclosed herein can be used as surrogates for these markers (and/or haplotypes). Such surrogate markers can be located within a particular haplotype block or LD block. Such surrogate markers can also sometimes be located outside the physical boundaries of such a haplotype block or LD block, either in close vicinity of the LD block/haplotype block or possibly also located in a more distant genomic location.

Long-distance LD can arise if particular genomic regions (e.g. genes) are in a functional relationship. For example, if two genes encode proteins that play a role in a shared metabolic pathway, then particular variants in one gene can have a direct impact on observed variants for the other gene. An example is a case where a variant in one gene leads to increased expression of the gene product. To counteract this effect and preserve overall flux of the particular pathway, this variant can have led to selection of one (or more) variants at a second gene that confers decreased expression levels of that gene. These two genes can be located in different genomic locations, possibly on different chromosomes, but variants within the genes are in apparent LD, not because of their shared physical location within a region of high LD but rather due to evolutionary forces. Such LD is also contemplated and within the scope of embodiments of the invention. The skilled person will appreciate that many other scenarios of functional gene-gene interaction are possible, and the particular example discussed here represents only one such possible scenario.

Markers with values of $r^2$ equal to 1 are equivalent surrogates for the at-risk variants, i.e. genotypes for one marker perfectly predict genotypes for the other. Markers with smaller values of $r^2$ than 1 can also be surrogates for the at-risk variant or alternatively represent variants with relative risk values as high as or possibly even higher than the at-risk variant. The at-risk variant identified is not necessarily the functional variant itself but is in this instance in linkage disequilibrium with the true functional variant. The functional variant can, for example, be a tandem repeat, such as, but not limited to, a minisatellite or a microsatellite, a transposable element (e.g. an A/u element), or a structural alteration, such as a deletion, insertion, or inversion (sometimes also called copy number variations, or CNVs). Embodiments of the invention encompass the assessment of such surrogate markers for the markers as disclosed herein. Such markers are annotated, mapped, and listed in public databases, as is well-known to the skilled person, or can alternatively be readily identified by sequencing the region or a part of the region identified by the markers of the present invention in a group of individuals and identify polymorphisms in the resulting group of sequences. As a consequence, the person skilled in the art can readily and without undue experimentation genotype surrogate markers in linkage disequilibrium with the markers and/or haplotypes as described herein. The tagging or surrogate markers in LD with the detected at-risk variants also have predictive value for detecting association to adverse anesthetic effects, or a susceptibility to the same, in an individual. These tagging or surrogate markers that are in LD with the identified markers as disclosed herein can also include other markers that distinguish among haplotypes, as these similarly have predictive value for detecting susceptibility to the particular trait.

Embodiments of the invention can be directed to methods of assessing a sample comprising genomic DNA from an individual for the presence of variants described herein to be associated with adverse anesthetic effects. Such methods typically comprise steps that detect the presence or absence of at least one allele of at least one polymorphic marker, using methods well-known to the skilled person and further described herein, and, based on the outcome of such assessment, determine whether the individual from whom the sample is derived is at increased or decreased risk (increased or decreased susceptibility) of adverse anesthetic effects. In some embodiments, detecting particular alleles of polymorphic markers can be carried out by obtaining nucleic acid sequence data about a particular human individual that identifies at least one allele of at least one polymorphic marker. Different alleles of the at least one marker are associated with different susceptibility to such effects in humans. Obtaining nucleic acid sequence data can comprise identifying the nucleic acid sequence at a single nucleotide position, which is sufficient to identify alleles at SNPs. The nucleic acid sequence data can also comprise sequence information at any other number of nucleotide positions, in particular for genetic markers that comprise multiple nucleotide positions, and can be anywhere from two to hundreds of thousands, possibly even millions, of nucleotides (in particular, in the case of CNVs).

In some embodiments, the methods comprise utilization of a dataset comprising information about the genotype status of at least one polymorphic marker associated with a disease or trait (or markers in linkage disequilibrium with at least one marker associated with the disease or trait). In other words, a dataset containing information about such genetic status, for example in the form of sequence data, genotype counts at a certain polymorphic marker, or a plurality of markers (e.g. an indication of the presence or absence of certain at-risk alleles), or actual genotypes for one or more markers, can be queried for the presence or absence of certain at-risk alleles at certain polymorphic markers as disclosed herein to be associated with the disease or trait. A positive result for a variant (e.g. marker allele) associated with the disease or trait is indicative of the individual from whom the dataset is derived is at increased susceptibility (increased risk) of the disease.

In some embodiments, a polymorphic marker is correlated to a disease or trait by referencing genotype data for the polymorphic marker to a look-up table that comprises correlations between at least one allele of the polymorphism and the disease. In some embodiments, the table comprises a correlation for one polymorphism. In some embodiments, the table comprises a correlation for a plurality of polymorphisms. By referencing to a look-up table that gives an indication of a correlation between a marker and the disease, a risk for the disease or trait or a susceptibility to the disease or trait can be identified in the individual from whom the sample is derived. In some embodiments, the correlation is reported as a statistical measure. The statistical measure can be reported as a risk measure, such as a relative risk (RR), an absolute risk (AR), or an odds ratio (OR).

The markers described herein can be useful for risk assessment and diagnostic purposes, either alone or in combination. The results of the risk of suffering adverse anesthetic effects based on the markers described herein can also be combined with data for other genetic markers or risk factors for adverse anesthetic effects to establish an overall risk. Thus, even in cases where the increase in risk by individual markers is relatively modest, e.g. on the order of 10-30%, the association can have significant implications. Thus, relatively common variants can have significant contribution to the overall risk (population attributable risk is high), or combinations of markers can be used to define groups of individuals who, based on the combined risk of the markers, are at significant combined risk of developing complications due to adverse anesthetic effects.

Thus, in some embodiments, a plurality of variants (genetic markers, biomarkers, and/or haplotypes) is used for overall risk assessment. In some embodiments, these variants can be selected from the variants as disclosed herein. In some embodiments, the use of the variants as disclosed herein in combination with other variants known to be useful for diagnosing a susceptibility to adverse anesthetic effects is used. In such embodiments, the genotype status of a plurality of markers and/or haplotypes is determined in an individual, and the status of the individual is compared with the population frequency of the associated variants or the frequency of the variants in clinically healthy subjects, such as age-matched and sex-matched subjects. Methods known in the art, such as multivariate analyses or joint risk analyses or other methods known to the skilled person, can subsequently be used to determine the overall risk conferred based on the genotype status at the multiple loci. Assessment of risk based on such analysis can subsequently be used in the methods, uses, and kits of the invention, as described herein.

Individuals who are homozygous for at-risk variants for suffering adverse anesthetic effects can be at particularly high risk of developing such effects. This is due to the dose-dependent effect of at-risk alleles, such that the risk for homozygous carriers is generally estimated as the risk for each allelic copy squared.

As disclosed herein, the haplotype block structure of the human genome has the effect that a large number of variants (markers and/or haplotypes) in linkage disequilibrium with the variant originally associated with a disease or trait can be used as surrogate markers for assessing association to the disease or trait. The number of such surrogate markers will depend on factors such as the historical recombination rate in the region, the mutational frequency in the region (i.e. the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined, as disclosed herein. Such markers and/or haplotypes can in those cases be also used as surrogate markers and/or haplotypes for the markers and/or haplotypes physically residing within the haplotype block as discussed above. As a consequence, markers and haplotypes in LD (typically characterized by inter-marker $r^2$ values of greater than 0.1, such as $r^2$ greater than 0.2, including $r^2$ greater than 0.3, and also including markers correlated by values for $r^2$ greater than 0.4) with the markers and haplotypes of the present invention are also within the scope of the invention, even if they are physically located beyond the boundaries of the haplotype block as defined. This includes markers that are disclosed herein but can also include other markers that are in strong LD (e.g. characterized by $r^2$ greater than 0.1 or 0.2 and/or |D'|>0.8) with the described markers.

For the SNP markers described herein, the opposite allele to the allele found to be in excess in patients (at-risk allele) is found in decreased frequency in situations where adverse effects from anesthetic and analgesic agents are observed. These markers and haplotypes in LD and/or comprising such markers along with other factors, including age, race, weight (or body mass index, BMI), are thus protective for adverse anesthetic and analgesic effects, i.e. they confer a decreased risk or susceptibility of individuals carrying these markers and/or haplotypes developing pain and/or adverse effects from anesthetics and analgesics.

In some embodiments, variants as disclosed herein, including certain haplotypes, can comprise a combination of various genetic markers, e.g. SNPs and microsatellites. Detecting haplotypes can be accomplished by methods known in the art and/or described herein for detecting sequences at polymorphic sites. Furthermore, correlation between certain haplotypes or sets of markers and disease phenotypes can be verified using standard techniques. A representative example of a simple test for correlation would be a Fisher-exact test on a two by two table.

In some embodiments, a marker allele or haplotype found to be associated with adverse anesthetic effects is one in which the marker allele or haplotype is more frequently present in an individual at risk for suffering such effects (affected), compared to the frequency of its presence in a healthy individual (control), or in a randomly selected individual from the population, wherein the presence of the marker allele or haplotype is indicative of a susceptibility to suffering adverse anesthetic effects. In some embodiments, at-risk markers in linkage disequilibrium with one or more markers shown herein to be associated with suffering adverse anesthetic effects (e.g. marker alleles as listed in Tables 1 and 2 and Example 4) are tagging markers that are more frequently present in an individual at risk for suffering adverse anesthetic effects (affected), compared to the frequency of their presence in a healthy individual (control) or in a randomly selected individual from the population, wherein the presence of the tagging markers is indicative of increased susceptibility to suffering such effects. In some embodiments, at-risk marker alleles (i.e. conferring increased susceptibility) in linkage disequilibrium with one or more markers found to be associated with adverse anesthetic effects are markers comprising one or more allele that is more frequently present in an individual at risk for suffering such effects, compared to the frequency of their presence in a healthy individual (control), wherein the presence of the markers is indicative of increased susceptibility to suffering from adverse anesthetic effects.

Predictive Models

A decision tree is a standard machine learning technique for multivariate data analysis and classification that can be used to derive easily interpretable and intuitive rules for decision support systems. Decision tress can be viewed as a recursive partitioning approach, in which data is hierarchically divided into strata by simple logical rules. The advantage of decision trees is their simplicity, ability to handle categorical and numerical variables, as well as missing values, robustness to outliers and scaling, and the ability to combine feature selection with stratification and classification. Decision trees can also be used to derive easy to interpret and intuitive rules for decision support systems.

As described herein, decision trees are used to select and combine the most predictive SNPs with demographic, clinical, and other input features into simple logical rules that can be used to classify patients and predict adverse effects, thereby enabling robust and accurate point-of-care prediction of inadequate pain relief and opioid-related adverse effects. Such knowledge allows for individualized treatment.

As described herein, the observed distinct strata and complex interaction patterns have resulted in the systematic determination of whether interactions of specific polymorphisms of genes, such as those involved in opioid transport, sensing, and metabolism, significantly influence morphine's adverse effects in children. Due to the limitations of current approaches, there is a need for tailored solutions and extensions that can provide more robust and accurate decision rules for personalized interventions.

Distinct strata associated with specific patterns of gene-gene interactions in the context of adverse effects, pain sensitivity, and other clinical phenotypes were identified (with ABCB1 playing a prominent role in some strata) and analyzed first using standard recursive partitioning (or decision tree-based) approaches, such as CART. Genotyping, demographic, and relevant clinical data were then combined to derive logical rules for the prediction of patients with high vs. low risk of adverse effects, including opioid-induced respiratory depression outcomes. The predictive power of such models is limited by inherent biological noise, limited sample sizes, and complex pattern of interactions representing multiple mechanisms that can lead to variation in molecular and eventually clinical outcomes. Weaker associations that can manifest themselves only in the context of specific strata can be present as well but are more difficult to detect.

Decision trees and associated logical rules were enhanced by incorporating allelic (additive), dominant, and recessive models, as well as ternary trees wherein each genotype value decoupled were also implemented to facilitate identification and analysis of distinct strata. In addition, haplotype reconstruction for each gene (strong patterns of LD are observed for several genes included here) was incorporated, using Phase and similar population-based models, allowing for the simplification of decision rules and accounting for many implicit interactions observed in the data. Classical decision trees, support vector machines (SVMs), and hierarchical mixtures of experts (HME) models were integrated.

The HME approach can be viewed as a probabilistic decision tree (see Hasti et al., chapter 9 and references therein). An example of an HME decision tree is shown in FIG. 1, where the terminal nodes are called "experts" (or expert networks) that provide individual (and context-dependent) prediction of the response (in this case, adverse effects). These individual predictions are combined by the decision models ("gating networks") of the non-terminal nodes. Typically, a linear or logistic regression model is fit in each terminal node, using a linear combination of inputs, as for example in the following model for objective postoperative pain score (P) as a function of genes and other predictors:

$$E(P|X)=\beta_0+\beta_1 Age+\beta_2 Sex+\beta_3 Race+\beta_4 GCH1+\beta_5 COMT+\beta_6 ABCB1+\text{Other Factors}$$

In the above equation, $E(Y|X)$ denotes the expected value of Y given a vector of predictor variables (features) X. Expert models can be generalized using other suitable classification (or regression) approaches, such as by using robust linear SVM predictors. In this approach, terminal SVM models can be regarded as an ensemble of expert classifiers that are optimized in a context-dependent manner (including one-class SVMs when applicable).

This can be compared with developing an ensemble of classifiers optimized on different subsets of the data (such as in the context of cross-validation), which are combined to provide more robust results and associated confidence levels (which are defined in terms of consistency within the ensemble). Here, such subsets were defined by robust distinct strata obtained using standard decision trees (possibly with re-sampling and boosting as well). Thus, the tree topology of such an extended HME model would be expected to represent stable strata identified in the original decision tree analysis, addressing one of the limitations of the HME approach, namely the lack of methods for finding a good tree topology. Therefore, the resulting tree preserves the ease of interpretation of the decision rules, while improving accuracy.

Other standard statistical and machine learning methods, including neural networks, prototype, and kernel-based approaches, were also applied to further dissect patterns of gene-gene interactions and to assess their predictive power (and to evaluate relative merits of the new approach). Cross-validation, in which the overall training cohort is repeatedly (and randomly) divided into training and validation subsets, was used to evaluate the accuracy and to assess the stability of the resulting decision rules and observed strata. Standard measures of accuracy, including overall classification accuracy, precision, recall, and area under ROC curve, were used to evaluate the accuracy of the decision rules based on the proposed mixed recursive partitioning models.

As described herein, a systematic multivariate analysis of associations was initiated between gene-gene interactions and other confounding factors (such as race, age, weight or BMI, etc.) and the respective outcomes, using standard CART and C4.5 decision trees, as well as other machine learning approaches. These methods were first used to identify and analyze potential patterns of gene-gene interactions and other factors predictive of inadequate pain relief or pain sensitivity (represented by the need for the postoperative analgesic (PA) use).

The data described herein demonstrate that African-American children had inadequate pain control and Caucasian children had a higher incidence of adverse effects from similar doses of morphine (Sadhasivam S., et al., *Pediatrics*, 129:832-8(2012)). Concordant differences in allelic frequency of ABCB1 (and other genes) were observed. For example, the TT genotype of ABCB1 SNP rs1045642 that predisposes children to opioid-induced respiratory depression (>4 fold higher incidence than CC genotype) was found with 27% frequency in Caucasian children, as compared to 2-3% in African-American children.

For example, the following exemplary rules were developed and applied to the decision trees described in Examples 23 and 26, respectively:

IF(Race=African-American) THEN high risk of pain sensitivity and inadequate pain relief;

ELSE IF((Race=White) AND (GCH1 rs441417=TT)) THEN moderate risk of pain sensitivity and inadequate pain relief ELSE IF((Race=White) AND (GCH1 rs441417=CC OR CT)) THEN low risk of pain sensitivity and inadequate pain relief and IF(((ADRB2 rs1042717=GG) AND (MDR1 rs1045642=CC)) OR ((ADRB2 rs1042717=AA or GA) AND (MDR1 rs9282564=AA))) THEN increased risk of OSA Exemplary embodiments of the invention involve use of the above rules to stratify populations and provide a risk assessment for pain sensitivity and OSA risk.

Study Population

In a general sense, the methods and kits of the invention can be utilized from samples containing nucleic acid material (DNA or RNA) from any source and from any individual or from genotype data derived from such samples. In some embodiments, the individual is a human individual. The individual can be an adult, child, or fetus. The nucleic acid source can be any sample comprising nucleic acid material, including biological samples, or a sample comprising nucleic acid material derived therefrom. Embodiments of the invention also provide for assessing markers and/or haplotypes in individuals who are members of a target population. Such a target population is in one embodiment a population or group of individuals at risk of developing adverse anesthetic effects, based on other parameters such as, for example, genetic factors, biomarkers, biophysical parameters, history of anesthesia-related complications, allergic reactions to anesthesia, family history of anesthesia-related complications, and the like.

In some embodiments, the target population includes individuals from specific age subgroups, such as those under the age of 18, under the age of 16, or under the age of 12 or 10. The individuals can be of either sex, males or females.

It is believed that the markers found to be associated with adverse anesthetic, analgesia, and/or opioid effects as disclosed herein can show similar association in other human populations outside of the population employed in the current study. In some embodiments, the human subjects are from one or more human populations or ethnic groups, including, but not limited to, Caucasian populations, European populations, American populations, Eurasian populations, Asian populations, Central/South Asian populations, East Asian populations, Middle Eastern populations, African populations, Hispanic populations, and Oceanian populations.

The racial contribution in individual subjects can also be determined by genetic analysis. Genetic analysis of ancestry can be carried out using unlinked microsatellite markers such as those set out in Smith et al. (*Am J Hum Genet* 74, 1001-13 (2004)).

In some embodiments, the invention relates to markers and/or haplotypes identified in specific populations, as described in the above. The person skilled in the art will appreciate that measures of LD can give different results when applied to different populations. This is due to different population histories of different human populations as well as differential selective pressures that can have led to differences in LD in specific genomic regions. It is also well known to the person skilled in the art that certain markers, e.g. SNP markers, have different population frequencies in different populations or are polymorphic in one population but not in another. The person skilled in the art will however apply the methods available and as taught herein to practice embodiments of the invention in any given human population. This can include assessment of polymorphic markers in the LD region of the present invention, so as to identify those markers that give the strongest association within the specific population. Thus, the at-risk variants of the present invention can reside on different haplotype backgrounds and in different frequencies in various human populations. However, utilizing methods known in the art and the markers of the present invention, the invention can be practiced in any given human population.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3$^{rd}$ ed., Cold Spring Harbor Laboratory Press (Cold Spring Harbor, N.Y. 2001) provide one skilled in the art with a general guide to many of the terms used in the present application.

One skilled in the art will recognize many methods and materials similar or equivalent to those described herein, which can be used in the practice of the present invention. Indeed, the present invention is in no way limited to the methods and materials described.

Diagnostic Methods

In embodiments of the invention, methods of evaluating, or aiding in the evaluation of, a patient at risk for suffering adverse effects from administered anesthetic, analgesia, and/or opioid, are provided, the methods comprising detecting particular alleles at genetic markers that are correlated with such effects. In some embodiments, methods to determine susceptibility to developing adverse effects to administered anesthetic, analgesia, and/or opioid are provided, the methods comprising detecting at least one allele of at least one polymorphic marker (e.g. the markers described herein). As disclosed herein, particular alleles of particular markers or haplotypes are indicative of a susceptibility to suffering adverse effects from administered analgesia. Prognostic or predictive assays for evaluating a patient's risk or susceptibility to such effects can also be used to develop a customized anesthetic protocol for a subject prior to and during procedures that involve administration of anesthetic, analgesic, and/or opioid.

In some embodiments, methods of identifying a patient at risk for suffering adverse effects from administered anesthetic, analgesia, and/or opioid are carried out by analyzing samples for the presence of absence of at least one polymorphism associated with pain perception, persistent post-operative/chronic pain, and/or anesthetic-, analgesic-, and/or opioid-related adverse effects using microarray or gene chip technology, wherein the microarray or gene chip comprises the at least one polymorphism.

In some embodiments, the gene chip comprises a low density array.

In some embodiments, the methods include evaluation of additional clinical information to tailor pain therapy and anesthesia and minimize anesthetic and analgesic medication-related adverse effects. In some embodiments, the methods include evaluation of additional clinical information to tailor pain therapy and opioids and minimize opioid and analgesic medication-related adverse effects. Additional clinical information for use in such methods include, but are not limited to, patient age, race, weight (or BMI), sleep disordered breathing, gender, allergies, sensitivities, or medical conditions that affect administrative routes for delivered anesthetic, analgesia, and/or opioid. Other factors, such as, for example, ethnicity, medical history, drug interactions, psychological anxiety, stress level, and lifestyle can also be evaluated as part of the methods.

Embodiments of the invention are also directed to using recursive partitioning and decision trees to analyze genotype-phenotype associates and to identify putative strata with distinct patterns of interactions between genes and other non-genetic variables.

In embodiments of the invention, the methods comprise obtaining a sample containing genomic DNA from an individual for analysis. The sample can be, for example, a buccal swab, a saliva sample, a blood sample, or other suitable samples containing genomic DNA, as disclosed herein, and the like. The genomic DNA can be analyzed using any common technique available to the skilled person, such as, for example, high-throughput or low density array technologies, and the like. Results from such genotyping can subsequently be analyzed for the presence of certain variants known to be susceptibility variants for a particular condition, such as the genetic variants disclosed herein. Calculating risk conferred by a particular genotype for the individual can be based on comparing the genotype of the individual to previously determined risk (expressed as a relative risk (RR) or an odds ratio (OR), for example) for the genotype, for example for a heterozygous carrier of an at-risk variant for a particular condition or trait (such as for adverse effects from administered anesthesia). The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. In some embodiments, using the population average can be more convenient, since it provides a measure which is easy to interpret for the user, i.e. a measure that gives the risk for the individual, based on his/her genotype, compared with the average in the population.

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

The detection of the particular genetic marker alleles that make up particular haplotypes in the sample can be performed by a variety of methods as described herein and/or known in the art. For example, genetic markers can be detected at the nucleic acid level (e.g. by direct nucleotide sequencing or by other genotyping means known to the skilled in the art) or at the amino acid level if the genetic marker affects the coding sequence of a protein (e.g. by protein sequencing or by immunoassays using antibodies that recognize such a protein). The marker alleles or haplotypes disclosed herein correspond to fragments of genomic segments (e.g. genes) associated with development of adverse effects of administered anesthetic, analgesia, and/or opioid. Such fragments encompass the DNA sequence of the polymorphic marker or haplotype in question but can also include DNA segments in strong LD (linkage disequilibrium) with the marker or haplotype. In some embodiments, such segments comprise segments in LD with the marker or haplotype as determined by a value of $r^2$ greater than 0.2 and/or |D'|>0.8).

In some embodiments, determination of susceptibility of developing adverse effects of administered anesthesia can be carried out using hybridization methods. (See *Current Protocols in Molecular Biology*, Ausubel, F. et al., eds., John Wiley & Sons, including all supplements). The presence of a specific marker allele can be indicated by sequence-specific hybridization of a nucleic acid probe specific for the particular allele. The presence of more than one specific marker allele or a specific haplotype can be indicated by using several sequence-specific nucleic acid probes, each being specific for a particular allele. A sequence-specific probe can be directed to hybridize to genomic DNA, RNA, or cDNA. A "nucleic acid probe" can be a DNA probe or an RNA probe that hybridizes to a complementary sequence. One of skill in the art would know how to design such a probe such that sequence specific hybridization will occur only if a particular allele is present in a genomic sequence from a test sample. The invention can also be reduced to practice using any convenient genotyping method, including commercially available technologies and methods for genotyping particular polymorphic markers.

A hybridization sample can be formed by contacting the test sample containing an anesthesia adverse effect-associated nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule or a portion thereof, such as an oligonucleotide of at least 15, 30, 50, 100, 250, or 500 nucleotides in length that is sufficient to specifically hybridize under stringent conditions to appropriate mRNA or genomic DNA. In some embodiments, the nucleic acid probe can comprise at least one allele of at least one of the polymorphic markers selected from the group of: ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKKI rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, V158M rs4680, the CYP2D6*2, *2A, *3, *4, *5, *6, *7, *8, *9, *10, *11, *14, *15, *17, *18, *19,*20, *35, *40, *41, *42, and *44 alleles, the PGRN-Seq genetic markers (Table 16), and markers in linkage disequilibrium therewith, or the probe can be the complementary sequence of such a sequence. Hybridization can be performed by methods well-known to the person skilled in the art (see, e.g., *Current Protocols in Molecular Biology*, Ausubel, F. et al., eds., John Wiley & Sons, including all supplements). In some embodiments, hybridization refers to specific hybridization, i.e. hybridization with no mismatches (exact hybridization). In some embodiments, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers as disclosed herein, or markers that make up a haplotype as disclosed herein, or multiple probes can be used concurrently to detect more than one marker allele at a time. A single probe can also be designed in which the probe contains more than one marker allele of a particular haplotype (e.g. a probe containing alleles complementary to 2, 3, 4, 5, or all of the markers that make up a particular haplotype). Detection of the particular markers of the haplotype in the sample is indicative that the source of the sample has the particular haplotype (e.g. a haplotype) and therefore is susceptible or at risk of suffering adverse effects from administered anesthesia.

The detection probe can be of any suitable size, although preferably the probe is relatively short. In some embodiments, the probe is from 5-100 nucleotides in length. In some embodiments, the probe is from 10-50 nucleotides in length. In some embodiments, the probe is from 12-30 nucleotides in length. Other lengths of the probe are also contemplated and within the scope of the skill of the average person skilled in the art.

In some embodiments, the DNA template containing the SNP polymorphism is amplified by polymerase chain reaction (PCR) prior to detection. In such embodiments, the amplified DNA serves as the template for a detection probe and an enhancer probe.

In some embodiments, the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example, for increasing the melting temperature in regions containing a low percentage of G or C bases, in which modified A with the capability of forming three hydrogen bonds to its complementary T can be used, or for decreasing the melting temperature in regions containing a high percentage of G or C bases, for example, by using modified G bases that form only two hydrogen bonds to their complementary C base in a double-stranded DNA molecule. In some embodiments, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In some embodiments, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T, or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are correlated with adverse effects of administered anesthesia. Hybridization of the PNA probe is thus diagnostic for susceptibility to such effects.

Embodiments of the invention are also directed to detecting SNPs within a set of genes, methods of detection include but are not limited to, for example, use of SNP microarrays, gene chips, dynamic allele-specific hybridization, molecular beacons, restriction fragment length polymorphism (RFLP)-based methods, PCR-based methods, flap endonuclease-based methods, primer extension, 5'-nuclease-based methods, oligonucleotide ligase assays, single strand conformation polymorphism methods, temperature gradient gel electrophoresis, denaturing high performance liquid chromatography, high-resolution melting analysis, DNA mismatch-binding methods, capillary electrophoresis, and next-generation sequencing methods, and the like.

In embodiments of the invention, a test sample containing genomic DNA obtained from the subject is collected, and PCR is used to amplify a fragment comprising one or more markers or haplotypes of the present invention. As disclosed herein, identification of a particular marker allele or haplotype can be accomplished using a variety of methods (e.g. sequence analysis, analysis by restriction digestion, specific hybridization, single-stranded conformation polymorphism assays (SSCP), electrophoretic analysis, and the like). In some embodiments, diagnosis is accomplished by expression analysis, for example by using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s). Further, the expression of the variant(s) can be quantified as physically or functionally different.

In some embodiments, the DNA template can be amplified by means of whole genome amplification (WGA) methods prior to assessment for the presence of specific polymorphic markers as described herein. Standard methods well-known to the skilled person for performing WGA can be utilized and are within scope of the invention.

In some embodiments, analysis by restriction digestion can be used to detect a particular allele if the allele results in the creation or elimination of a restriction site relative to a reference sequence. RFLP analysis can be conducted, e.g. as described in *Current Protocols in Molecular Biology*, supra. The digestion pattern of the relevant DNA fragment indicates the presence or absence of the particular allele in the sample.

Sequence analysis can also be used to detect specific alleles or haplotypes. Accordingly, in some embodiments, determination of the presence or absence of a particular marker allele or haplotype comprises sequence analysis of a test sample of DNA or RNA obtained from a subject or individual. PCR or other appropriate methods can be used to amplify a portion of a nucleic acid that contains a polymorphic marker or haplotype, and the presence of specific alleles can then be detected directly by sequencing the polymorphic site (or multiple polymorphic sites in a haplotype) of the genomic DNA in the sample.

In some embodiments, arrays of oligonucleotide probes that are complementary to target nucleic acid sequence segments from a subject can be used to identify particular alleles at polymorphic sites. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light-directed synthesis methods that incorporate a combination of photolithographic methods and solid phase oligonucleotide synthesis methods, or by other methods known to the person skilled in the art (see, e.g., Bier, et al. *Adv Biochem Eng Biotechnol* 109:433-53 (2008); Hoheisel, J. D., *Nat Rev Genet.* 7:200-10 (2006); Fan, et al. *Methods Enzymol* 410:57-73 (2006); Raqoussis, J. and Elvidge, G., *Expert Rev Mol Diagn* 6:145-52 (2006); and Mockler, et al. *Genomics* 85:1-15 (2005), each of which is incorporated herein by reference in its entirety). Many additional descriptions of the preparation and use of oligonucleotide arrays for detection of polymorphisms can be found, for example, in U.S. Pat. Nos. 6,858,394, 6,429,027, 5,445,934, 5,700,637, 5,744,305, 5,945,334, 6,054,270, 6,300,063, 6,733,977, 7,364,858, EP 619 321, and EP 373 203, each of which is incorporated herein by reference in its entirety.

Other methods of nucleic acid analysis that are available to those skilled in the art can be used to detect a particular allele at a polymorphic site. Representative methods include, for example, direct manual sequencing (Church and Gilbert, *Proc. Natl. Acad. Sci. USA,* 81: 1991-1995 (1988); Sanger, et al., *Proc. Natl. Acad. Sci. USA,* 74:5463-5467 (1977); Beavis, et al., U.S. Pat. No. 5,288,644); automated fluorescent sequencing; single-stranded conformation polymorphism assays (SSCPs); clamped denaturing gel electrophoresis (CDGE); denaturing gradient gel electrophoresis (DGGE) (Sheffield, et al., *Proc. Natl. Acad. Sci. USA,* 86:232-236 (1989)), mobility shift analysis (Orita, et al., *Proc. Natl. Acad. Sci. USA,* 86:2766-2770 (1989)), restriction enzyme analysis (Flavell, et al., Cell, 15:25-41 (1978); Geever, et al., *Proc. Natl. Acad. Sci. USA,* 78:5081-5085 (1981)); heteroduplex analysis; chemical mismatch cleavage (CMC) (Cotton, et al., *Proc. Natl. Acad. Sci. USA,* 85:4397-4401 (1985)); RNase protection assays (Myers, et al., *Science,* 230:1242-1246 (1985); use of polypeptides that recognize nucleotide mismatches, such as *E. coli* mutS protein; and allele-specific PCR, and the like. One of skill in the art can recognize other techniques that can be used for these purposes.

In embodiments of the invention, a determination of a susceptibility or risk of developing adverse effects to administered anesthesia, analgesic, and/or opioid can be made by examining expression and/or composition of a polypeptide encoded by a nucleic acid associated with adverse effects to administered anesthesia in those instances where the genetic marker(s) or haplotype(s) as disclosed herein result in a change in the composition or expression of the polypeptide. Thus, determination of a susceptibility to developing adverse effects to administered anesthesia, analgesic, and/or opioid can be made by examining expression and/or composition of one of these polypeptides or another polypeptide encoded by a nucleic acid associated with development of adverse effects to administered anesthesia, in those instances where the genetic marker or haplotype of the present invention results in a change in the composition or expression of the polypeptide.

A variety of methods can be used for detecting protein expression levels, including, for example, enzyme linked immunosorbent assays (ELISA), Western blots, immunoprecipitations, and immunofluorescence, and the like. A test sample from a subject can be assessed for the presence of an alteration in the expression and/or an alteration in composition of the polypeptide encoded by a particular nucleic acid. An alteration in the expression of a polypeptide encoded by the nucleic acid can be, for example, an alteration in the quantitative polypeptide expression (i.e. the amount of polypeptide produced). An alteration in the composition of a polypeptide encoded by the nucleic acid is an alteration in the qualitative polypeptide expression (e.g. expression of a mutant polypeptide or of a different splicing variant). In some embodiments, determination of a susceptibility to developing adverse effects to administered anesthesia is carried out by detecting a particular splicing variant encoded by a nucleic acid associated with development of such adverse effects or a particular pattern of splicing variants.

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g. is from the same type of cells) and is from a subject who is not affected by and/or who does not have a susceptibility to development of adverse effects to administered anesthesia. In some embodiments, the control sample is from a subject that does not possess a marker allele or haplotype associated with development of adverse effects to administered anesthesia, as disclosed herein. Similarly, the presence of one or more different splicing variants in the test sample or the presence of significantly different amounts of different splicing variants in the test sample, as compared with the control sample, can be indicative of a susceptibility to developing adverse effects to administered anesthesia. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g. David et al., U.S. Pat. No. 4,376,110), such as immunoblotting (see, e.g., *Current Protocols in Molecular Biology*, particularly chapter 10, supra).

For example, in some embodiments, an antibody (e.g. an antibody with a detectable label) that is capable of binding to a polypeptide encoded by a nucleic acid associated with development of adverse effects to administered anesthesia can be used. Antibodies can be polyclonal or monoclonal. An intact antibody or a fragment thereof (e.g. Fv, Fab, Fab', F(ab')$_2$) can be used. The term "labeled," with regard to the probe or antibody, encompasses direct labeling of the probe or antibody by coupling (i.e. physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g. a fluorescently-labeled secondary antibody) and end-labeling of a DNA probe with biotin such that it can be detected with fluorescently-labeled streptavidin.

In some embodiments, the level or amount of a polypeptide in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid and is diagnostic for a particular allele or haplotype responsible for causing the difference in expression. Alternatively, the composition of the polypeptide in a test sample is compared with the composition of the polypeptide in a control sample. In some embodiments, both the level or amount and the composition of the polypeptide can be assessed in the test sample and in the control sample.

In some embodiments, determination of a susceptibility to developing adverse effects to administered anesthesia is made by detecting at least one marker or haplotype as disclosed herein, in combination with an additional protein-based, RNA-based, or DNA-based assay. In some embodiments, determination of a susceptibility to inadequate pain relief or sensitivity is made by detecting at least one marker or haplotype as disclosed herein, in combination with an additional protein-based, RNA-based, or DNA-based assay. In some embodiments, determination of a susceptibility to OSA is made by detecting at least one marker or haplotype as disclosed herein, in combination with an additional protein-based, RNA-based, or DNA-based assay. In some embodiments, determination of a susceptibility to developing adverse effects to administered anesthesia, analgesic, and/or opioid is made by determining incidence of OSA made by detecting at least one marker or haplotype as disclosed herein, in combination with an additional protein-based, RNA-based, or DNA-based assay.

In some embodiments, determination of a susceptibility to developing adverse effects to an administered opioid is made by detecting at least one marker or haplotype as disclosed herein, in combination with an additional protein-based, RNA-based, or DNA-based assay. In some embodiments, the administered opioid is morphine. In some embodiments, the administered opioid is codeine. In some embodiments, characterization of the OCT1 genotype is used to determine susceptibility to developing adverse effects to an administered opioid. In some embodiments, the UGT2B7 rs7438135 allele is determined. In some embodiments, the rs622342 allele is characterized.

Kits

Kits useful in the methods of the invention comprise components useful in any of the methods disclosed herein, including, for example, primers for nucleic acid amplification, hybridization probes, restriction enzymes (e.g. for RFLP analysis), allele-specific oligonucleotides, antibodies that bind to an altered polypeptide encoded by a nucleic acid as disclosed herein (e.g. a genomic segment comprising at least one polymorphic marker and/or haplotype of the present invention) or to a non-altered (native) polypeptide encoded by a nucleic acid of the invention as described herein, means for amplification of a nucleic acid associated with the development of adverse effects to administered anesthesia, means for analyzing the nucleic acid sequence of a nucleic acid associated with development of adverse effects to administered anesthesia, means for analyzing the amino acid sequence of a polypeptide encoded by a nucleic acid associated with development of adverse effects to administered anesthesia, and the like. The kits can, for example, include necessary buffers, nucleic acid primers for amplifying nucleic acids of the invention (e.g. a nucleic acid segment comprising one or more of the polymorphic markers as described herein), and reagents for allele-specific detection of the fragments amplified using such primers and necessary enzymes (e.g. DNA polymerase), and the like. Additionally, kits can provide reagents for assays to be used in combination with the methods as disclosed herein, e.g. reagents for use with other diagnostic assays for determining susceptibility to development of adverse effects to administered anesthesia. In some embodiments, reagents for performing WGA are included in the reagent kit.

In some embodiments, a kit for assaying a sample from a subject to detect a risk or susceptibility to developing adverse effects to administered anesthesia, analgesic, and/or opioid in a subject is provided, wherein the kit comprises reagents necessary for selectively detecting at least one allele of at least one polymorphism as disclosed herein in the genome of the individual. In some embodiments, the reagents comprise at least one contiguous oligonucleotide that hybridizes to a fragment of the genome of the individual comprising at least one polymorphism, as disclosed herein. In some embodiments, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism associated with developing adverse effects to administered anesthesia. In some embodiments, reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism associated with developing adverse effects to an administered opioid. In some embodiments, the polymorphism is selected from: ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKK1 rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, V158M rs4680, the CYP2D6*2, *2A, *3, *4, *5, *6, *7, *8, *9, *10,*11, *14, *15, *17, *18, *19, *20, *35, *40, *41, *42, and *44 alleles, the PGRN-Seq genetic markers (Table 16), and markers in linkage disequilibrium therewith. In some embodiments, the fragment is at least 20 base pairs in size. Such oligonucleotides or nucleic acids (e.g. oligonucleotide primers) can be designed using portions of the nucleic acid sequence flanking polymorphisms (e.g. SNPs or microsatellites) that are associated with a risk of developing adverse effects to administered anesthesia. In some embodiments, the kit comprises one or more labeled nucleic acids capable of allele-specific detection of one or more specific polymorphic markers or haplotypes, as well as reagents for detection of the label. Suitable labels include, e.g. a radio-isotope, a fluorescent label, an enzyme label, an enzyme co-factor label, a magnetic label, a spin label, an epitope label, and the like.

In some embodiments, the polymorphic marker or haplotype to be detected by the reagents of the kit comprises one or more markers, two or more markers, three or more markers, four or more markers, or five or more markers selected from the group consisting of: ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKK1 rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, the CYP2D6*2, *2A, *3, *4, *5, *6, *7, *8, *9, *10, *11, *14, *15, *17, *18, *19, *20, *35, *40, *41, *42, and *44 alleles, the PGRN-Seq genetic markers (Table 16), and markers in linkage disequilibrium therewith. In some embodiments, the marker or haplotype to be detected comprises one or more markers, two or more markers, three or more markers, four or more markers, or five or more markers selected from the group consisting of: the markers ABCB1 rs1045642 (ABCB1 C3435T), ABCB1 G2677T/A, ABCC3-211C>T rs4793665, ADRB2 rs1042717, ADRB2 rs1042714, ADRB2 rs1042713, ANKK1 rs1800497, DRD2 rs6279, FAAH rs4141964, FAAH rs2295632, FAAH rs3766246, FAAH rs324420, FAAH rs932816, FAAH rs324419, COMT rs6269, COMT rs4818, COMT rs4680 (COMT Val158Met), COMT rs4633, GCH1 rs 8007267, GCH1 rs752688, GCH1 rs4411417, OPRM1 A118G, CYP2D6, MDR1 rs1045642, MDR1 rs9282564, MDR1 rs1128503, MDR1 rs2032582, MDR1 rs2229109, OCT1 rs12208357, OCT1 rs34130495, OCT1 rs72552763, OCT1 rs34059508, TRPA1 rs1443952, TRPA1 rs13279503, TRPA1 rs13255063, TRPA1 rs1947913, UGT2B7 rs7439366, UGT2B7 rs7668258, V158M rs4680, the CYP2D6*2, *2A, *3, *4, *5, *6, *7, *8, *9, *10, *11, *14, *15, *17, *18, *19, *20, *35, *40, *41, *42, and *44 alleles, the PGRN-Seq genetic markers (Table 16), and markers in linkage disequilibrium therewith.

In certain embodiments, the kit further comprises a set of instructions for using the reagents comprising the kit.

Anesthetics and Analgesics

Embodiments of the invention are also directed to assessing patient response to anesthesia, anesthetics not limited to local anesthetics, general anesthetics, inhaled agents, intravenous agents, and muscle relaxants.

"Administered" anesthesia includes any anesthetic that is introduced to a subject, including, but not limited to, anesthesia that is administered orally, by dermal contact, subcutaneously, intravenously, by epidural means, spinally, and by inhalation.

Local anesthetics include, but are not limited to, benzocaine, chloroprocaine, cocaine, cyclomethycaine, dimethocaine/loracaine, piperocaine, propoxycaine, procaine/novocaine, proparacaine, tetracaine/amethocaine, articaine, bupivacaine, cinchocaine/dibucaine, etidocaine, levobupivacaine, lidocaine/lignocaine, mepivacaine, prilocaine, ropivacaine, trimecaine, saxitoxin, tetrodotoxin, menthol, eugenol, and combinations and derivations thereof.

General anesthetics include, but are not limited to, desflurane, enflurane, halothane, isoflurane, methoxyflurane, nitrous oxide, sevoflurane, xenon, amobarbital, methohexital, thiamylal, thiopental, diazepam, lorazepam, midazolam, etomidate, ketamine, propofol, alfentanil, fentanyl, remifentanil, sufentanil, buprenorphine, butorphanol, diamorphine, hydromorphone, levorphanol, meperidine, methadone, morphine, nalbuphine, oxycodone, oxymorphone, pentazocine, succinylcholine, decamethonium, mivacurium, rapacuronium, atracurium, cisatracurium, rocuronium, vecuronium, alcuronium, doxacurium, gallamine, metocurine, pancuronium, pipecuronium, tubocurarine, and combinations and derivations thereof.

Analgesics include, but are not limited to, opioids, such as morphine, fentanyl, hydromorphone, codeine, oxycodone, hydrocodone, tramadol, ondansetron, dexamethasone, methadone, alfentanil, remifentanil, and derivations thereof, and non-opioid analgesics, including acetaminophen, NSAIDs, dexmedetomidine, clonidine, and combinations and derivations thereof.

Adverse Anesthetic and Analgesic Effects

Adverse anesthetic effects can include, but are not limited to, inadequate pain relief, increased pain sensitivity, increased anesthesia and analgesic requirement, PONV, respiratory depression, excessive sedation, pruritus, death, and the like.

Genetic Indication for Codeine-Related Adverse Effects and Analgesia

As described herein, high CYP2D6 activity score was associated with increased adverse drug reactions (ADRs) (p=0.004) during post-operative days (POD) 0-2. Sedation after codeine was more common in girls (p=0.05). High pain intensity (p=0.003) and an interaction between CYP2D6 activity and time of the day after surgery (p=0.003) contributed to sedation risk. Pain reduction following a dose of codeine was associated with age (p=0.0002) and time (p=0.001) but not CYP2D6.

The results described herein, together with previous reports of codeine-related deaths and serious ADRs, demonstrate CYP2D6 association with codeine-related ADRs and sedation and indicate the potential safety hazards of using unpredictable and potentially life-threatening opioids that are also metabolized through the CYP2D6 pathway, such as codeine, hydrocodone, oxycodone, and tramadol. CYP2D6 testing prior to opioid administration is necessary to avoid codeine-, hydrocodone-, oxycodone-, or tramadol-related death and severe ADR risks, especially in young children and infants of breastfeeding mothers who have increased metabolic capacity to convert these opioids to their more potent metabolites. These should not be considered safe alternatives without CYP2D6 testing. An alternative approach to CYP2D6 testing is prescribing relatively safer non-opioid analgesics such as acetaminophen, non-steroidal anti-inflammatory drugs or appropriate and as needed doses of oral morphine in high-risk pediatric population.

Accordingly, embodiments of the invention are also directed to assessing a patient's risk of adverse response to opioids. In some embodiments, the patient's risk of adverse response to an opioid is assessed by CYP2D6 testing. In some embodiments, the opioid is codeine. In some embodiments, the opioid is, for example, hydrocodone, oxycodone, tramadol, or the like, or other commonly used medications used to prevent postoperative nausea and vomiting, such as, for example, ondansetron and dexamethasone, and the like.

In some embodiments, the patient at risk for an adverse response to an opioid is a child. In some embodiments, the patient at risk for an adverse response to an opioid is an infant.

Embodiments of the invention are also directed to adapting a treatment strategy for a patient requiring pain relief. In some embodiments, the patient's risk of adverse response to an opioid is assessed by CYP2D6 testing, and results of the risk assessment are used to make a decision regarding administration of an opioid. In some embodiments, an opioid is administered to a patient with low risk of adverse response to an opioid according to CYP2D6 testing. In some embodiments, an alternative therapeutic is administered to a patient with high risk of adverse response to an opioid according to CYP2D6 testing.

Having described the invention in detail, it will be apparent that modifications, variations, and equivalent embodiments are possible without departing from the scope of the invention defined in the appended claims. All examples in the present disclosure are provided as non-limiting examples.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Example 1

Genotypes Associated with Opioid-Related Adverse Effects

Figure 2:
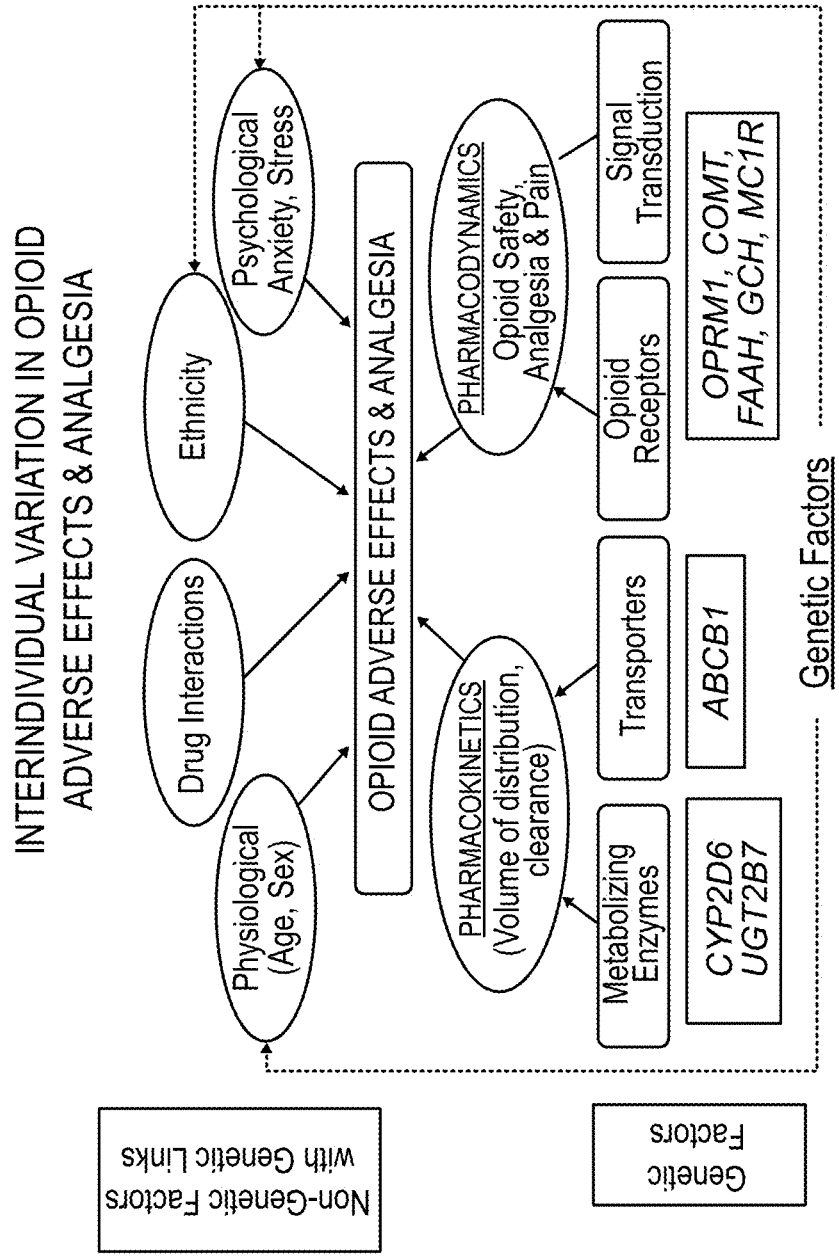
FIG. 2 depicts a schematic showing the genetic and non-genetic factors linked to inter-individual variation in opioid adverse effects and analgesia.

Individuals can have highly variable responses to opioids (FIG. 2). A perioperative morphine pharmacogenetic study of 150 children undergoing tonsillectomy revealed associations between genetic/non-genetic factors and postoperative opioid-related adverse effects and inadequate analgesia. The mean age of study participants was 9.25±2.65 years, the ratio of boys to girls was 47:53, the mean weight was 39.3±15.1 kg, the race ratio of white to non-white children was 81%:19%, and the ratio of children with obstructive sleep apnea (OSA) to those with no OSA was 46:54.

Figure 3:
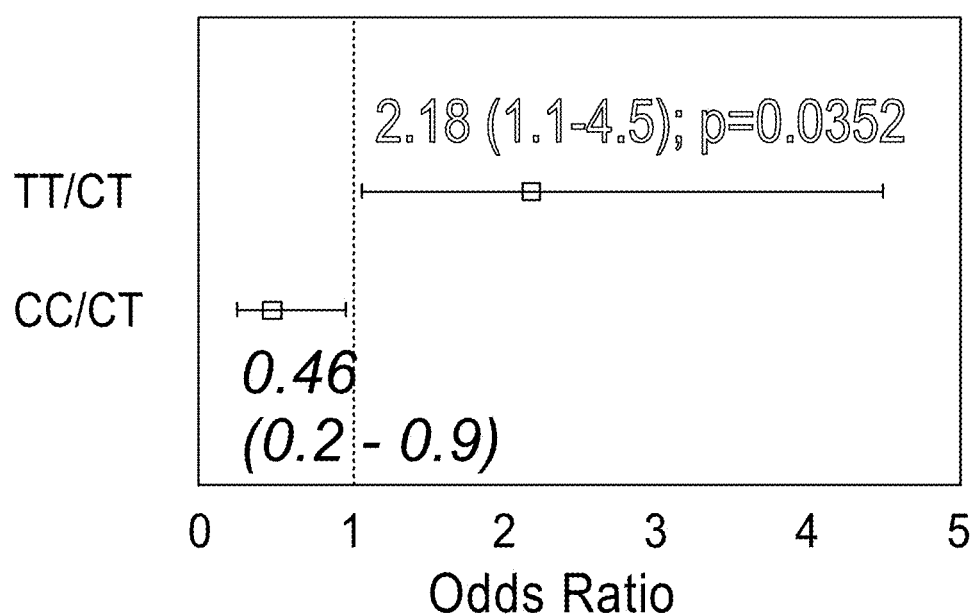
FIG. 3 depicts a graph illustrating the odds ratio of ABCB1 genotypes and respiratory depression in a post-anesthesia care unit (PACU) stay.
Figure 4:
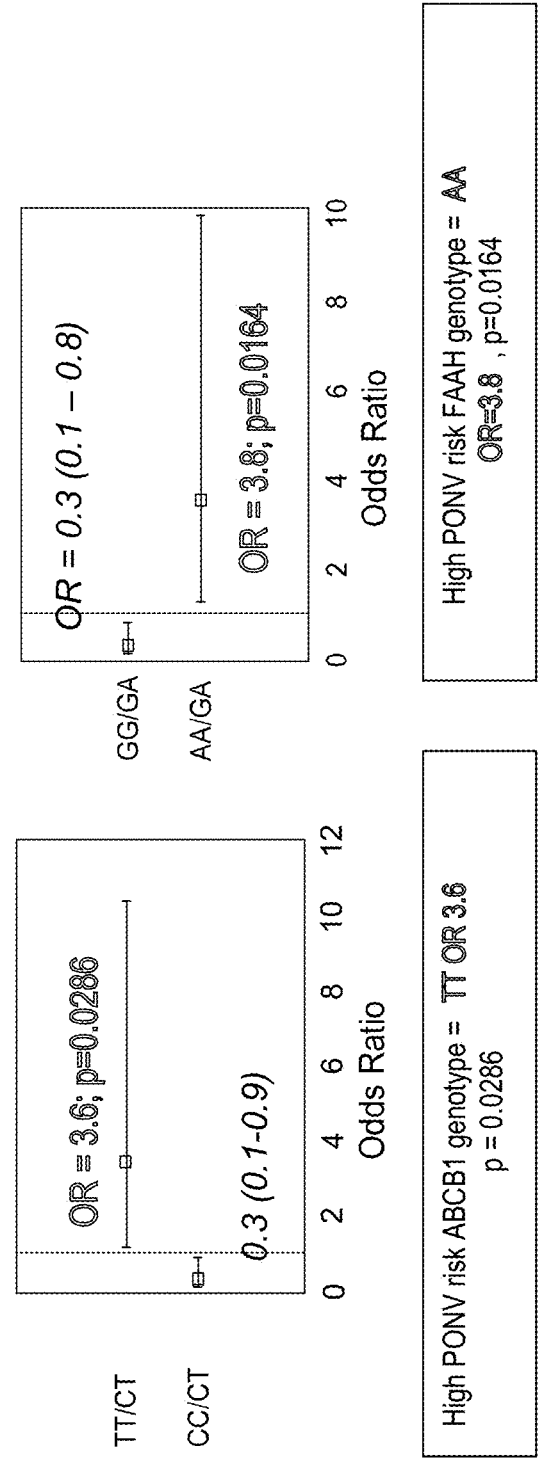
FIG. 4 depicts graphs showing the odds ratio of ABCB1 and FAAH genotypes and post-operative nausea and vomiting (PONV) in a PACU stay.
Figure 5A:
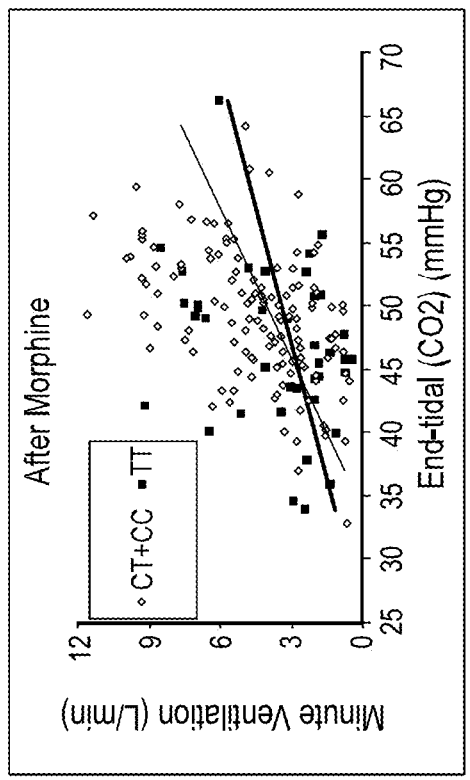
FIGS. 5A-5D depict scatterplots and graphs illustrating the varying respiratory responses of ABCB1 genotypes to 5% carbon dioxide.
Figure 5B:
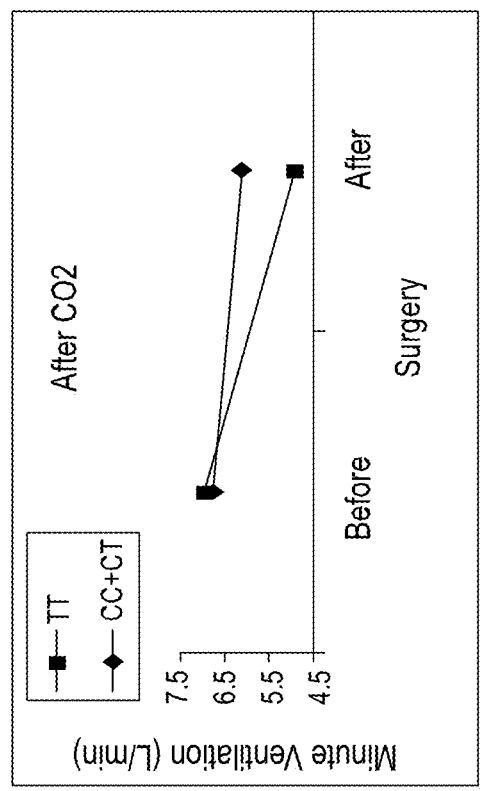
Figure 5C:
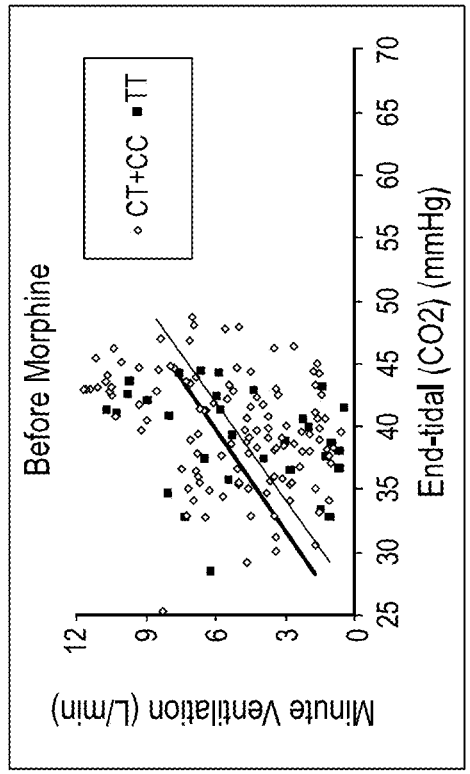
Figure 5D:
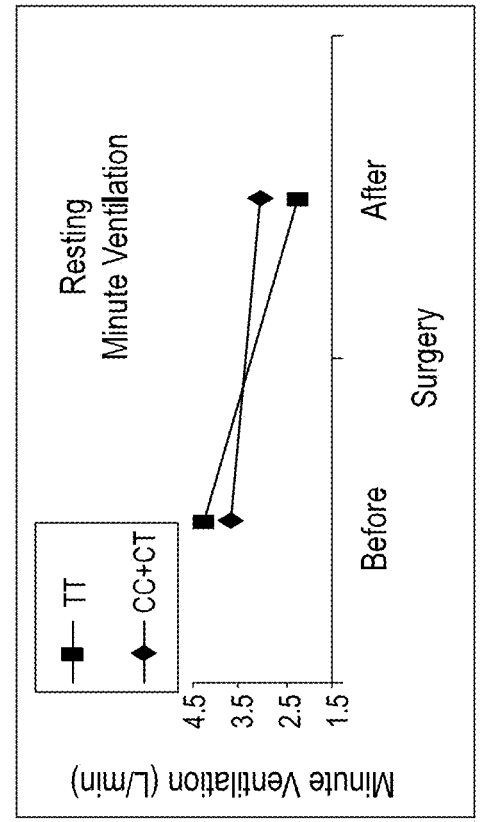

After adjusting for non-genetic risk factors such as OSA, the TT genotype of the ABCB1 SNP (rs1045642) was associated with higher risks of respiratory depression (OR=2.2, p=0.035) and PONV (OR=3.45, p=0.029) from morphine compared to the CT genotype (See Table 1 and FIG. 3). The CC genotype of ABCB1 was protective against respiratory depression (OR=0.46) and PONV (OR=0.29). The AA genotype of fatty acid amide hydrolase (FAAH) (rs4141964) is associated higher incidence of PONV (OR: 3.55, p=0.0164) compared to the GA genotype, and the GG genotype of FAAH is protective against PONV (See Table 2 and FIG. 4). There was an over ten-fold difference in the occurrence of opioid-induced PONV between high risk genotypes (TT of ABCB1 (rs1045642); AA of FAAH (rs4141964)) and low risk genotypes (CC of ABCB1 and GG of FAAH) (FIG. 4).

TABLE 1

| Genotype | PACU Incidence of Opioid Side Effects (N, %) | | | Prolonged PACU Stay (N, proportion) | | |
|---|---|---|---|---|---|---|
| ABCB1 rs1045642 | Respiratory Depression | Excessive Sedation | PONV | Respiratory Depression | Excessive Sedation | PONV |
| CC | 9 (21%) | 7 (18%) | 7 (17%) | 2 (5%) | 12 (28%) | 0 (0%) |
| CT | 17 (26%) | 13 (20%) | 7 (11%) | 9 (14%) | 22 (33%) | 4 (6%) |
| TT | 12 (29%) | 5 (14%) | 8 (20%) | 7 (17%) | 13 (32%) | 5 (12%) |

TABLE 2

| Genotype | PACU Incidence of Opioid Side Effects (N, %) | | | Prolonged PACU Stay (N, proportion) | | |
|---|---|---|---|---|---|---|
| FAAH rs4141964 | Respiratory Depression | Excessive Sedation | PONV | Respiratory Depression | Excessive Sedation | PONV |
| GG | 9 (16%) | 6 (11%) | 4 (7%) | 3 (5%) | 12 (21%) | 0 (0%) |
| GA | 20 (31%) | 16 (27%) | 12 (19%) | 9 (14%) | 26 (41%) | 5 (8%) |
| AA | 9 (30%) | 3 (11%) | 6 (20%) | 6 (20%) | 9 (30%) | 4 (13%) |

Example 2

Genotypic Association with Opioid-Induced Respiratory Depression

In the same perioperative morphine pharmacogenetic study (Example 1), it was observed that after exposure to morphine, the resting minute ventilation (MV) decreased by 47.5% in children with the ABCB1 TT genotype, compared to only 18.4% in those with the CC and CT genotypes (FIG. 5). The trend persisted after a 5% carbon dioxide challenge, as resting MV after morphine decreased 29% in children with the ABCB1 TT genotype, compared to 10% in those with the CC and CT genotypes (p<0.05) (FIG. 5). This further illustrates that the presence of the TT genotype of ABCB1 (rs1045642) is associated with development of adverse effects from administered anesthesia.

Example 3

Figure 6:
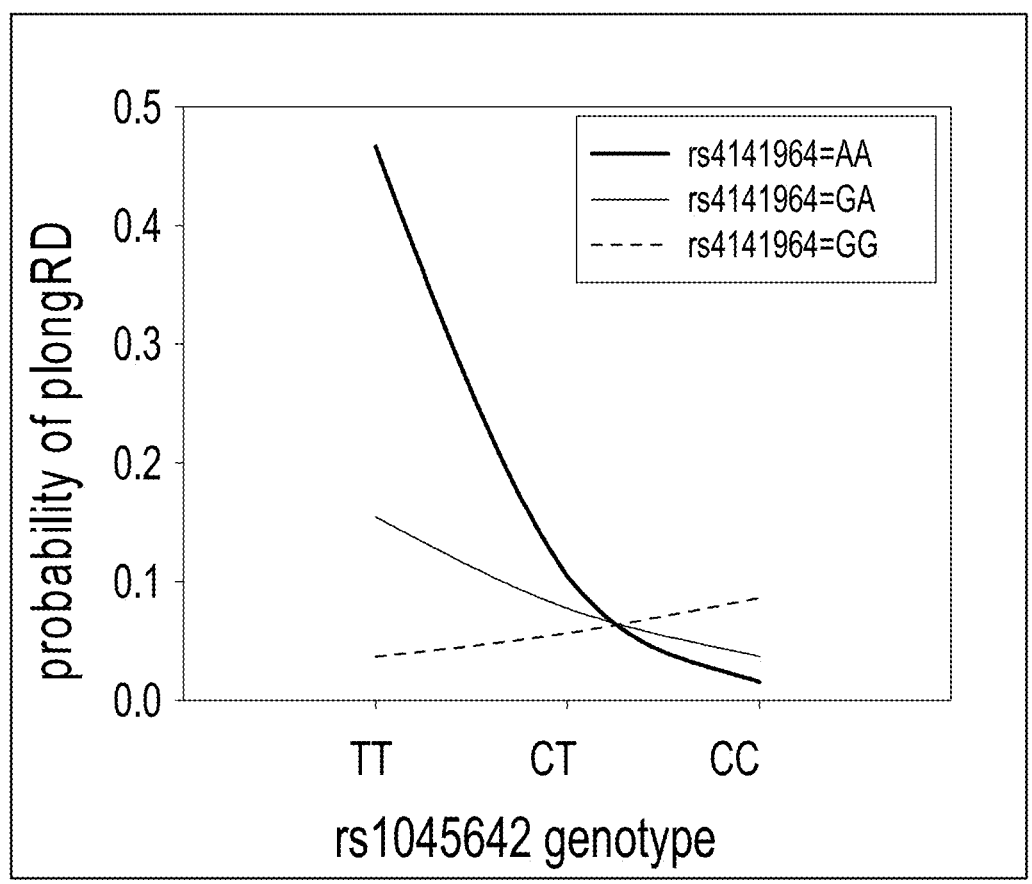
FIG. 6 depicts a plot showing the relationship between gene-gene (ABCB1 and FAAH) interactions and the probability of prolonged opioid-related respiratory depression.

Gene-Gene Interactions and Increased Risk of Opioid-Related Respiratory Depression In the same perioperative morphine pharmacogenetic study (Example 1), it was observed that, for children suffering from prolonged respiratory depression in the PACU, a significant interaction was detected between ABCB1 SNP (rs1045642) and FAAH SNP (rs4141964) (p=0.022). The probability of having the highest risk of respiratory depression (46.7%) is observed in the combination of TT and AA genotypes in ABCB1 (rs1045642) and FAAH (rs4141964), respectively (FIG. 6). The lowest probability of respiratory depression (1.5%) was observed in the combination of CC and AA genotypes in ABCB1 (rs1045642) and FAAH (rs4141964), respectively (p=0.022) (FIG. 6).

Example 4

Economic Burden of a Prolonged PACU Stay

The AA genotype of FAAH (rs4141964) was associated with longer PACU stays (143.8±14 minutes, or approximately USD $570), compared to GA (125.6±12.7 minutes, or approximately USD $480) and GG (112.5±10.8 minutes, or approximately USD $410) (p=0.0178). On average, children with AA genotypes stayed 24 minutes longer in the PACU than those with GG genotypes. This illustrates the need for creating and/or developing personalized anesthesia protocols in order to reduce development of adverse effects to administered anesthesia and consequently, hospital costs associated with caring for patients who suffer from such effects.

Example 5

Prolonged PACU Stays

In the same perioperative morphine pharmacogenetic study (Example 1), four SNPs of COMT had strong associations with pain scores, defined as maximum face, legs, activity, cry, and consolability (FLACC), morphine requirement, and analgesic interventions in the PACU (see Table 3).

TABLE 3

| COMT SNP | Genotype Frequency | $^a$Postoperative Pain (FLACC) mean ± SE | p-value | $^b$Total Morphine Use (mg/kg) mean ± SE | p-value | $^c$Postoperative Opioid Intervention OR (95% CI) | p-value |
|---|---|---|---|---|---|---|---|
| rs6269 | AA(49) | 2.1 ± 0.4 | 0.0205 | 0.23 ± 0.01 | 0.0124 | 0.30 (0.14-0.64) | 0.0017 |
|  | AG + GG(101) | 3.2 ± 0.3 |  | 0.25 ± 0.01 |  |  |  |
| rs4818 | CC (58) | 2.4 ± 0.4 | 0.1356 | 0.23 ± 0.01 | 0.1193 | 0.39 (0.19-0.79) | 0.0097 |
|  | CG + GG(92) | 3.1 ± 0.3 |  | 0.25 ± 0.01 |  |  |  |
| rs4680 | AA(38) | 2.2 ± 0.4 | 0.1139 | 0.23 ± 0.01 | 0.0568 | 0.32 (0.15-0.72) | 0.0053 |
|  | AG + GG(112) | 3.1 ± 0.3 |  | 0.25 ± 0.01 |  |  |  |
| rs4633 | TT (37) | 2.1 ± 0.4 | 0.0405 | 0.22 ± 0.01 | 0.0134 | 0.30 (0.13-0.67) | 0.0032 |
|  | TC + CC(113) | 3.1 ± 0.3 |  | 0.25 ± 0.01 |  |  |  |

$^a$adjusted for age, race and intra-operative morphine requirement
$^b$adjusted for race and intra-operative morphine requirement
$^c$adjusted for intra-operative morphine requirement Following a standard intraoperative morphine dose, patients with certain genotypes of COMT SNPs (AG and GG of rs6269; CG and GG of rs4818; AG and GG of rs4680 and TC and CC of rs4633) had higher surgical pain and were 3 times more likely to require analgesic interventions compared to other respective genotypes in the PACU (Table 3).

Example 6

Additional Genotypes Associated with Surgical Pain, Analgesia, and Opioid-Related Adverse Effects In the same study, but with a larger sample size, additional genotypes were subsequently identified for further stratification of African-American and Caucasian children. These genotypes can be associated with specific phenotypes, such as, for example, FLAAC scores, inadequate pain control with long PACU stays, need for opioid analgesic intervention in the PACU, need for post-operative analgesia in the PACU, opioid-related side effects leading to prolonged PACU stays, opioid-related side effects, respiratory depression, respiratory depression resulting in prolonged PACU stays, and post-operative vomiting resulting in prolonged PACU stays.

As shown in Table 4, a number of genotypes were strongly associated with outcomes. These include the T allele of UGT2B7 rs7439366 (A/T), which was strongly associated with maximum PACU FLACC scores for African-American children. In addition, the C allele of TRPA1 rs13279503 (C/G), the A allele of TRPA1 rs13255063 (A/T), and the G allele of MDR1 (ABCB1) rs9282564 (G/A) were strongly associated with inadequate pain control with long PACU stays for African-American children.

The G allele of COMT rs4818 (G/C) and the A allele of FAAH rs324419 (A/G) were strongly associated with a need for opioid analgesic intervention in the PACU for African-American children. The G allele of MDR1(ABCB1) rs9282564 (G/A) was also associated with opioid-related side effects leading to prolonged PACU stays for African-American children, as was the A allele of FAAH rs932816 (A/G). The A allele of MDR1 (ABCB1) rs2229109 (A/C) was strongly associated with opioid-related side effects for Caucasian children.

The T allele of GCH1 rs8007268 (T/C) and the A allele of ADRB2 rs1042717 (A/G) were both strongly associated with respiratory depression for African-American children.

TRPA1 rs1947913 (A/T), MDR1 (ABCB1) rs9282564 (G/A), and FAAH rs932816 (A/G) were all strongly associated with respiratory depression resulting in prolonged PACU stays. Of these, the A allele of TRPA1 rs1947913 was a risk factor for Caucasian children, the A allele of FAAH rs932816 was a risk factor for African-American children, and the G allele of MDR1(ABCB1) rs9282564 was a risk factor for both Caucasian and African-American children.

Four FAAH SNPs, namely rs2295632 (A/C), rs4141964 (A/G), rs3766246 (T/C), and rs324420 (A/C), were strongly associated with post-operative vomiting resulting in prolonged PACU stays. The A, A, T, and A alleles, respectively, were determined to be risk factors for Caucasian children.

TABLE 4

| Outcomes | SNP | Gene | Cohort | P-value | Minor/major allele | Risk allele | Effect size | Effect measure |
|---|---|---|---|---|---|---|---|---|
| Maximum PACU FLACC scores | rs1042713 | ADRB2 | Caucasian | 0.034 | A/G | A | 1.200934 | ratio of counts |
| | rs2032582 | MDR1(ABCB1) | Caucasian | 0.037 | AT/G | G | 0.837696 | ratio of counts |
| | rs8007267 | GCH1 | African-American | 0.035 | T/C | C | 0.817258 | ratio of counts |
| | rs1042713 | ADRB2 | interaction | 0.029 | A/G | | | |
| | rs1042714 | ADRB2 | combined | 0.046 | G/C | C | 0.865455 | ratio of counts |
| Maximum PACU FLACC scores zero-inflated | rs7439366 | UGT2B7 | African-American | 0.011 | A/T | T | 11.36002 | odds ratio |
| | rs1800497 | ANKK1 | Caucasian | 0.046 | T/C | T | 0.470246 | odds ratio |
| | rs7439366 | UGT2B7 | interaction | 0.032 | A/T | | | |
| Maximum PACU numerical rating scale | rs2295632 | FAAH | Caucasian | 0.034 | A/C | A | 0.6723 | mean difference |
| | rs4141964 | FAAH | Caucasian | 0.05 | A/G | A | 0.5889 | mean difference |
| | rs3766246 | FAAH | Caucasian | 0.035 | T/C | T | 0.6336 | mean difference |
| | rs1042713 | ADRB2 | Caucasian | 0.046 | A/G | A | 0.6577 | mean difference |
| | rs2032582 | MDR1(ABCB1) | African-American | 0.006 | AT/G | G | -3.5215 | mean difference |
| | rs4680 | COMT | African-American | 0.032 | A/G | G | -2.147 | mean difference |
| | rs8007267 | GCH1 | African-American | 0.043 | T/C | T | 1.6818 | mean difference |
| | rs2032582 | MDR1(ABCB1) | interaction | 0.004 | AT/G | | | |
| | rs4680 | COMT | interaction | 0.018 | A/G | | | |
| | rs324420 | FAAH | combined | 0.029 | A/C | A | 0.6744 | mean difference |
| Inadequate pain control with long PACU stay | rs1042713 | ADRB2 | Caucasian | 0.022 | A/G | A | 1.648227 | odds ratio |
| | rs13279503 | TRPA1 | African-American | 0.034 | C/G | C | 3.43941 | odds ratio |
| | rs13255063 | TRPA1 | African-American | 0.008 | A/T | A | 14.13424 | odds ratio |
| | rs9282564 | MDR1(ABCB1) | African-American | 0.029 | G/A | G | 9.042177 | odds ratio |
| | rs13255063 | TRPA1 | interaction | 0.023 | A/T | | | |
| | rs9282564 | MDR1(ABCB1) | interaction | 0.039 | G/A | | | |
| Opioid analgesic intervention need in PACU | rs1042713 | ADRB2 | Caucasian | 0.032 | A/G | A | 1.575701 | odds ratio |
| | rs4818 | COMT | African-American | 0.003 | G/C | G | 14.78333 | odds ratio |
| | rs6279 | DRD2 | African-American | 0.027 | C/G | G | 0.120308 | odds ratio |
| | rs324419 | FAAH | African-American | 0.006 | A/G | A | 43.0215 | odds ratio |
| | rs4818 | COMT | interaction | 0.008 | G/C | | | |
| | rs1800497 | ANKK1 | combined | 0.037 | T/C | T | 1.614782 | odds ratio |
| Postop analgesia in PACU | rs6269 | COMT | Caucasian | 0.022 | G/A | G | 1.280051 | count ratio |
| Postoperative morphine use | rs4141964 | FAAH | Caucasian | 0.015 | A/G | A | 0.0146 | mean difference |
| | rs3766246 | FAAH | Caucasian | 0.008 | T/C | T | 0.0158 | mean difference |
| | rs6269 | COMT | Caucasian | 0.03 | G/A | G | 0.0135 | mean difference |
| | rs4633 | COMT | Caucasian | 0.033 | T/C | C | -0.0135 | mean difference |
| | rs4818 | COMT | African-American | 4E-04 | G/C | C | -0.0477 | mean difference |
| | rs4818 | COMT | interaction | <0.0001 | G/C | | | |
| | rs6269 | COMT | interaction | 0.014 | G/A | | | |
| | rs4141964 | FAAH | interaction | 0.04 | A/G | | | |
| | rs2229109 | MDR1(ABCB1) | combined | 0.05 | A/C | C | -0.0354 | mean difference |
| Opioid side effects leading to prolonged PACU stay | rs2295632 | FAAH | Caucasian | 0.042 | A/C | A | 1.690966 | odds ratio |
| | rs4141964 | FAAH | Caucasian | 0.028 | A/G | A | 1.739504 | odds ratio |
| | rs3766246 | FAAH | Caucasian | 0.031 | T/C | A | 1.723919 | odds ratio |
| | rs6269 | COMT | African-American | 0.038 | G/A | A | 0.182246 | odds ratio |

TABLE 4-continued

| Outcomes | SNP | Gene | Cohort | P-value | Minor/major allele | Risk allele | Effect size | Effect measure |
|---|---|---|---|---|---|---|---|---|
| | rs9282564 | MDR1(ABCB1) | African-American | 0.049 | G/A | G | 12.9061 | odds ratio |
| | rs932816 | FAAH | African-American | 0.039 | A/G | A | 6.073287 | odds ratio |
| | rs932816 | FAAH | interaction | 0.012 | A/G | | | |
| | rs9282564 | MDR1(ABCB1) | combined | 0.015 | G/A | G | 2.429535 | odds ratio |
| Opioid-related side effects | rs2229109 | MDR1(ABCB1) | Caucasian | 0.034 | A/C | A | 5.401086 | odds ratio |
| | rs7668258 | UGT2B7 | Caucasian | 0.022 | T/C | T | 1.918992 | odds ratio |
| Respiratory depression | rs2295632 | FAAH | Caucasian | 0.034 | A/C | A | 1.764205 | odds ratio |
| | rs1128503 | MDR1(ABCB1) | Caucasian | 0.033 | T/C | C | 0.556549 | odds ratio |
| | rs8007267 | GCH1 | African-American | 0.006 | T/C | T | 6.621355 | odds ratio |
| | rs1042713 | ADRB2 | African-American | 0.044 | A/G | G | 0.379538 | odds ratio |
| | rs1042717 | ADRB2 | African-American | 0.036 | A/G | A | 2.823847 | odds ratio |
| | rs8007267 | GCH1 | interaction | 0.002 | T/C | | | |
| | rs1042713 | ADRB2 | interaction | 0.017 | A/G | | | |
| | rs1128503 | MDR1(ABCB1) | interaction | 0.029 | T/C | | | |
| | rs1042717 | ADRB2 | interaction | 0.048 | A/G | | | |
| | rs752688 | GCH1 | combined | 0.029 | T/C | C | 0.493417 | odds ratio |
| | rs4411417 | GCH1 | combined | 0.029 | C/T | T | 0.493417 | odds ratio |
| Respiratory depression resulting in prolonged PACU stay | rs13279503 | TRPA1 | Caucasian | 0.046 | C/G | C | 1.842273 | odds ratio |
| | rs1947913 | TRPA1 | Caucasian | 0.033 | A/T | A | 2.053612 | odds ratio |
| | rs9282564 | MDR1(ABCB1) | Caucasian | 0.002 | G/A | G | 3.724379 | odds ratio |
| | rs9282564 | MDR1(ABCB1) | African-American | 0.027 | G/A | G | 18.02032 | odds ratio |
| | rs932816 | FAAH | African-American | 0.043 | A/G | A | 5.743679 | odds ratio |
| | rs932816 | FAAH | interaction | 0.016 | A/G | | | |
| | rs1947913 | TRPA1 | interaction | 0.017 | A/T | | | |
| | rs324420 | FAAH | interaction | 0.034 | A/C | | | |
| Postoperative vomiting resulting in prolonged PACU stay | rs7668258 | UGT2B7 | Caucasian | 0.041 | T/C | C | 0.493072 | odds ratio |
| | rs2295632 | FAAH | Caucasian | 0.004 | A/C | A | 2.578738 | odds ratio |
| | rs4141964 | FAAH | Caucasian | 0.02 | A/G | A | 2.177767 | odds ratio |
| | rs3766246 | FAAH | Caucasian | 0.021 | T/C | T | 2.168856 | odds ratio |
| | rs324420 | FAAH | Caucasian | 0.039 | A/C | A | 2.021824 | |

Significance using p < 0.05

Example 7

Novel Fatty Acid Amide Hydrolase Genetic Variants Predict Postoperative Opioid-Induced Respiratory Depression, PONV, And Length of Hospital Stay Postoperative respiratory depression is a potentially life threatening, albeit preventable, complication of opioids. Inter-individual variability in adverse effect responses to opioids is a significant problem.

Fatty acid amide hydrolase (FAAH) is an important enzyme in the endocannabinoid pathway responsible for anandamide catabolism and has been hypothesized to influence variability in patient response to opioids. Accordingly, a study was designed to evaluate the influence of genetic variants of FAAH on perioperative opioid-related adverse effects in children.

A prospective, genotype-blinded observational study was conducted in order to evaluate the effect of genetic variants of FAAH on opioid-related adverse effects following tonsillectomy in children. A sample of 275 healthy children between 6 and 16 years of age were included. All participants received standard perioperative care with a standard anesthetic and an intraoperative dose of morphine. Opioid-related safety outcomes included incidences of respiratory depression and PONV leading to prolonged PACU stays. Reductions in ventilatory response to carbon dioxide (hypercapnic ventilatory response), the most sensitive and objective indicator of opioid induced respiratory depression (Pattinson K., Bowes M., et al. *Anaesthesia* 60:426-32 (2005)), were also compared between genetic variants.

Allelic frequencies of specific FAAH polymorphisms were significantly different between the African-American (n=44) and Caucasian (n=219) children studied. One specific FAAH SNP, namely rs2295632, demonstrated a significant association with opioid-induced respiratory depression (CC: 9.5%, AA: 15.4% and CA: 29.9%, p=0.034), PONV (CC: 10.3%, AA: 38.5% and CA: 18.2%, p<0.0001), and prolonged PACU stay (p=0.026). Postoperative minute ventilation (MV) and ventilatory response to carbon dioxide were significantly lower compared to preoperative baseline values; this MV reduction differed between FAAH genotypes (p=0.007), consistent with clinical respiratory depression (FIG. 7).

Similar doses of perioperative morphine in a homogenous pediatric population undergoing tonsillectomy resulted in different incidences and severity of opioid-induced respiratory depression, PONV, prolonged PACU stay due to opioid-related adverse effects and hypercapnic ventilatory responses. Based on the data provided herein, when managing children's pain, clinicians need to anticipate potentially higher incidences of opioid-induced respiratory depression and PONV in children with certain FAAH genetic variants.

Example 8

Non-Genetic Variations

Important non-genetic variations include: 1. Age (younger children are associated with higher pain scores), 2. Race (African Americans had more pain and inadequate analgesia; Caucasians had higher incidence of opioid adverse effects), 3. OSA (13-fold increased risk of respiratory depression (RD)), and 4. Morphine dose (0.1 mg/kg dose increase) increases risk for RD by 2.5-fold. Sex of the patient was shown in a subsequent study (Example 12) to be another important non-genetic factor contributing to outcome variations.

Example 9

Racial Differences in Perioperative Pain in Children

Out of 200 children prospectively recruited for a study, 34 were African American, and 160 were Caucasian. Age, weight, intra-operative morphine, and sex did not differ between black and white children (see Table 5). Postoperative pain, represented by postoperative opioid requirement, total analgesic use, FLACC pain scores, and analgesic interventions in the PACU, was higher in African American children than Caucasian children (p<0.005). Racial differences and predicted probabilities of postoperative morphine-induced adverse effects in children were determined (FIG. 8).

TABLE 5

Racial Differences in Perioperative Opioid Requirements in Caucasian and African American Children

|  | Black (N = 34) | White (N = 160) | p-value |
|---|---|---|---|
| Age (year) | 8.96 ± 2.42 | 9.23 ± 2.68 | 0.57 |
| Weight (kg) | 39.71 ± 15.60 | 38.27 ± 14.28 | 0.62 |
| Sex (% male) | 41.18% | 48.13% | 0.46 |
| Intraoperative morphine (mg/kg) | 0.19 ± 0.06 | 0.19 ± 0.06 | 0.79 |
| Postoperative morphine (mg/kg) | 0.11 ± 0.08 | 0.05 ± 0.06 | 0.0002 |
| Total perioperative morphine (mg/kg) | 0.30 ± 0.10 | 0.24 ± 0.08 | 0.0046 |

Example 10

Race and Unequal Burden of Perioperative Morphine Adverse Effects in Children Based on the statistics, Caucasian children had significantly higher opioid related adverse effects, including respiratory depression, PONV, and pruritus (odds ratio=2.8, p=0.0388). These data demonstrate that race is associated with surgical pain and opioid-related adverse effects.

The higher propensity for surgical pain experienced by African-American children and the higher propensity for adverse effects experienced by Caucasian children were subsequently validated in a larger study cohort containing 219 Caucasian children and 44 African American children. Results from this validation cohort are shown in Table 6, which presents race associations with analgesia and opioid-related adverse effect outcomes.

TABLE 6

| | | | Obstructive Sleep Apnea | | | | | |
|---|---|---|---|---|---|---|---|---|
| | | | No | | Yes | | all | |
| | | | Median (IQR) N (%) | P value | Median (IQR) N (%) | P value | Median (IQR) N (%) | P value |
| Intra-operative morphine (mg/Kg) | | AA | 0.20 (0.19-0.21) | 0.72 | 0.19 (0.14-0.20) | 0.18 | 0.20 (0.16-0.20) | 0.68 |
| | | CAU | 0.20 (0.19-0.24) | | 0.18 (0.12-0.20) | | 0.19 (0.17-0.21) | |
| Post-operative morphine (mg/Kg) | | AA | 0.10 (0.04-0.11) | 0.0217 | 0.10 (0.06-0.19) | <0.0001 | 0.10 (0.06-0.15) | <0.0001 |
| | | CAU | 0.05 (0.00-0.09) | | 0.04 (0.00-0.09) | | 0.05 (0.00-0.09) | |
| Maximum FLACC score | | AA | 3.50 (0.00-6.00) | 0.51 | 6.00 (4.00-8.25) | <0.0001 | 5.00 (3.25-8.00) | <0.0001 |
| | | CAU | 2.00 (0.00-5.00) | | 3.00 (0.00-6.00) | | 2.00 (0.00-5.00) | |
| Number of analgesic interventions | | AA | 1.00 (0.75-1.25) | 0.16 | 2.00 (1.00-2.25) | 0.0001 | 1.00 (1.00-2.00) | <0.0001 |
| | | CAU | 1.00 (0.00-1.00) | | 1.00 (0.00-1.00) | | 1.00 (0.00-1.00) | |
| Prolonged PACU stay due to pain | No | AA | 8 (57%) | 0.7713 | 9 (30%) | 0.0002 | 17 (39%) | 0.0006 |
| | | CAU | 79 (64%) | | 67 (71%) | | 146 (67%) | |
| | Yes | AA | 6 (43%) | | 21 (70%) | | 27 (61%) | |
| | | CAU | 45 (36%) | | 28 (29%) | | 73 (33%) | |
| Analgesic intervention needed in PACU | No | AA | 3 (21%) | 0.1540 | 2 (7%) | 0.0006 | 5 (11%) | 0.0001 |
| | | CAU | 54 (44%) | | 37 (39%) | | 91 (42%) | |
| | Yes | AA | 11 (79%) | | 28 (93%) | | 39 (89%) | |
| | | CAU | 70 (56%) | | 58 (61%) | | 128 (58%) | |
| Opioid-related side effects | No | AA | 3 (21%) | 0.4508 | 8 (28%) | 0.0337 | 11 (26%) | 0.0577 |
| | | CAU | 18 (15%) | | 10 (11%) | | 28 (13%) | |
| | Yes | AA | 11 (79%) | | 21 (72%) | | 32 (74%) | |
| | | CAU | 105 (85%) | | 85 (89%) | | 190 (87%) | |
| Opioid-related major side effects | No | AA | 8 (57%) | 0.1974 | 17 (61%) | 0.1452 | 25 (60%) | 0.0363 |
| | | CAU | 89 (75%) | | 71 (76%) | | 160 (76%) | |
| | Yes | AA | 6 (43%) | | 11 (39%) | | 17 (40%) | |
| | | CAU | 29 (25%) | | 22 (24%) | | 51 (24%) | |
| Opioid-related minor side effects | No | AA | 7 (54%) | 0.0155 | 10 (33%) | 0.0335 | 17 (40%) | 0.0041 |
| | | CAU | 26 (21%) | | 14 (15%) | | 40 (18%) | |
| | Yes | AA | 6 (46%) | | 20 (67%) | | 26 (60%) | |
| | | CAU | 97 (79%) | | 81 (85%) | | 178 (82%) | |
| RD | No | AA | 9 (64%) | 0.1403 | 22 (73%) | 0.3041 | 31 (70%) | 0.0922 |
| | | CAU | 103 (83%) | | 78 (82%) | | 181 (83%) | |

TABLE 6-continued

| | | | Obstructive Sleep Apnea | | | | | |
|---|---|---|---|---|---|---|---|---|
| | | | No | | Yes | | all | |
| | | | Median (IQR) N (%) | P value | Median (IQR) N (%) | P value | Median (IQR) N (%) | P value |
| | Yes | AA | 5 (36%) | | 8 (27%) | | 13 (30%) | |
| | | CAU | 21 (17%) | | 17 (18%) | | 38 (17%) | |
| ES | No | AA | 10 (71%) | 0.0684 | 23 (82%) | 0.3115 | 33 (79%) | 0.0628 |
| | | CAU | 106 (90%) | | 83 (90%) | | 189 (90%) | |
| | Yes | AA | 4 (29%) | | 5 (18%) | | 9 (21%) | |
| | | CAU | 12 (10%) | | 9 (10%) | | 21 (10%) | |
| PONV | No | AA | 14 (100%) | 0.2148 | 27 (90%) | 0.4006 | 41 (93%) | 0.1600 |
| | | CAU | 106 (85%) | | 77 (81%) | | 183 (84%) | |
| | Yes | AA | 0 (0%) | | 3 (10%) | | 3 (7%) | |
| | | CAU | 18 (15%) | | 18 (19%) | | 36 (16%) | |
| Pruritus | No | AA | 7 (54%) | 0.0468 | 12 (40%) | 0.0505 | 19 (44%) | 0.0074 |
| | | CAU | 31 (25%) | | 19 (20%) | | 50 (23%) | |
| | Yes | AA | 6 (46%) | | 18 (60%) | | 24 (56%) | |
| | | CAU | 92 (75%) | | 75 (80%) | | 167 (77%) | |
| Prolonged PACU stay due to opioid side effects | No | AA | 7 (50%) | 0.2503 | 21 (70%) | 0.8248 | 28 (64%) | 0.8624 |
| | | CAU | 82 (66%) | | 62 (65%) | | 144 (66%) | |
| | Yes | AA | 7 (50%) | | 9 (30%) | | 16 (36%) | |
| | | CAU | 42 (34%) | | 33 (35%) | | 75 (34%) | |
| Prolonged PACU stay due to major opioid side effects | No | AA | 7 (50%) | 0.2268 | 21 (70%) | 1.0000 | 28 (64%) | 0.4761 |
| | | CAU | 86 (69%) | | 67 (71%) | | 153 (70%) | |
| | Yes | AA | 7 (50%) | | 9 (30%) | | 16 (36%) | |
| | | CAU | 38 (31%) | | 28 (29%) | | 66 (30%) | |
| Prolonged RD | No | AA | 11 (79%) | 0.2085 | 27 (90%) | 1.0000 | 38 (86%) | 0.6057 |
| | | CAU | 111 (90%) | | 84 (88%) | | 195 (89%) | |
| | Yes | AA | 3 (21%) | | 3 (10%) | | 6 (14%) | |
| | | CAU | 13 (10%) | | 11 (12%) | | 24 (11%) | |
| Prolonged ES | No | AA | 9 (64%) | 0.5469 | 22 (73%) | 1.0000 | 31 (70%) | 0.8549 |
| | | CAU | 89 (72%) | | 69 (73%) | | 158 (72%) | |
| | Yes | AA | 5 (36%) | | 8 (27%) | | 13 (30%) | |
| | | CAU | 35 (28%) | | 26 (27%) | | 61 (28%) | |
| Prolonged PONV | No | AA | 14 (100%) | 1.0000 | 30 (100%) | 0.1159 | 44 (100%) | 0.0499 |
| | | CAU | 116 (94%) | | 85 (89%) | | 201 (92%) | |
| | Yes | AA | 0 (0%) | | 0 (0%) | | 0 (0%) | |
| | | CAU | 8 (6%) | | 10 (11%) | | 18 (8%) | |

Note:
Continuous variables were shown as median (IQR), and were compared using Wilcoxon rank-sum test: categorical variables were shown as number (proportion) and were compared using Fisher's Exact test.
AA: African-American:
CAU: Caucasian.
PACU: Post Anesthesia Recovery Unit,
RD: Respiratory Depression,
PONV: Post-Operative Nausea and Vomiting

Example 11

OSA Association with Increased Post-Operative Pain in Children

The same validation study cohort containing 219 Caucasian children and 44 African American children (Example 10) was used to determine the influence of OSA on peri- and post-operative pain. OSA in children was found to be associated with increased post-operative pain, as shown in Table 7. African-American and Caucasian children with OSA experienced higher post-operative FLAAC pain scores. In addition, African-American children with OSA experienced a greater need for prolonged PACU stays due to pain and analgesic interventions in the PACU.

TABLE 7

| | | | Race | | | | | |
|---|---|---|---|---|---|---|---|---|
| | | | African-Americans | | Caucasians | | All races | |
| | | OSA | Median (IQR) N (%) | P value | Median (IQR) N (%) | P value | Median (IQR) N (%) | P value |
| Intra-operative morphine (mg/kg) | | No | 0.20 (0.19-0.21) | 0.11 | 0.20 (0.19-0.24) | <0.0001 | 0.20 (0.19-0.23) | <0.0001 |
| | | Yes | 0.19 (0.14-0.20) | | 0.18 (0.12-0.20) | | 0.19 (0.13-0.20) | |
| Post-operative morphine (mg/kg) | | No | 0.10 (0.04-0.11) | 0.09 | 0.05 (0.00-0.09) | 0.71 | 0.05 (0.00-0.09) | 0.07 |
| | | Yes | 0.10 (0.06-0.19) | | 0.04 (0.00-0.09) | | 0.05 (0.00-0.10) | |

TABLE 7-continued

| | | | Race | | | | | |
|---|---|---|---|---|---|---|---|---|
| | | | African-Americans | | Caucasians | | All races | |
| | | OSA | Median (IQR) N (%) | P value | Median (IQR) N (%) | P value | Median (IQR) N (%) | P value |
| Maximum post-operative FLACC pain scores in PACU | | No | 3.50 (0.00-6.00) | 0.0116 | 2.00 (0.00-5.00) | 0.19 | 2.00 (0.00-5.00) | 0.0025 |
| | | Yes | 6.00 (4.00-8.25) | | 3.00 (0.00-6.00) | | 4.00 (1.00-6.00) | |
| Total peri-operative analgesia | | No | 1.00 (0.75-1.25) | 0.0525 | 1.00 (0.00-1.00) | 0.31 | 1.00 (0.00-1.00) | 0.0157 |
| | | Yes | 2.00 (1.00-2.25) | | 1.00 (0.00-1.00) | | 1.00 (0.00-2.00) | |
| Prolonged PACU stay due to pain | No | No | 8 (47%) | 0.11 | 79 (54%) | 0.31 | 87 (53%) | 0.80 |
| | No | Yes | 9 (53%) | | 67 (46%) | | 76 (47%) | |
| | Yes | No | 6 (22%) | | 45 (62%) | | 51 (51%) | |
| | Yes | Yes | 21 (78%) | | 28 (38%) | | 49 (49%) | |
| Analgesic intervention needed in PACU | No | No | 3 (60%) | 0.31 | 54 (59%) | 0.58 | 57 (59%) | 0.10 |
| | No | Yes | 2 (40%) | | 37 (41%) | | 39 (41%) | |
| | Yes | No | 11 (28%) | | 70 (55%) | | 81 (49%) | |
| | Yes | Yes | 28 (72%) | | 58 (45%) | | 86 (52%) | |

Example 12

Unequal Burden and Higher Incidence of Opioid-Related Adverse Effects in Caucasian Girls Undergoing Surgery Unpredictable inter-individual variations in responses to perioperative opioids result in inadequate analgesia and excessive opioid-related adverse effects. Race of children is associated with an unequal burden of surgical pain and opioid-related adverse effects; African-American children experience disproportionally more postoperative pain, and Caucasian children experience higher incidences of opioid-related adverse effects with similar doses of opioids (Examples 9, 10, and 11; Sadhasivam S., et al. *Pediatrics*, 129: 832-8 (2012)). The effects of gender on opioid responses in children have heretofore not been well studied. Accordingly, a large prospective study was designed in order to determine the effects of sex on perioperative opioid-related adverse effects in children.

In this prospective observational study, 275 children between 6 and 16 years of age undergoing outpatient tonsillectomy were recruited. All participants received standard perioperative care with a standard intraoperative dose of morphine. Opioid-related safety outcomes included incidences of respiratory depression, excessive sedation, PONV, and incidence of prolonged PACU stays due to opioid-related adverse effects. Total perioperative (intraoperative and postoperative) morphine was correlated with the probability of opioid-related adverse effects in girls versus boys.

Figure 9B:
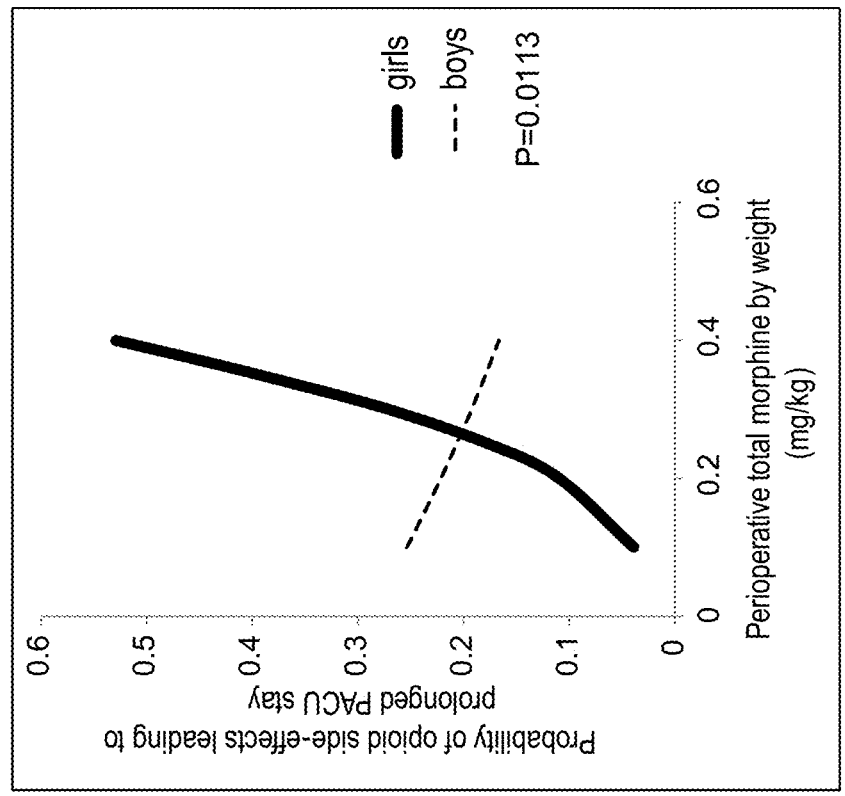
FIGS. 9A-9B depict the higher incidence of adverse effects experienced by Caucasian girls.
Figure 9A:
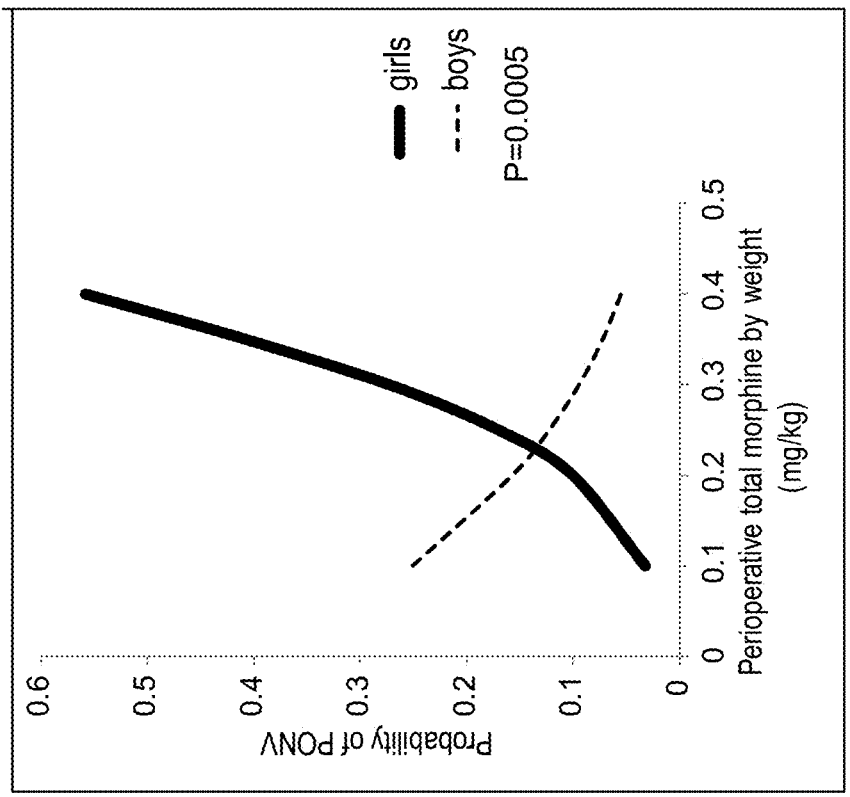

Due to relatively smaller sample sizes of non-Caucasian children (44 African-Americans and 12 other races), the study focused on 219 Caucasian children (114 girls and 105 boys). Though mean age and weight were comparable, Caucasian girls had higher incidence of OSA (50% vs. 36%, p=0.04). Caucasian girls had significantly higher PONV (p=0.01) and prolonged PACU stays due to opioid-related adverse effects (p=0.002) than Caucasian boys. The probability of PONV (p=0.0005) and prolonged PACU stay due to opioid-related adverse effects (p=0.0113) increased as total dose of morphine increased in Caucasian girls; while they decreased in Caucasian boys (FIGS. 9A-B). Though incidence of PONV and opioid-related adverse effects were greater in younger pre-pubertal Caucasian girls (<9 years) than older Caucasian girls (≥9 years), the differences were not statistically significant.

This prospective study of a homogeneous surgical population demonstrates that Caucasian girls have an unequal burden of high incidences of PONV and prolonged PACU stays due to opioid-related adverse effects as compared to boys. Though adult women have higher incidences of PONV attributed to the effects of estrogen, such hormonal effects were not observed when comparing pre-pubertal to post-pubertal Caucasian girls. These results demonstrate that sex is an underlying mechanism which influences opioid-related adverse effects following surgery in children. When managing children's pain, clinicians need to anticipate potentially higher PONV and adverse effects in young Caucasian girls for similar doses of morphine as compared to boys.

Example 13

Age-Related Maturational Differences in the Pharmacokinetic Data

Preliminary results from 146 children from Cincinnati alone indicate that there are age-related maturational differences in the pharmacokinetics of morphine in children between 6 and 15 years of age. In a follow-up study, the maturational differences in the pharmacokinetics of morphine are quantified, and the role of the UGT2B7 gene on maturation of this main morphine metabolic pathway is studied. An integrated PK-PG-PD model linking morphine concentration to analgesic efficacy and adverse effects, along with model-based simulations, can be performed to derive personalized dosing for morphine across the entire range of the pediatric population.

Example 14

Morphine Clearance and Age

Figure 10:
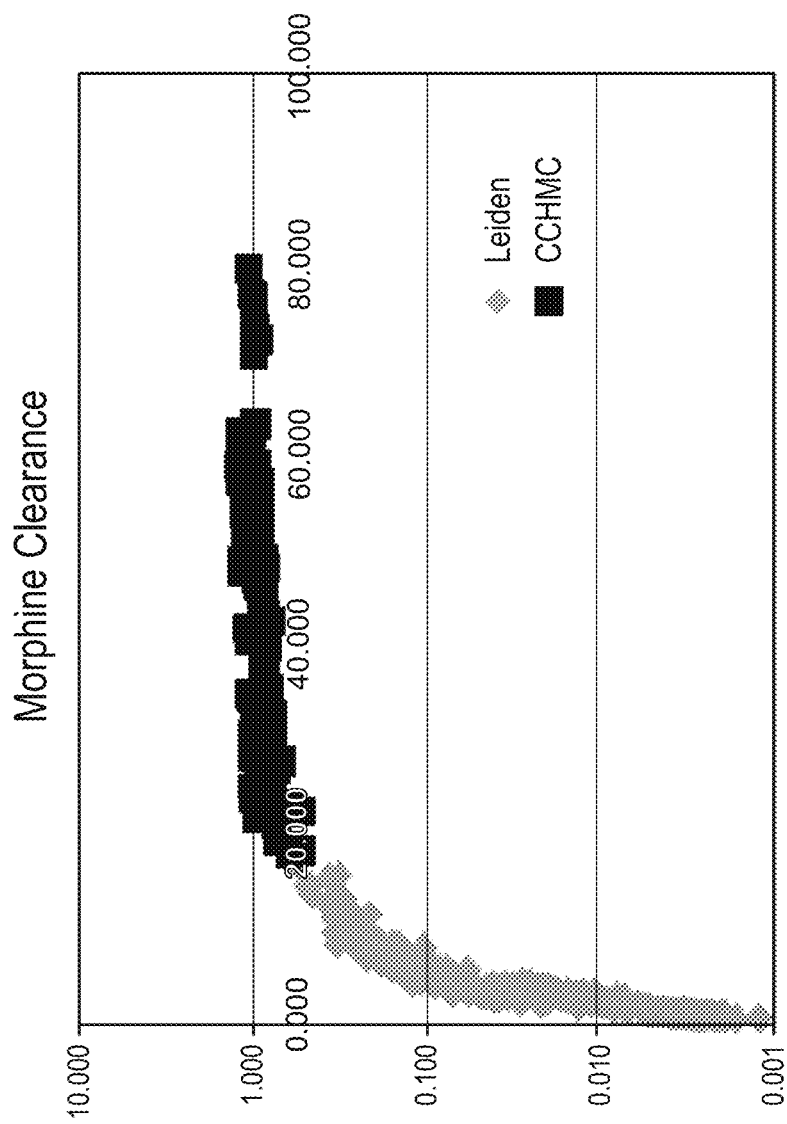
FIG. 10 depicts a scatterplot comparing morphine clearance in CCHMC data of children (6-15 years of age) and previously published data from Leiden (less than 3 years of age).

Maturation and age (clearance versus body weight)-related changes in morphine clearance were observed in children. When the data of children (6-15 years of age) from Cincinnati Children's Hospital Medical Center were compared with previously published data from Leiden (Krekels, et al., *Clin. Pharmacokinet.* 50(1):51-63 (2011)) on younger children (less than 3 years of age) receiving morphine, older children were observed to experience higher morphine clearance (FIG. 10). This indicates that age can be an additional factor to consider in addition to the presence or absence of certain genetic markers for evaluation of a patient's risk of developing adverse effects from administered anesthesia.

Example 15

Race and Differential Clearance of Morphine

Figure 11:
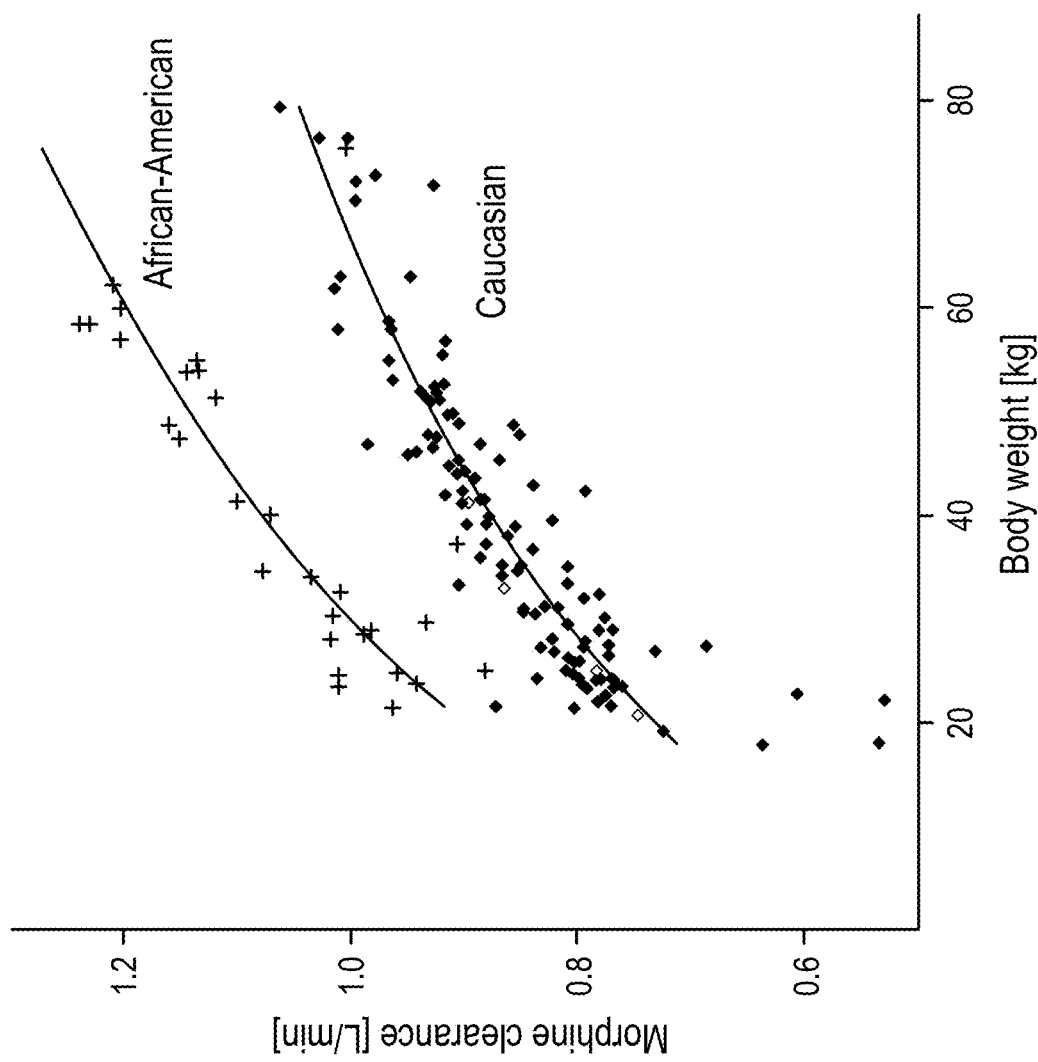
FIG. 11 depicts a scatterplot showing the clearance of morphine in African-American children (stars) and Caucasian children (diamonds).
Figure 12:
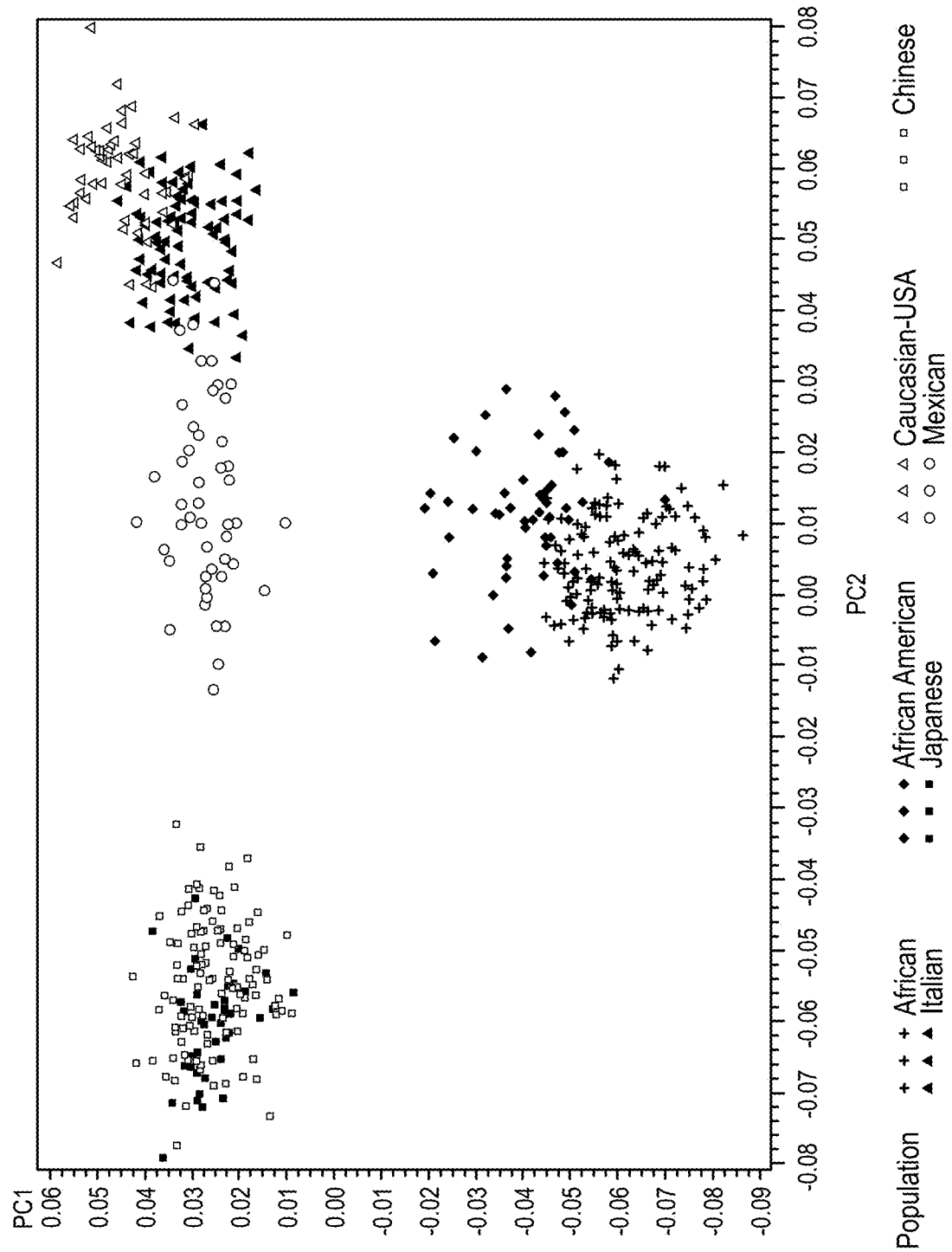
FIG. 12 depicts a scatterplot illustrating the relationship between genetic markers and population stratification.

Pharmacokinetic analysis of 146 children who had undergone a tonsillectomy procedure demonstrated that African American children had approximately 25% higher clearance of morphine (clearance factor is 1.23 for African American children) than Caucasian children (FIG. 11). In FIG. 11, the symbols represent individual children in the study, while lines represent population averages. The stars and the accompanying line represent predictions for African-American individuals; the triangles and the accompanying solid line represent predictions for the Caucasian individuals, as well as individuals of other descent. FIG. 12 depicts the relationship between genetic markers and population stratification.

Example 16

OCT1 Polymorphisms are Associated with Lowered Intravenous Morphine Pharmacokinetic Clearance Many endogenous and exogenous compounds, including drugs, are eliminated from the body by the liver via metabolism and/or excretion. Although the metabolic aspects of hepatic clearance have been the focus of research for several decades, the important role of hepatic transport systems in the hepatobiliary disposition of drugs and metabolites has been recognized only recently.

These systems are aided by the family of SLC22 transporters, which are expressed in the intestine, liver, and kidney and therefore play a pivotal role in drug absorption and excretion (Koepsell, H. et al. *Pflugers Arch.* 447:666-76 (2004)). The SLC22 transporter family comprises organic cation transporters (OCTs), zwitterion/cation transporters (OCTNs), and organic anion transporters (OATs). Most transporters of the SLC22 family are polyspecific, i.e., they transport multiple different substrates; in addition, numerous other ligands can act as inhibitors. The SLC22 family can be divided into various subgroups according to substrates and transport mechanisms. One subgroup comprises the OCT subtypes 1-3. which translocate organic cations, including weak bases.

The organic cation transporter 1 (OCT1, with alternative gene name SLC22A1) is a member of the SLC22A transporter family that is predominantly expressed in the sinusoidal membrane of the human liver (Nies, A. et al. *Hepatology* 50:1227-40 (2009); Gorboulev, V. et al. *DNA Cell. Biol.* 16: 871-81 (1997); Zhang, L. et al. *Mol. Pharmacol.* 51:913-21 (1997)). OCT1 is a trans-membrane protein driven by membrane potential. Typical OCT1 substrates include TEA, MMP$^+$, metformin, cimetidine, and guinidine; quinidine is a typical OCT1 inhibitor. There is large interindividual variability in the expression of OCT1 protein (83-fold) and mRNA (115-fold) in the human liver.

OCT1 is highly genetically polymorphic, as about 10% of Caucasians are compound homozygous carriers of one of the five common coding polymorphisms, namely Arg61Cys, Cys88Arg, Gly401Ser, Gly465Arg, and deletion of Met420 (Tzvetkov, M. et al. ACSPT abstract (2012)). These are listed in Table 8.

TABLE 8

| Haplotype | Codon | | | | | | Allele Freq. (%) | |
|---|---|---|---|---|---|---|---|---|
| | 61 | 88 | 401 | 420 | 465 | | | |
| OCT1*1 | Arg | Cys | Gly | Met | Gly | Active | 70.1 | |
| OCT1*2 | Arg | Cys | Gly | del | Gly | Deficient | 14.8 | |
| OCT1*3 | Cys | Cys | Gly | Met | Gly | Deficient | 10.1 | |
| OCT1*4 | Arg | Cys | Ser | Met | Gly | Deficient | 2.4 | 29.7 |
| OCT1*5 | Arg | Cys | Gly | del | Arg | Deficient | 1.8 | |
| OCT1*6 | Arg | Arg | Gly | del | Gly | Deficient | 0.6 | |

The frequency of these polymorphisms varies with different ancestries (Shu et al. *Proc. Natl. Acad. U.S.A.* 100: 5902-7 (2003)). These polymorphisms result in the reduced ability of the liver to take up drugs, such as metformin, tropisetron, or O-desmethyltramadol (Kerb, R. et al. *Pharmacogenetics* 12:591-5 (2002); Shu, Y. et al. *J. Clin. Invest.* 117:1422-31 (2007); Tzvetkov, M. et al. *Pharmacogenomics J.* 12:22-9 (2012); Tzvetkov, M. et al. *Clin. Pharmacol. Ther.* 90: 143-50 (2011)). Reports have demonstrated that morphine is a substrate of OCT1, and carriers of the loss-of-function OCT1 gene polymorphisms listed above have increased plasma concentrations of morphine in adult healthy volunteers (Tzvetkov, M. et al. *Clin. Pharmacol. Ther.* 91:S105(2012)).

OCT1 genotyping revealed the association of SNPs in the mRNA that correspond to the known OCT1 polymorphisms listed previously. All alleles (amino acid substitutions) were assumed to present independently. These results are summarized in Table 9.

TABLE 9

| | SNPs | | | | |
|---|---|---|---|---|---|
| | rs12208357 | rs34130495 | rs72552763 | rs34059508 | |
| mRNA | 286C > T | 1306G > A | 1365GAT > del | 1498G > C | |
| Amino acid location | 61 | 401 | 420 | 465 | |
| OCT1*1 (reference) | Arg | Gly | Met | Gly | Active |
| OCT1*2 | Arg | Gly | del | Gly | Deficient |
| OCT1*3 | Cys | Gly | Met | Gly | Deficient |
| OCT1*4 | Arg | Ser | Met | Gly | Deficient |
| OCT1*5 | Arg | Gly | del | Arg | Deficient |

According to the number of alleles (*2-*5), 140 patients were then classified into three groups, with 0, 1, or 2 defective alleles, according to the following classification strategy:
Group 0: *1/*1
Group 1: *1/*2, *1/*3, *1/*4, *1/*5
Group 2: *2/*2, *2/*3, *2/*4, *2/*5, *3/*3, *3/*4, *3/*5, *4/*4, *4/*5, *5/*5

This classification resulted in the patient distribution shown in Table 10.

TABLE 10

| Groups | Number | Mean | SD |
| --- | --- | --- | --- |
| 0 (wild) | 80 | 0.570 | 0.059 |
| 1 (hetero) | 51 | 0.579 | 0.060 |
| 2 (homo) | 9 | 0.517* | 0.049 |

*P < 0.05 vs 0 and 1 (non-parametric)

Figure 13:
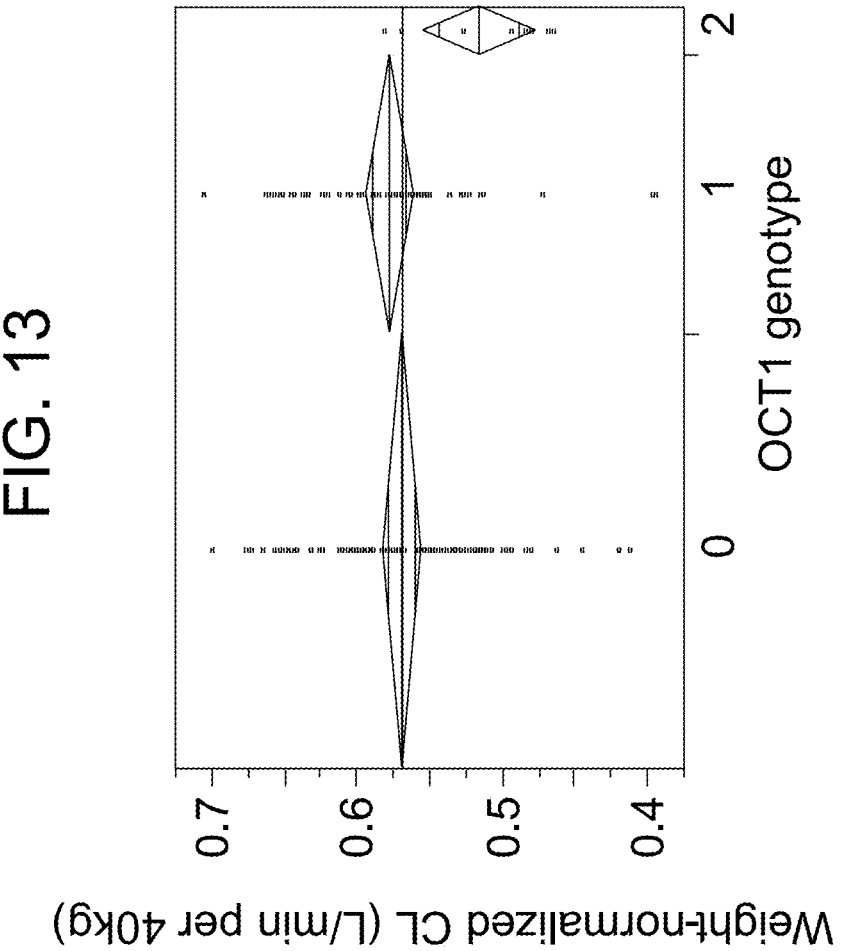
FIG. 13 depicts weight-normalized morphine clearance for OCT1 genotypes.
Figure 14:
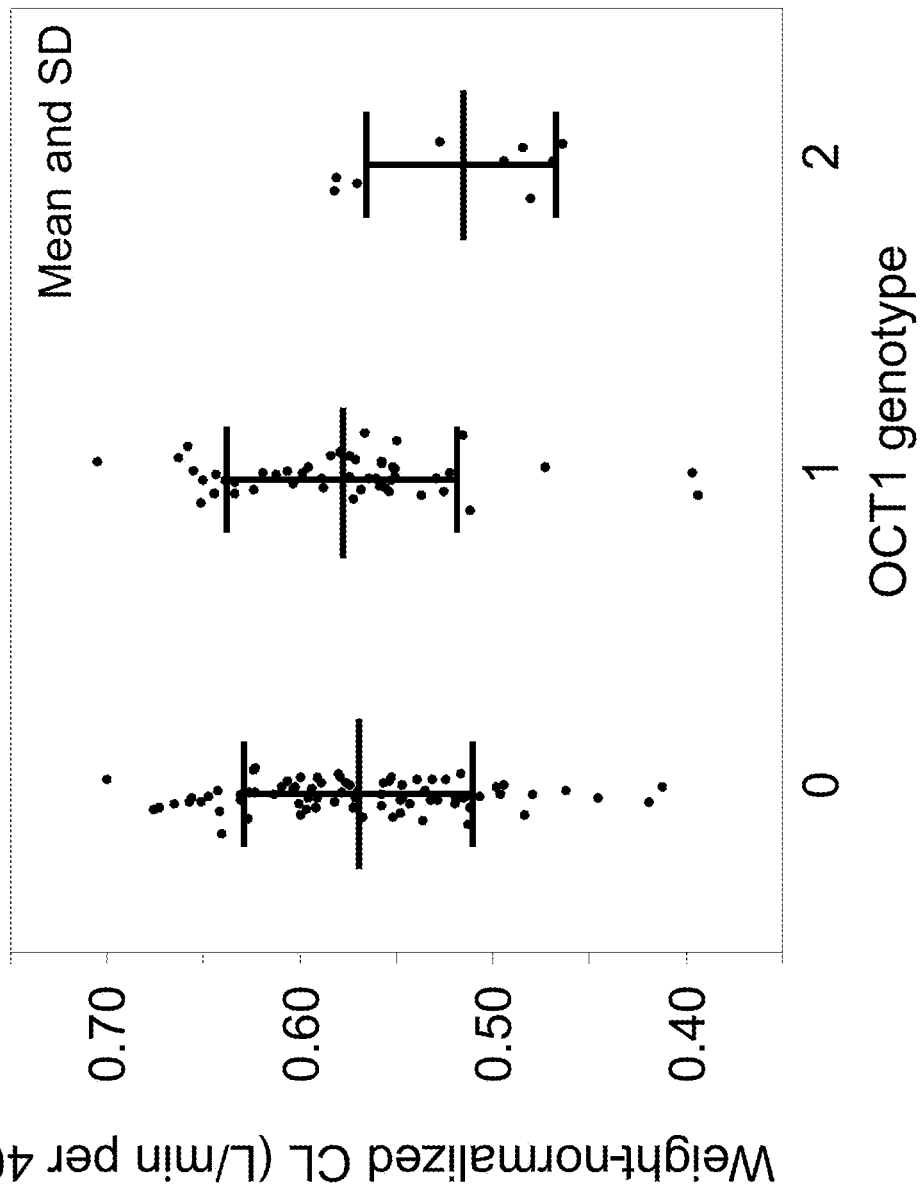
FIG. 14 depicts intravenous weight-normalized morphine clearance for OCT1 genotypes.

Patients of OCT1 genotypes #0, #1, and #2, as defined above, were then analyzed for their ability to pharmacokinetically clear morphine. Weight-normalized morphine clearance was found to be significantly lower for patients homozygous for the defective allele (Group 2) had significantly lowered morphine clearance relative to patients heterozygous for the defective allele (Group 1) and patients without any defective alleles (Group 0) (FIG. 13). In addition, intravenous morphine clearance was also found to be lower with a defective homozygous OCT1 genotype (Group 2) (FIG. 14).

Example 17

Association Between Race and OCT1 Polymorphisms

A study was then conducted to determine the relationship between race and OCT1 SNPs/haplotypes. The haplotypes for Caucasians and African-Americans were first determined, as shown in Table 11. The frequency of defective OCT alleles was found to be lower (0.13) in African-Americans than in Caucasians (0.27), as shown in Table 12.

TABLE 12

| Caucasian | | | | African American | | |
| --- | --- | --- | --- | --- | --- | --- |
| Allele | Number | Frequency | | Allele | Number | Frequency |
| *1 | 157 | 0.727 | 0.727 | *1 | 47 | 0.87 | 0.87 |
| *2 | 30 | 0.139 | | *2 | 4 | 0.074 |
| *3 | 13 | 0.06 | | *3 | 2 | 0.037 |
| *4 | 10 | 0.046 | | *5 | 1 | 0.019 | 0.13 |
| *5 | 6 | 0.028 | 0.273 | Total | 54 | 1 |
| Total | 216 | 1 | | | | |

Example 18

Association Between Race, OCT1 Polymorphisms, and Observed Morphine Clearance

Figures 15A, 15B:
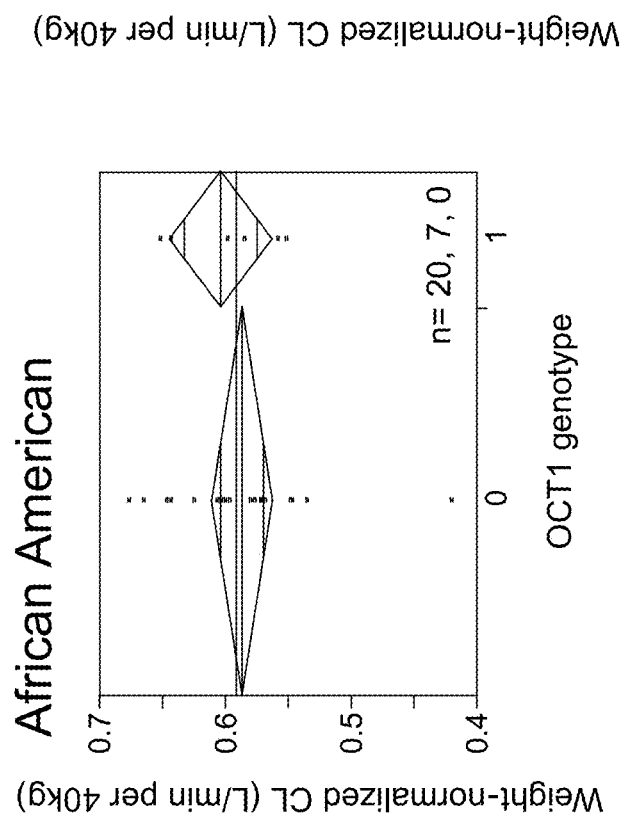
FIGS. 15A-15B depict the race difference in allele frequency and weight-normalized morphine clearance of OCT1 genotypes for African-Americans (15A) and Caucasians (15B).

African-Americans were observed to have higher overall morphine clearance than that in Caucasian patients (FIGS. 15A-B). This can be explained by the race difference in the allele frequency. There were no African-American patients homozygous for the defective allele in this study; therefore, the frequency of the defective OCT allele is low in the African-American population.

In Caucasians, patients homozygous for the defective allele (Group 2) had a significantly lower clearance than patients heterozygous for the defective allele (Group 1) and patients without any defective alleles (Group 0). The Caucasian patient distribution is shown in Table 13.

OCT1 geneotypes were therefore found to be associated with race (Caucasians and African-Americans. Higher morphine clearance was observed in African-Americans than Caucasians) based on underlying specific OCT1 SNPs and haplotypes.

The defective homozygous OCT1 genotype was found to be more frequent in Caucasians than African-American patients, partly explaining the higher observed opioid-related adverse effects in Caucasians with lower morphine clearance and the inadequate pain control in African-Americans with higher morphine clearance.

TABLE 11

| All | | | Caucasians | | | African American | | | Others | |
| --- | --- | --- | --- | --- | --- | --- | --- | --- | --- | --- |
| Haplotype | Number | Group | Haplotype | Number | Group | Haplotype | Number | Group | Haplotype | Number |
| *1/*1 | 80 | #0 (80, 57.1%) | *1/*1 | 58 | #0 (58, 53.7%) | *1/*1 | 20 | #0 (20, 74.1%) | *1/*1 | 2 |
| *1/*2 | 26 | | *1/*2 | 20 | | *1/*2 | 4 | | *1/*2 | 2 |
| *1/*3 | 12 | | *1/*3 | 10 | | *1/*3 | 2 | | *1/*5 | 1 |
| *1/*4 | 6 | | *1/*4 | 6 | | *1/*5 | 1 | #1 (7, 25.9%) | | |
| *1/*5 | 7 | #1 (51, 36.4%) | *1/*5 | 5 | #1 (41, 38.0%) | Total | 27 | | | |
| *2/*2 | 2 | | *2/*2 | 2 | | | | | | |
| *2/*3 | 3 | | *2/*3 | 3 | | | | | | |
| *2/*4 | 2 | | *2/*4 | 2 | | | | | | |
| *2/*5 | 1 | | *2/*5 | 1 | | | | | | |
| *4/*4 | 1 | #2 (9, 6.4%) | *4/*4 | 1 | #2 (9, 8.3%) | | | | | |
| Total | 140 | | Total | 108 | | | | | | |

TABLE 13

| Group | Number | Mean | SD |
|---|---|---|---|
| 0 | 58 | 0.565 | 0.061 |
| 1 | 41 | 0.574 | 0.062 |
| 2 | 9 | 0.517* | 0.049 |

*P < 0.05 vs groups 0 and 1 (non-parametric)

Example 19

Association Between Morphine Clearance, OCT1 Genotype, and Weight

Figure 16:
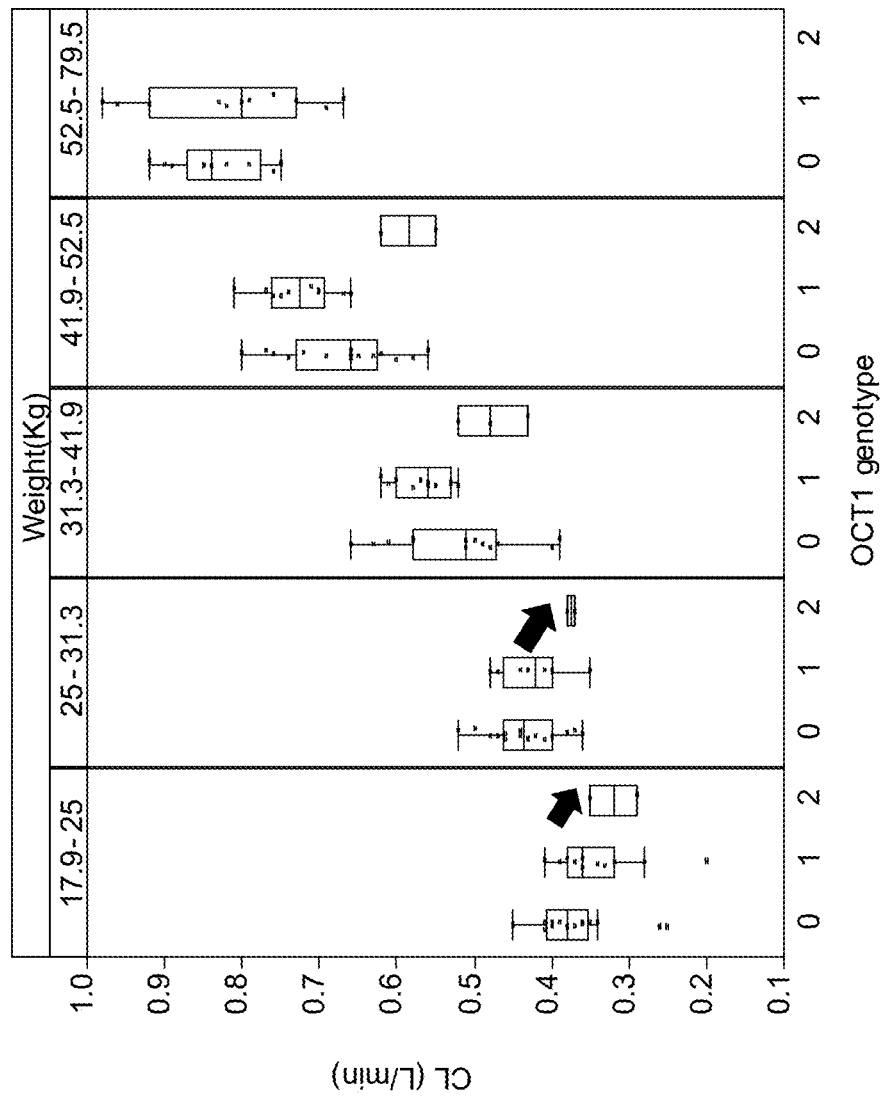
FIG. 16 depicts morphine clearance for OCT1 genotypes in different weight groups.
Figure 17:
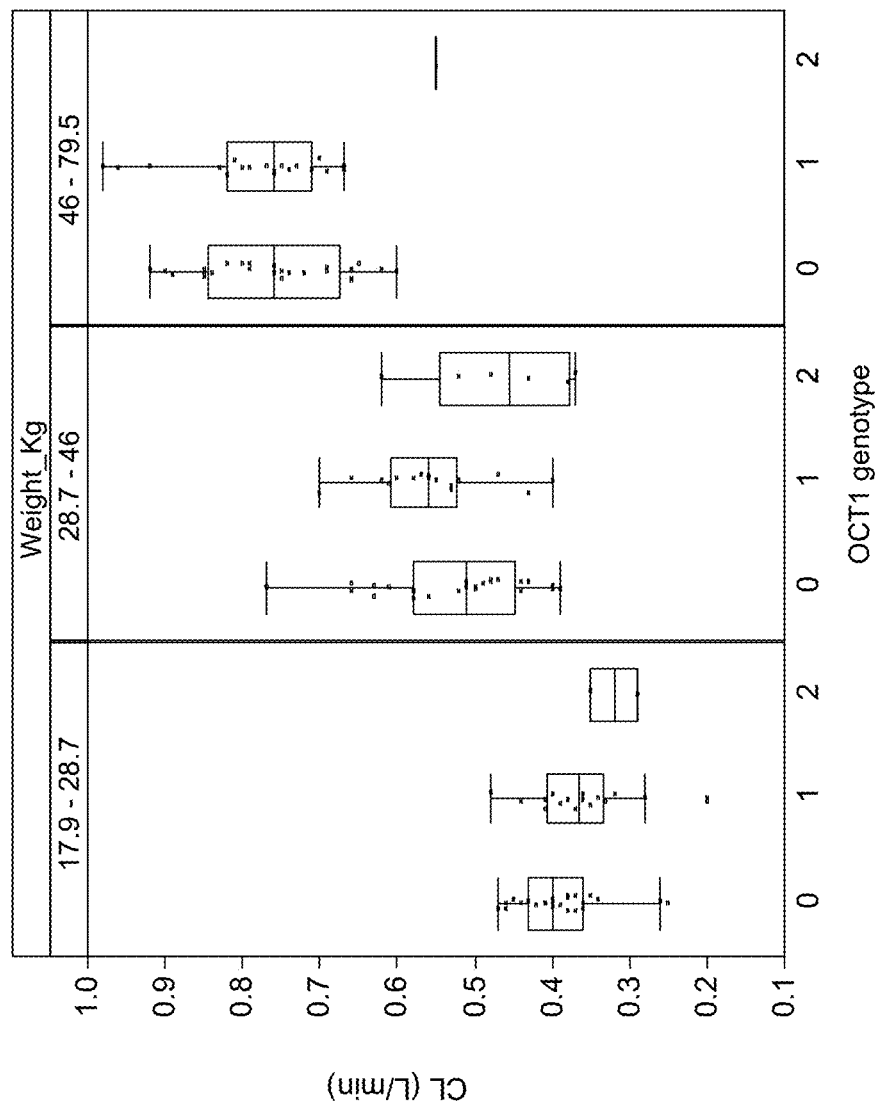
FIG. 17 depicts morphine clearance with defective homozygous OCT1 genotypes.

The morphine clearance of patients with lower weight, who are typically younger, is dependent on the number of defective alleles in the patient, as shown by arrows on FIG. 16. Decreased morphine clearance in patients homozygous for the defective allele (Group 2) was also observed. In addition, morphine clearance was lower for patients with defective homozygous OCT1 genotypes (FIG. 17).

Example 20

Figure 19:
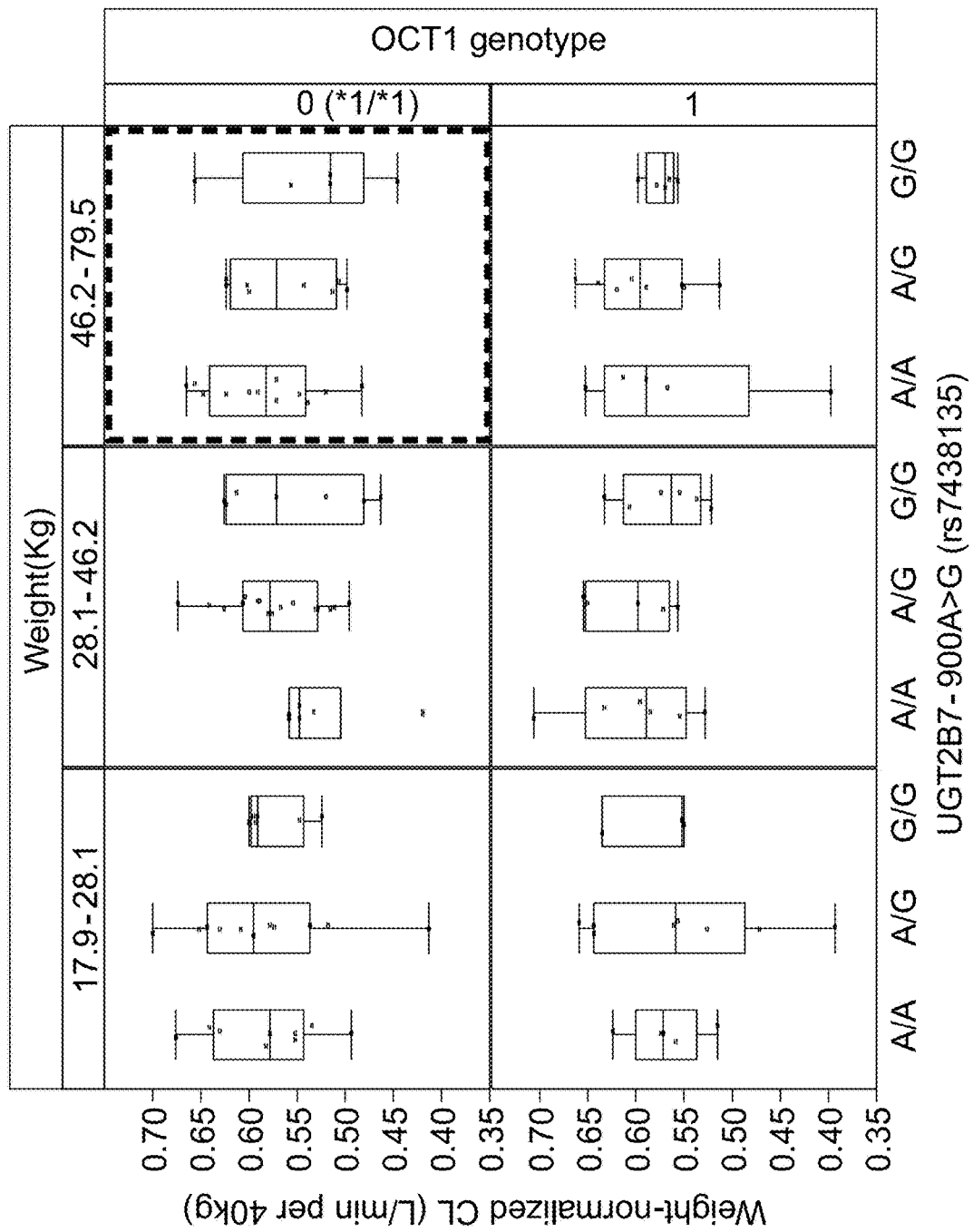
FIG. 19 depicts the weight and age dependency of the UGT2B7 polymorphism contribution.

Specific Polymorphisms Associated with Reduced Morphine Clearance and OCT1 Genotypes A large variability in morphine clearance in patients with *1/*1 (Group 0) can be further explained by the presence of the OCT1 intron rs622342 C allele SNP (FIG. 18). The large variability in morphine clearance in patients with *1/*1 (Group 0) can be further explained by the presence of the UGT2B7 rs7438135 G allele SNP (FIG. 19). This contribution can be dependent on weight and/or age.

Example 21

TRPA1 Genetic Variant Predicts Development of Acute Tolerance to Morphine Analgesia Following Remifentanil Use During Scoliosis Surgery in Adolescents In clinical practice, pharmacological tolerance to opioids results in a diminishing analgesic efficacy during a course of opioid therapy, resulting in escalation of opioid doses in order to restore opioid analgesic effects. Intraoperative infusion of remifentanil is associated with the development of clinically relevant acute opioid tolerance in adolescents undergoing scoliosis surgery (Crawford, et al., *Anesth. Analg.*, 102:1662-7 (2006)). Transient receptor potential cation channel, subfamily A, member 1 (TRPA1) is a polymodal ion channel expressed in nociceptive sensory neurons of the dorsal root ganglia, the activation of which produces pain sensitization and neurogenic inflammation (Bautista, et al., *Cell*, 124:1269-82 (2009)). Accordingly, a study was designed to test the hypothesis that genetic variations of TRPA1 affect development of acute opioid tolerance in adolescents undergoing scoliosis surgery.

A prospective genotype blinded study was conducted in 42 Caucasian adolescents with idiopathic scoliosis who underwent posterior spine fusion, during which they were administered propofol/remifentanil total intravenous anesthesia. All patients received standard morphine patient-controlled analgesia after surgery and were followed for 48 hours postoperatively. Morphine consumption over the first 60 minutes, 60-120 minutes, 2-4 hours, 4-8 hours, 8-16 hours, 16-24 hours, and 24-48 hours, and postoperative pain scores based on a Numerical Rating Scale (NRS) at rest every 8 hours were noted for 48 hours. All patients were genotyped for a TRPA1 variant (rs1025928, C/T). A linear mixed model analysis was employed to test association between pain tolerance (trend of morphine dose) and genotypes. Analysis of variance (ANOVA) analysis was the conducted to compare the genotype sub-groups for remifentanil doses as well as pain scores.

Figure 20:
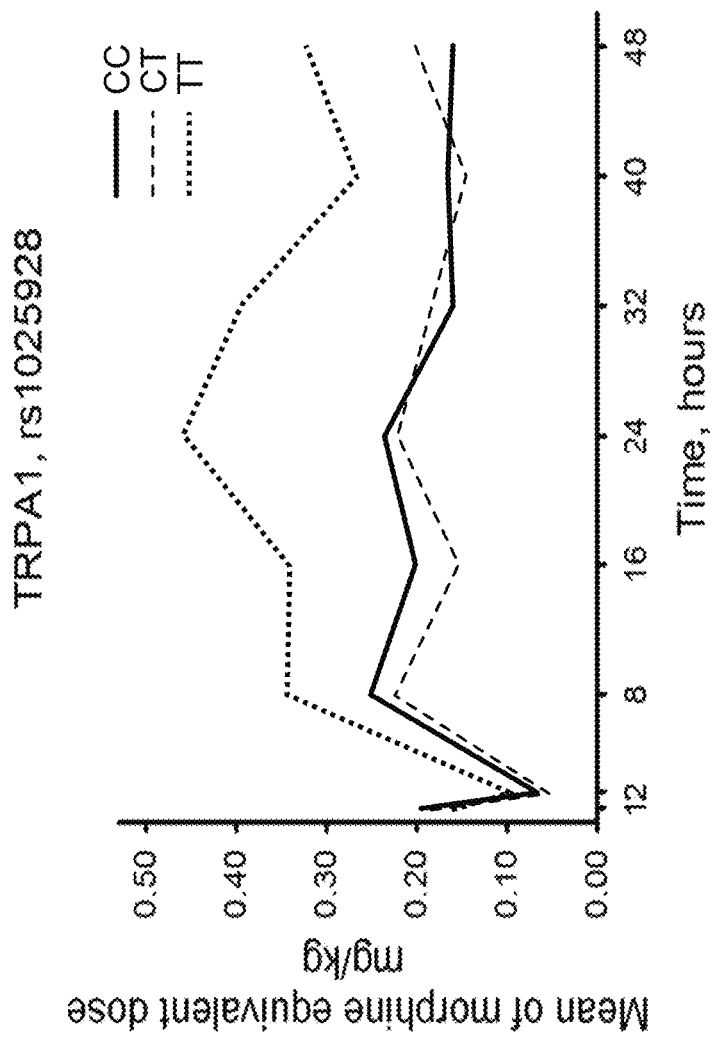
FIG. 20 depicts acute opioid tolerance and the morphine dose requirement trends over 48 postoperative hours by TRPA1 genotype.

A homogeneous group of 42 Caucasian adolescents undergoing posterior spine fusion for idiopathic scoliosis between the ages of 11-19 years, weighing 60.2±16.8 kg, was enrolled. Based on TRPA1 genetic variant, 13 patients were homozygous for wild-type (CC), 23 were heterozygous (CT), and 6 were homozygous (TT) for the risk allele. Remifentanil and propofol doses administered intraoperatively were not significantly different among the three sub-groups (Table 14). Though TT genotype patients had higher postoperative pain scores than the wild type (CC), this difference was not statistically significant (Table 14). The morphine doses in mg/kg over the course of 48 hours for the three genotypes are presented in FIG. 20. The TRPA1 TT genotype for the SNP rs1025928 was found to be associated with time trends of increased morphine requirements in the first 24-48 hours, which suggest development of tolerance to morphine effects in TT genotype patients (p=0.0086).

There is an association between genetic variants of the TRPA1 gene and the development of acute tolerance to morphine's analgesia after spine surgery in healthy Caucasian adolescents. This is remarkable association which can allow for genotype-based personalized opioid dosing and development of drugs targeting these peripheral nociceptors.

TABLE 14

Comparison of propofol, remifentanil doses, and pain scores among the three TRPA1 genotypes.

| TRPA1 Genotype rs 1025928 | N | Intraoperative Total Dose Remifentanil (mcg/kg) Mean ± SD | Intraoperative Total Dose Propofol (mg/kg) Mean ± SD | NRS Pain scores over 48 hours Mean ± S.D. |
|---|---|---|---|---|
| CC | 13 | 1.345 ± 0.363 | 8.815 ± 2.292 | 5.846 ± 3.132 |
| CT | 23 | 1.378 ± 0.535 | 9.377 ± 1.942 | 6.391 ± 2.935 |
| TT | 6 | 1.264 ± 0.425 | 8.981 ± 0.728 | 6.667 ± 1.966 |
| ANOVA, p-value | | 0.871 | 0.694 | 0.807 |

Example 22

Genotype of ABCC3-211C>T Influences the Pharmacokinetics of Morphine Glucuronide in Children Morphine is one of the most commonly used opioids in children to manage perioperative pain. Therefore, identification of mechanisms underlying the inter-individual variability in pharmacokinetics and pharmacodynamics of morphine will be beneficial for developing personalized medicine. Morphine-3-glucuronide (M3G) and morphine-6-glucuronide (M6G), the major active metabolites of morphine, are known to be substrates of MRP3/ABCC3, while the involvement of ABCC3 in the pharmacokinetics of morphine and its glucuronides has heretofore been unclear in humans. Accordingly, a study was designed to examine the influence of a genetic polymorphism in the ABCC3 gene on the pharmacokinetics of morphine glucuronides.

This pharmacogenetic study was conducted as a part of an ongoing morphine study on children undergoing adenotonsillectomy. Concentration-time profiles after the single dose were available from 105 patients for this analysis. All participants were genotyped for ABCC3-211C>T (rs4793665) in order to examine the relationship of this gene with blood concentrations of M3G and M6G.

M3G and M6G concentrations at the sampling time between 10 to 15 minutes were used to evaluate the contribution of the genetic variant. Mean M3G and M6G concentrations were higher in the wild-types (C/C) than children heterozygous and homozygous for the ABCC3-211C>T variant. Twelve out of 105 children had M6G concentrations below the lower quantitative limit, 1 ng/mL, at the sampling window and were all carrying the ABCC3-211C>T variant. Ratios of M3G and M6G to morphine concentrations were significantly lower in patients heterozygous or homozygous for the ABCC3-211C>T variant then the wild-type patients ($P<0.01$ for M3G, $P<0.05$ for M6G).

As these results demonstrate, the ABCC3-211C>T polymorphism influences the pharmacokinetics of M3G and M6G in blood. This finding suggests that ABCC3 is an important factor in the pharmacokinetics of morphine glucuronides, and the genetic variant may be associated with inter-individual differences in the response to morphine treatment in children.

Example 23

Development of an "Efficacy" Decision Tree for Post-Operative Analgesic Use

A study was designed in order to identify genetic variants underlying clinical responses to opioids in children in order to improve and personalize postoperative care and pain management in children. A subset of 199 patients undergoing tonsillectomy, of which 39 were African-American and 99 were classified as suffering from OSA, was analyzed to identify potential patterns of gene-gene interactions and other factors predictive of inadequate pain relief or pain sensitivity, as represented by the need for post-operative analgesic (PA) use. By contrast, the low pain sensitivity class was defined by no need for post-operative intervention in the form of additional analgesic. A standardized site study protocol allowed for unambiguous assignment and accurate quantification of the observed phenotypes.

Genotype data was collected using a specialized SNP panel. The candidate genes were chosen based on their allele frequencies and clinical evidence of important associations in adults with opioid analgesic and adverse effects.

Preliminary statistical analyses revealed several significant associations between genetic as well as non-genetic factors and postoperative opioid adverse effects and inadequate analgesia. In particular, the TT genotype of the ABCB1 SNP rs1045642 was found (after adjusting for OSA) to be associated with a higher risk of morphine-induced respiratory depression. Specifically, in the ABCB1 TT genotype, resting minute ventilation (MV) after morphine decreased by 47.5% compared to only 18.4% in the CC and CT genotypes. Even after 5% $CO_2$ challenge, resting MV after morphine decreased by 29% compared to 10% in the CC and CT genotypes (p=0.05). In addition, a number of other, relatively weak associations with SNPs in FAAH, COMT, and other genes were found, as well as an indication of the epistatic interactions between, for example, the ABCB1 and FAAH SNPs. More systematic multivariate analysis of associations between combinations of multiple SNPs and the respective outcomes will further elucidate these relationships.

Standard CART and C4.5 decision trees, as implemented in R and Weka, respectively, were used to identify and analyze potential patterns of gene-gene interactions and other factors predictive of inadequate pain relief or pain sensitivity (represented by the need for the post-operative analgesic (PA) use). This analysis is summarized as an "efficacy" tree (FIG. 21) for the classification of patients requiring PA use vs. no intervention (noi), using SNP data and covariates such as race and OSA. Leaves (nodes) of the tree that represent strata with increased risk of inadequate pain relief and those with relatively lower risk are indicated on the efficacy decision tree (with the number of patients in each of the two classes in each node shown explicitly).

Figure 21:
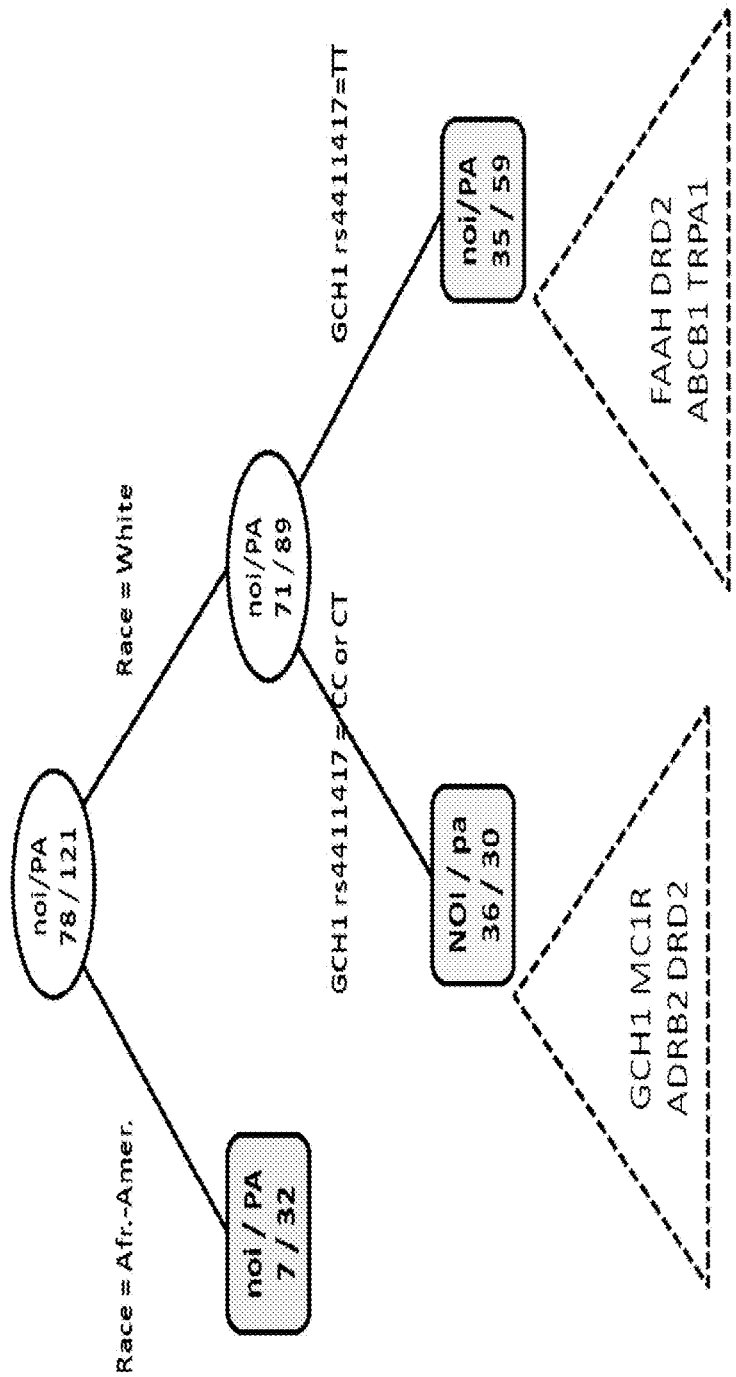
FIG. 21 depicts an "efficacy" decision tree for the postoperative analgesic (PA) use vs. no intervention (noi) classification, using SNP data and covariates such as race. Leaves (nodes) of the tree that represent strata with increased risk of inadequate pain relief and those with relatively lower risk are indicated on the figure; the number of patients in each of the two classes in each node is shown explicitly.

Consistent with known associations between African-Americans, OSA, and higher pain sensitivity, race was found to be the most discriminating feature, splitting the overall cohort of 199 patients into two branches. Among white children, further strata are defined by specific polymorphisms in GCH1 (which was implicated as potential modifier of pain sensitivity and persistence) and interactions involving ABCD1/MC1R, ADRB2, and DRD2, or FAAH, DRD2, ABCD1/MC1R, and TRPA1, in the two main sub-branches; these are shown in FIG. 21 as dotted triangles.

The top part of the efficacy tree can be represented by a simple decision rule as follows:
IF(Race=African-American) THEN high risk of pain sensitivity and inadequate pain relief;
ELSE IF((Race=White) AND (GCH1 rs441417=TT)) THEN moderate risk of pain sensitivity and inadequate pain relief
ELSE IF((Race=White) AND (GCH1 rs441417=CC OR CT)) THEN low risk of pain sensitivity and inadequate pain relief.

Thus, the structure of the tree and the resulting rules that can be used for point of care decision support systems indicate that race alone is a strong predictor of pain sensitivity (82% of African-American children requiring additional post-operative analgesic (PA)), whereas white Caucasian are further stratified by GCH1 and other genes, indicating epistatic effects. However, the C allele of GCH1 is associated with some measure of decreased pain sensitivity, whereas about 63% of homozygous TT genotype white children required additional postoperative analgesic. Further stratification and improved accuracy (with the risk of overfitting being controlled by comprehensive cross-validation and tree stability assessment) can be achieved by taking into account interactions with other genes.

Example 24

Development of a "Safety" Decision Tree for the Prediction of Adverse Effects

Factors predictive of adverse effects were subsequently analyzed to generate a "safety" decision tree (FIG. 22) for the classification of patients with adverse effects, including respiratory depression, nausea and vomiting, and over-sedation (referred jointly to as AE) vs. those with no symptoms of adverse effects (NOS). Leaves corresponding to strata with increased risk of AE are indicated on the safety tree. Only the two main leaves that can be classified most easily by combinations of ABCB1, ADRB2, COMT, and FAAH polymorphisms are shown explicitly within the middle branch.

Consistent with previous univariate analysis, the GG genotype at FAAH rs4141964 SNP was found to be protective. The other two genotypes in interaction with TRPA1 rs1443952 genotypes GG or GA (and specific further interactions with ABCB1, ADRB2, COMT, and FAAH) were found to carry increased risk of adverse effects, including respiratory depression.

Example 25

Development of a Decision Tree to Predict OSA Risk

Figure 23:
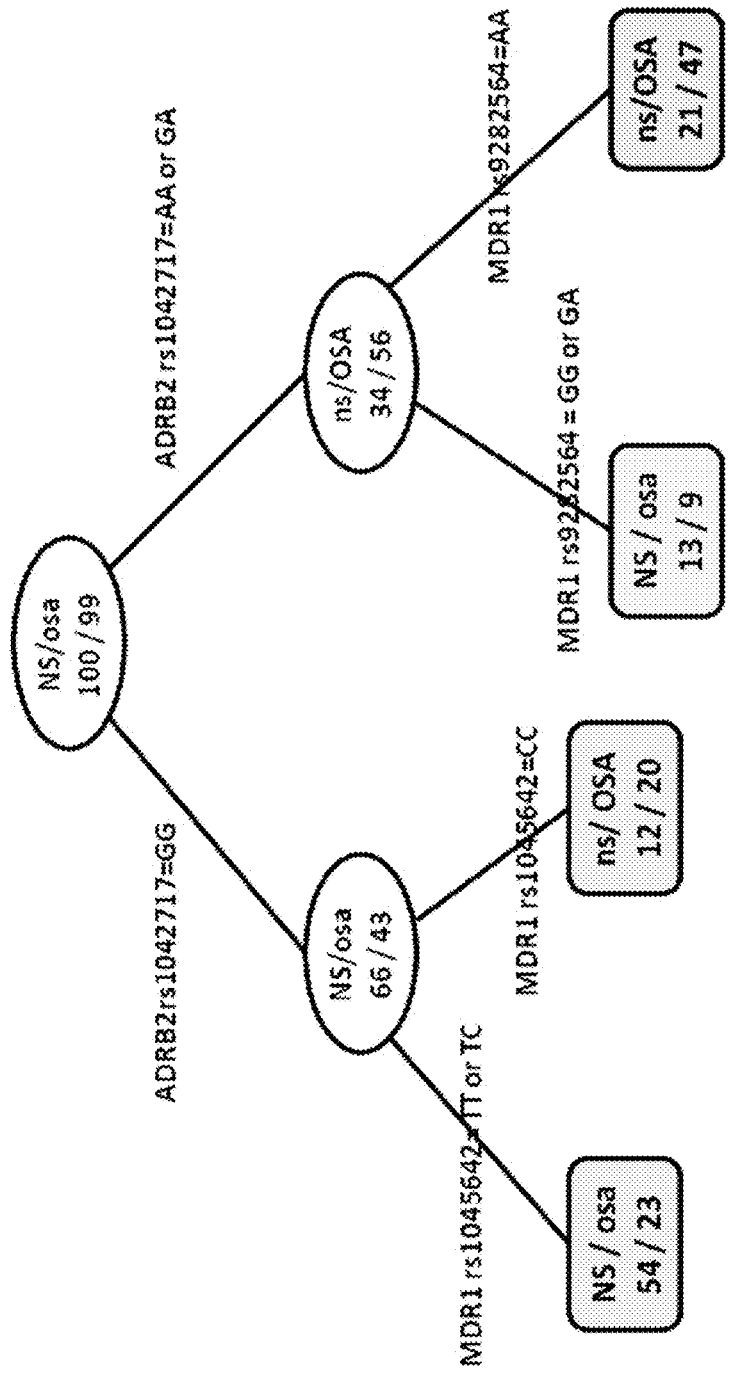
FIG. 23 depicts a decision tree for the ability to predict obstructive sleep apnea (OSA) vs the other classes (NS), using the established panel of SNPs. The OSA tree has about 72% prediction accuracy (with about 50% baseline).

In order to further elucidate potential confounding factors, a decision tree was developed and analyzed for the ability to predict OSA using the established panel of SNPs (FIG. 23). This is aided by the finding that ADRB2 and FAAH gene polymorphisms can be used to relatively accurately predict race.

The interaction of ADRB2, which has been previously implicated in OSA (Larkin, E. et al. *Resp. Crit. Care Med.* 182:947-53 (2010)), with the MDR1 transporter can further help to predict OSA. In particular, the ADRB2 rs1042717 SNP is used, along with MDR1 rs1045642 and MDR1 9282564.

Example 26

Development of a Decision Rule to Predict OSA Risk

A decision rule was developed to express the risk of OSA. This decision rule achieves about 73% classification accuracy (as opposed to about 50% baseline accuracy). The rule is as follows:

IF(((ADRB2 rs1042717=GG) AND (MDR1 rs1045642=CC)) OR ((ADRB2 rs1042717=AA or GA) AND (MDR1 rs9282564=AA))) THEN increased risk of OSA.

The risk is higher in the subset of patients satisfying the ((ADRB2 rs1042717=AA or GA) AND (MDR1 rs9282564=AA)) condition, compared with those patients that fall into the ((ADRB2 rs1042717=GG) AND (MDR1 rs1045642=CC)) branch of the tree. As with previous decision trees, further stratification and improved accuracy (with an increased risk of overfitting) can be achieved by taking into account interactions with other genes.

Example 27

Population Stratification for FAAH Genetic Variations

Figure 22:
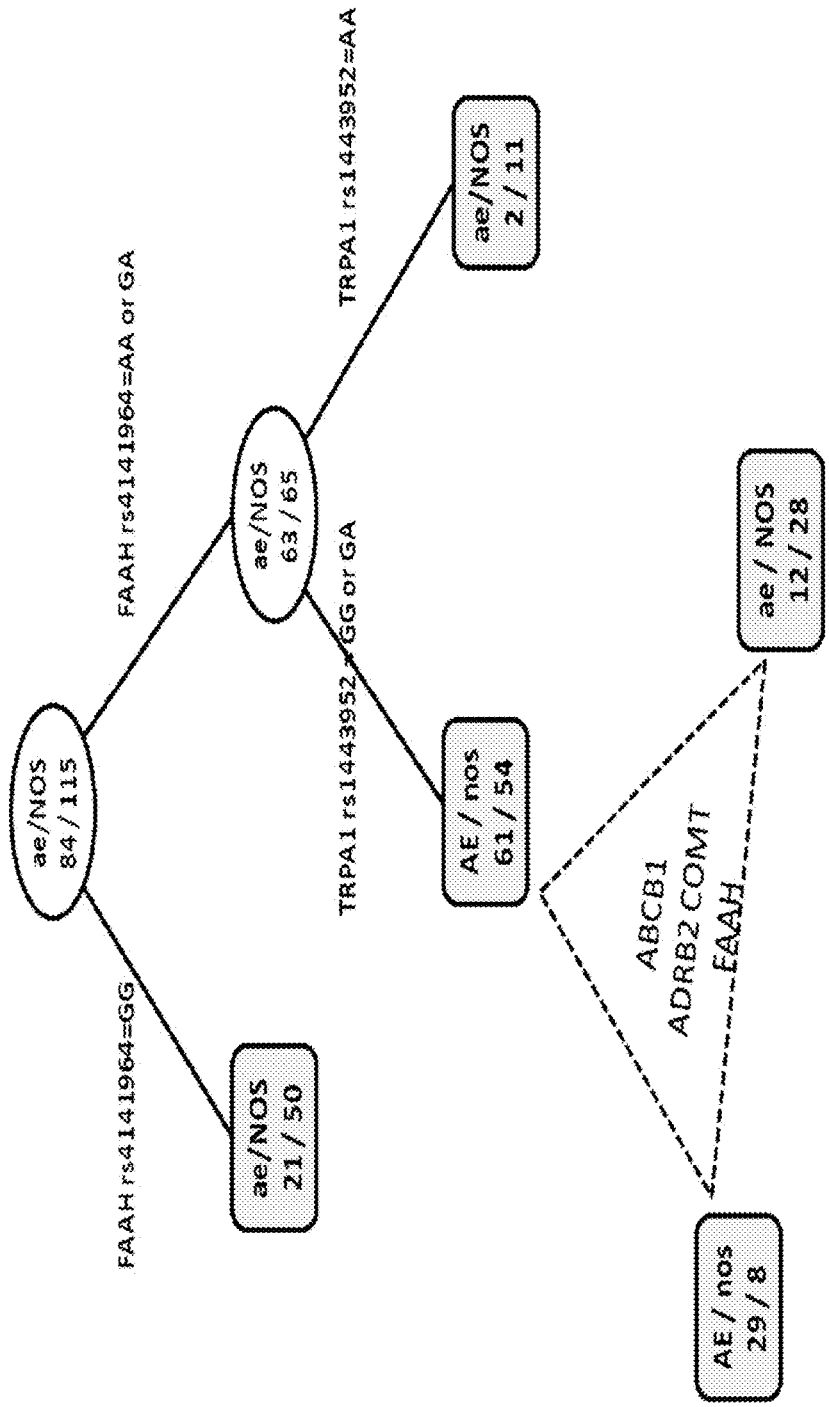
FIG. 22 depicts a "safety" decision tree for the classification of adverse effects (AE) vs. the other classes (NOS). Leaves corresponding to strata with increased risk of AE are indicated on the figure. Only the two main leaves that can be classified most easily by combinations of ABCB1, ADRB2, COMT, and FAAH polymorphisms are shown explicitly within the middle branch.

Population stratification is important for individualizing analgesia. For example, in the results described above, FAAH genetic variations were shown to play a major role in morphine-related adverse effects (FIG. 22).

Figure 24:
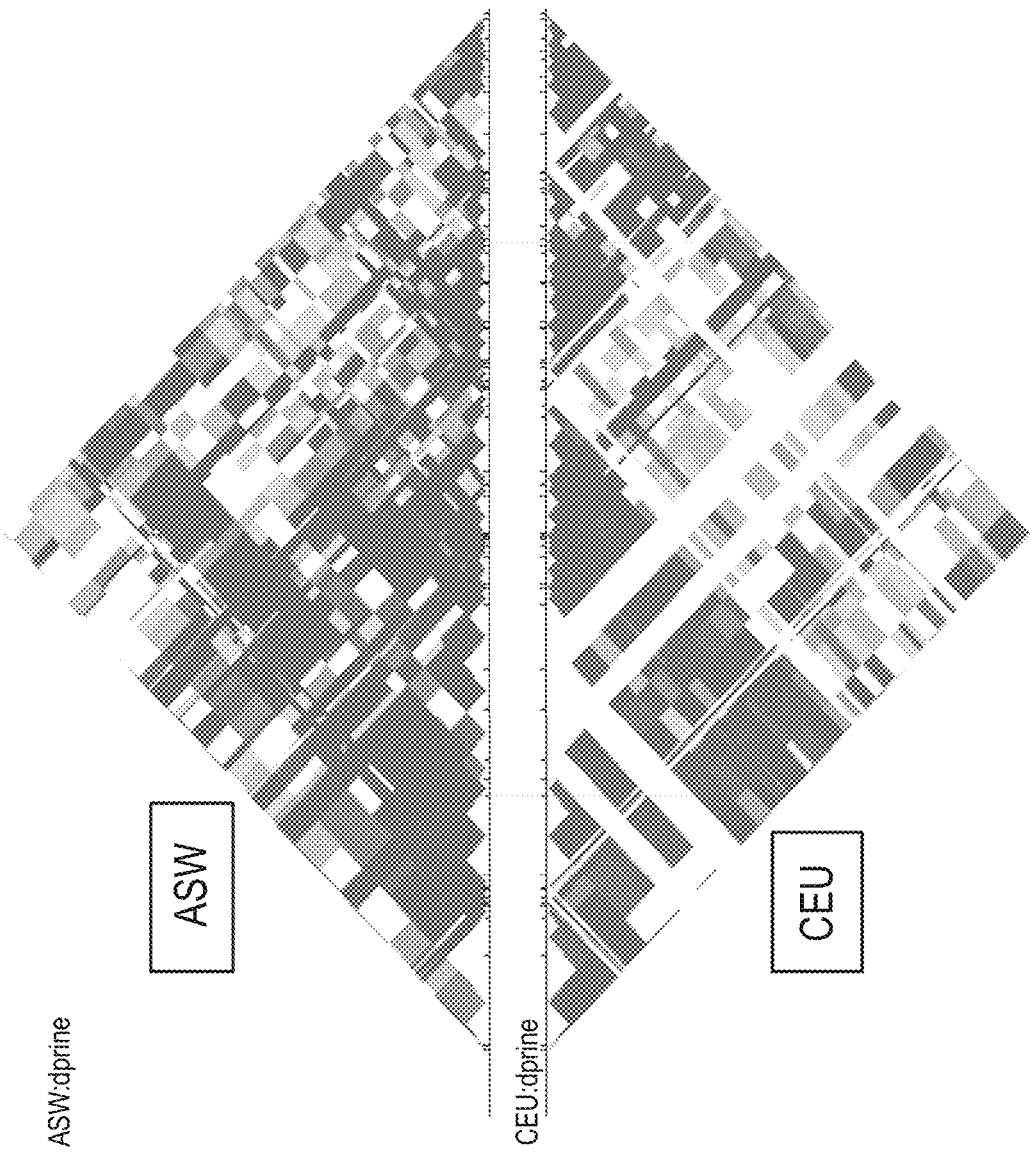
FIG. 24 depicts patterns of linkage disequilibrium (LD) and haplotype blocks around the FAAH gene in Caucasian (CEU) and African ancestry in the southwest US (ASW) HapMap 3 cohorts. Standard D prime measure is used, with dark squares corresponding to high LD (for reference, see <http colon slash slash>www<dot>hapmap<dot>org).

Accordingly, patterns of linkage disequilibrium (LD) and haplotype blocks around the FAAH gene in Caucasian (CEU) and African ancestry were determined in the southwest US (ASW) HapMap 3 cohorts (FIG. 24). Standard D prime measure is used, with dark squares corresponding to high LD (for reference, see <http colon slash slash>www<dot>hapmap<dot>org). As demonstrated in the figure, there are differences in LD patterns in the two common US populations, indicating that there is a need for diverse population and stratification in order to individualize pain and opioid-related adverse effect risk.

Example 28

Codeine-Belated Adverse Effects After Tonsillectomy

Codeine is a widely prescribed opioid analgesic, especially to manage postoperative pain after hospital discharge (Tremlett, M. et al. *Paediatr. Anaesth.* 20:183-94 (2010)), as it is perceived to be as a weaker and safer opioid in children. It is even considered a preferred opioid when airway protection is at risk from over sedation or when neurologic assessment is needed (Semple, D. et al. *Paediatr. Anaesth.* 9:135-8 (1999); Williams, D. et al. *Br. J. Anaesth.* 86:413-21(2001)). However, recent reports of many codeine-related deaths after tonsillectomy in children (Ciszkowski, C. et al. *N Engl. J. Med.* 361:827-8 (2009); Kelly, L. et al. *Pediatrics* 129:e1-5 (2012)), serious adverse drug reactions (ADRs) (Voronov, P. et al. *Paediatr. Anaesth.* 17:684-7 (2007)) and death in breastfed infants whose mothers over-metabolized codeine to morphine (Koren, G. et al. *Lancet* 368:704 (2006); Madadi, P. et al. *Clin. Pharmacol. Ther.* 85:31-5 (2009)) demand re-evaluation of standard clinical practice. Though codeine-related deaths and serious ADRs have been linked to higher than expected conversion of the pro-drug, codeine, to morphine due to cytochrome P450 2D6 (CYP2D6) gene duplications, codeine is commonly used without genetic testing.

Codeine's biotransformation to morphine is reliant on CYP2D6 (Lotsch, J. et al. *Pain* 144:119-24 (2009; Poulsen, L. et al. *Eur. J. Clin. Pharmacol.* 51:298-95 (1996); Sindrup, S. et al. *Clin. Pharmacol. Ther.* 48:686-93 (1990); Yue, Q. et al. *Br. J. Clin. Pharmacol.* 31:635-42 (1991); Kirchheiner, J. et al. *Pharmacogenomics J.* 7:257-65 (2007)). Experimental clinical pain studies have demonstrated reduced analgesia in healthy adults with two nonfunctional CYP2D6 alleles and consequent absent or minimal morphine metabolite concentrations (Poulsen, L. et al. *Eur. J. Clin. Pharmacol.* 51:298-95 (1996); Sindrup, S. et al. *Clin. Pharmacol. Ther.* 48:686-93 (1990); Eckhardt, K. et al. *Pain* 76:27-33 (1998)). Small clinical studies with brief data measurement periods or patients with variable sources of post-operative pain or both have not replicated the analgesic association (Poulsen, L. et al. *Eur. J. Clin. Pharmacol.* 54:451-4 (1998); Williams, D. et al. *Br. J. Anaesth.* 89:839-45 (2002)).

A study was designed to prospectively determine factors associated with codeine's analgesic and adverse effects in a large homogenous population of children undergoing outpatient tonsillectomy. In particular, the study aimed to determine the importance of the CYP2D6 genotype in patient variability in codeine response.

In a prospective, genotype blinded, clinical observation study, 249 healthy children 6-15 years old who had tonsillectomies were enrolled. Codeine-related analgesic and adverse outcome measures were analyzed in 116 white children. The primary outcome was frequency of daily codeine related adverse drug reactions (ADRs). Sedation and pain reduction up to 1 hour following a dose of codeine were secondary measures. Parents recorded their children's daily ADRs, pre- and post-prescribed opioid pain scores, and level of sedation during postoperative days (POD) 0-3 in the home following tonsillectomy alone or with adenoidectomy (T/TA).

Participants

Children scheduled for a T/TA and their parent/legal guardian ("parent") were enrolled. Sample inclusion criteria were children aged 6-15 years, American Society of Anesthesiologists (ASA) physiological status 1 or 2, and scheduled for an elective T/TA. Children who required a T/TA because of obstructive apnea were included. Children were excluded if they or their parents were non-English speaking. Children allergic to study medications, had developmental delay, liver or renal diseases, preoperative pain requiring opioids, or taking prescribed CYP2D6 inhibitors were excluded.

Genotyping and Predicted Phenotype Assignment

Blood was drawn for DNA in the operating room after anesthesia was administered. DNA was isolated on the same day and frozen at −20 degree Celcius. Batched genotyping for a panel of CYP2D6 alleles was performed after clinical data were entered on all study participants CYP2D6 alleles, as defined in the internationally recognized Human Cytochrome P450 (CYP) Database included functional alleles *2, *2A, and *35, reduced function alleles *9, *10, *17, and *41, and nonfunctional alleles*3, *4, *5, *6, *7, *8, *11, *14, *15, *18, *19, *20, *40, *42, and *44. When these variants were not identified, *1 was assumed. The TaqMan allelic discrimination system (Applied Biosystems, Forest City, Calif.) was used to analyze all alleles except CYP2D6*5 allele (full gene deletion) and CYP2D6 duplication, which were detected by long-PCR (Lovlie, R. et al. *FEBS Lett.* 392:30-34 (1996)).

Predicted codeine metabolism phenotypes were designated by a total activity score (TAS) (Crews, K. et al. *Clin. Pharmacol. Ther.* 91:321-6 (2012); Gaedigk, A. et al. *Clin. Pharmacol. Ther.* 83:234-42 (2008)). The TAS was calculated by adding the two allele scores assigned in the following manner: 0 (zero) to a non-functional CYP2D6 allele, 0.5 to a reduced function allele, and 1.0 to a fully functional allele. A diplotype of functional alleles plus duplication were given an additional score of 1.0, resulting in a TAS of 3.0. Children with duplications who were heterozygous for the CYP2D6 fully functional allele and a reduced function or null function allele were excluded because the duplicated allele was indeterminate.

Home-Based Procedures

Home pain medication (opioid+acetaminophen in liquid form) was prescribed by the treating surgeon. Routine post-operative care instructions were given to parents by PACU nurses. Parents were taught by study personnel how to use the home data collection instruments, namely the 0-100 visual analog scale (VAS) portion of The Oucher22 to assess pain intensity, the 0-4 University of Michigan Sedation Scale (UMSS) (Malviya, S. et al. *Br. J. Anaesth.* 88:241-5 (2002)), and a previously-tested, investigator-developed paper diary.

Parents assessed their child's throat pain intensity after swallowing on POD 0 during the afternoon or evening; the morning and afternoon or evening of PODs 1 and 2 and the morning of POD 3. After the pain measure, the prescribed opioid can be administered per the parent's discretion. Post-opioid sedation and pain intensity was recorded 45-60 minutes after opioid administration. At the end of each day, parents recorded ADRs (dizziness or light-headedness; nausea; dry mouth; blurry vision; itching; or rash), the number of emesis, and the number of prescribed opioid doses given. Parents returned the completed diary in a pre-addressed, postage paid business return envelope on POD 3. No incentives for participation or return of completed tools were provided.

Data Analysis

Participants prescribed an opioid other than codeine or who only received acetaminophen for pain during POD 0-3 were excluded. Participants were included in the analyses for ADR and sedation if ADR portion of the diary was completed for at least one day in which codeine was administered. Children with at least 1 paired pain scores before and after a codeine dose were included for pain reduction analyses.

Prior to analyses, data were examined for outliers followed by confirmation with medical records and diaries. Demographic data were summarized as median and interquartile range (IQR) for age and as proportions for sex, race, ASA physical status, and CYP2D6-predicted TAS. To determine if there were significant differences between enrolled participants and those retained for the codeine pharmacogenetics analyses, chi-square tests were used to compare categorical variables, and t-tests were used to compare continuous variables.

The association of CYP2D6 TAS with ADR, sedation, and pain was tested. The primary outcome was the sum of daily ADR events, including dizziness, stomach sickness, vomiting (yes/no), dry mouth, itching, blurry vision, rash, and other. To reduce misclassification, a binary sedation outcome was generated by dichotomizing UMSS scores: awake (scores 0-1) or asleep (scores 2-4). To account for intra- and inter-individual variability, the number of daily ADRs and pain scores were examined with linear mixed-effects models; sedation was examined with a generalized linear mixed model. Independent variables, including codeine, age, sex, race, POD, and time of day were tested and included when significant. Covariance structures were evaluated using Bayes information criterion (BIC). Autoregressive, compound symmetry and unstructured covariance structure were selected to model ADR, sedation and pain, respectively. Analyses were performed using Statistical Analysis Software (SAS), version 9.2 (SAS Institute Inc., Cary, N.C.). Significant effects were considered to be present if $p<0.017$ after Bonferroni correction for three tests.

Results

Figure 25:
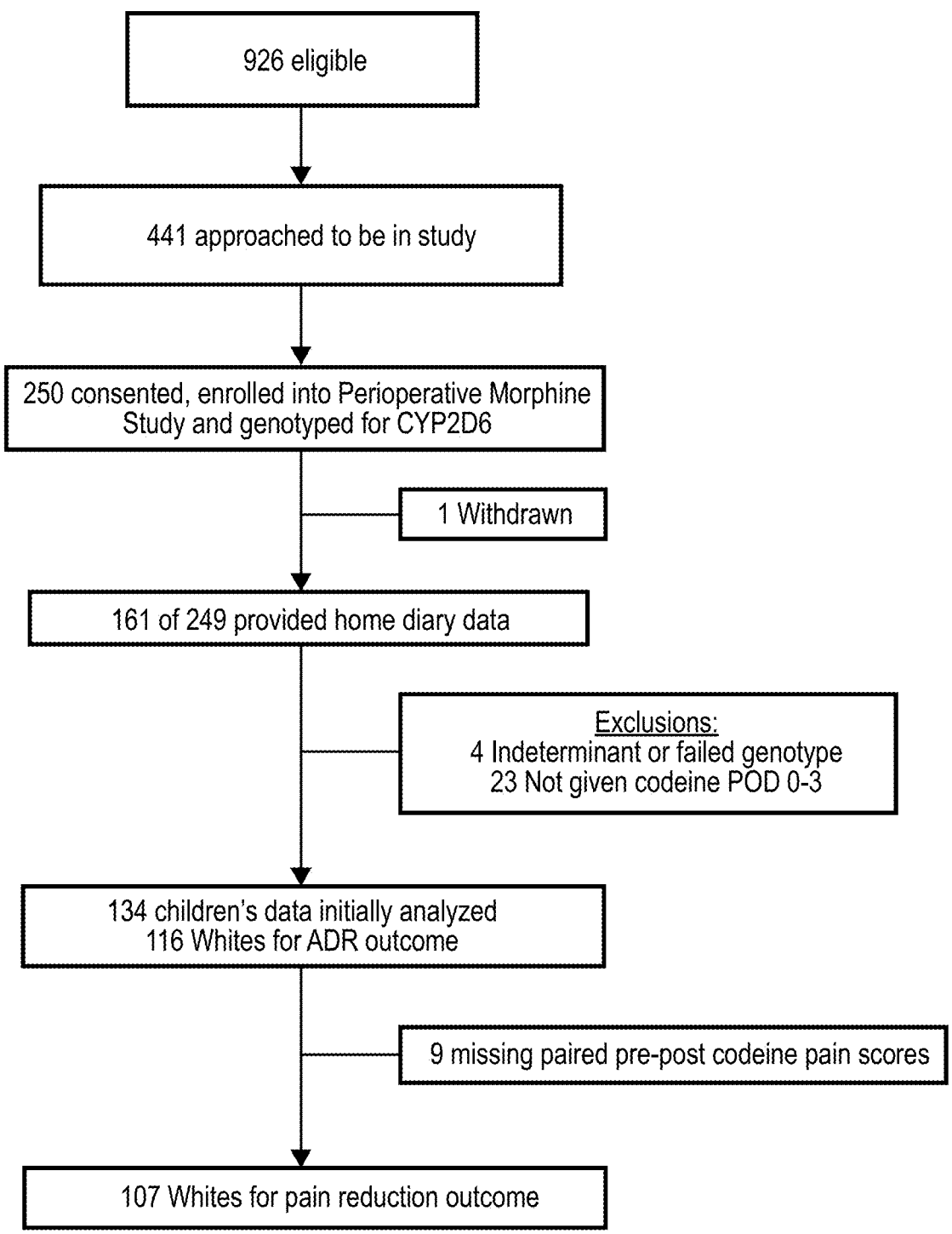
FIG. 25 depicts the patient cohort for the study of codeine adverse drug reactions (ADRs) and analgesic effects.

Diary data were obtained from 161 of the 249 patients (64.66% retention rate); 134 (83.23%) of those with diary data met inclusion criteria (FIG. 25). No significant demographic differences were detected between enrolled and retained children; Table 15 shows the descriptive characteristics of study participants. In the enrolled cohort, the proportion of extreme genotype-predicted phenotypes (TAS>3.0=1.2% and TAS 0.0=10.44%) were consistent with previous reports (Bernard, S. et al. *Oncologist* 11:126-35 (2006); Bradford, L. *Pharmacogenomics* 3:229-43 (2002); Sistonen, J. et al. *Pharmacogenet. Genomics* 17:93-101 (2007)).

Preliminary data review indicated that ADR frequency was highest on POD 0. Intraoperative and PACU administered opioids as well as swallowed blood all can contribute to day of surgery ADRs. Since ondansetron was consistently administered intraoperatively, and ADRs occurring in the hospital were not counted, this day was included in analyses. POD 3 was excluded from analyses after noting a morning codeine dose was not recorded by 45% of children. Finally, because the proportion of non-white children was small (8.96% Black, 4.48% Other) and it has been suggested that pain can be reported, manifested and treated differently between racial and ethnic groups (Sadhasivan, S. et al. *Pediatrics* 129:832-8 (2012); Fortier, M. *Pediatrics* 124: 378-80 (2009)), their ADRs and pain data were not included in the outcome analyses. This remaining cohort's median daily doses of codeine were: two, POD 0; three, POD 1; three, POD 2; one, POD 3. No differences were detected in median daily doses between TAS groups.

and is consistent with the greatest risk period for codeine-related adverse effects.

While reliance on parents' documentation of children's pain before and after a dose of codeine can limit data reliability due to potential reporter bias, these ADR results are consistent with other clinical studies. There was no potential bias that could explain differences in pain intensities by CYP2D6 TAS, since genotyping was done after all clinical data were collected.

TABLE 15

|  | Perioperative Cohort (N = 249) | Codeine/Acetaminophen Cohort (N = 134) | p-value |
|---|---|---|---|
| Age | Median (IQR) 8.47 (7.12-11.07) | Median (IQR) 8.41 (7.07-11.06) | |
|  | Number (percent) | | |
| Gender | | | 0.90 |
| Female | 134 (53.82%) | 73 (54.48%) | |
| Male | 115 (46.18%) | 61 (45.52%) | |
| Race | | | 0.10 |
| White | 199 (79.92%) | 116 (86.57%) | |
| Non-white | 50 (20.08%) | 18 (13.43%) | 0.49 |
| ASA 1 | 132 (53.01%) | 76 (56.72%) | |
| ASA 2 | 117 (46.99%) | 58 (43.28%) | |
| CYP2D6 predicted phenotype: TAS | | | 0.57 |
| 0.0 | 26 (10.44) | 15 (11.19) | |
| 0.5 | 12 (4.82) | 8 (5.97) | |
| 1.0 (0.5 + 0.5) | 73 (29.32) | 35 (26.12) | |
| 1.0 | 11 (4.42) | 7 (5.22) | |
| 1.5 | 44 (17.67) | 21 (15.67) | |
| 2.0 | 73 (29.32) | 45 (33.58) | |
| >3.0 | 3 (1.20) | 3 (2.24) | |
| Indeterminate duplication | 6 (2.41) | 0 | |
| Failed genotype | 1 (0.40) | 0 | |

Primary Outcome: Codeine-Related ADR

Figure 26:
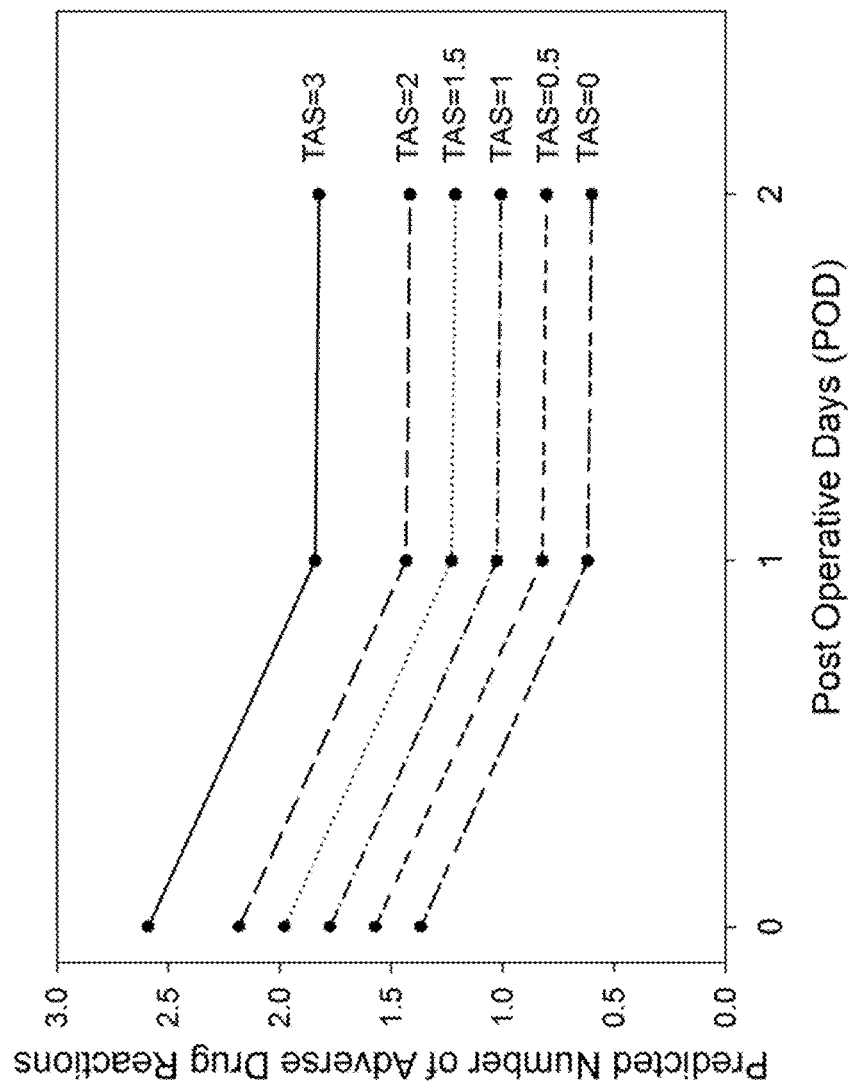
FIG. 26 depicts the CYP2D6 total activity score (TAS) association with the predicted number of ADRs.

After adjusting for daily codeine doses, the number of ADRs on POD 0 were significantly higher than POD 1 and POD 2 (p<0.0001), while the difference for POD 1-2 was not significant (p=0.92). During POD 0-2, the number of ADRs was associated with TAS of CYP2D6 (p=0.004). With every one point increase in TAS, the predicted number of ADRs increased by 0.41 (FIG. 26). ADR frequency was not associated with age or sex.

Figure 27A:
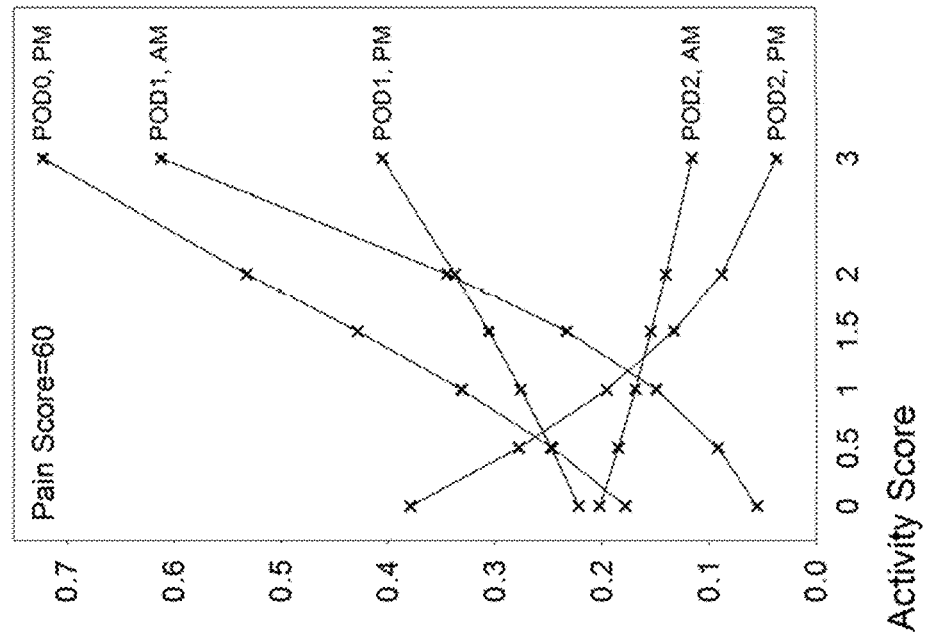
FIGS. 27A-27B depict the factors contributing to the probability of sedation after codeine administration.
Figure 27B:
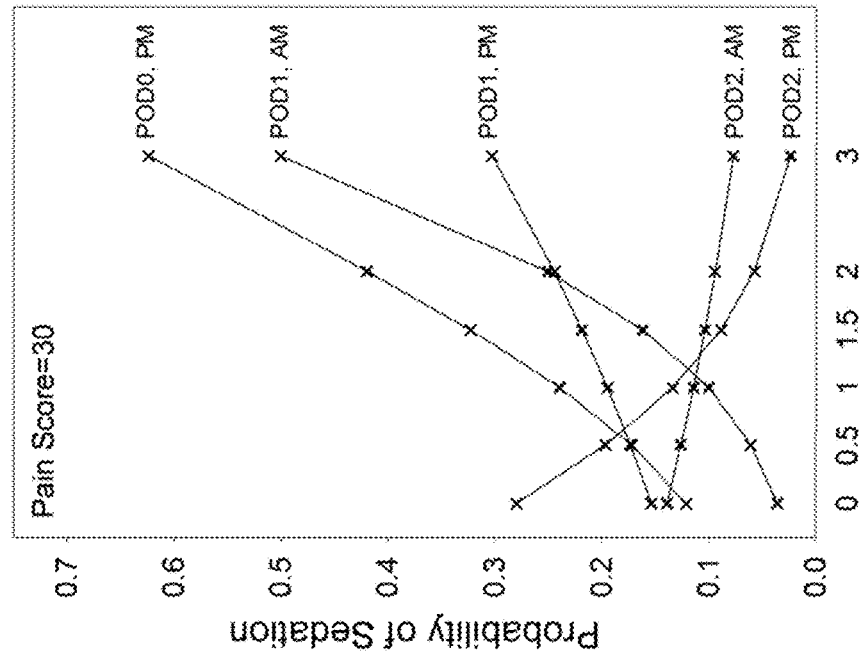

Several independent variables contributed to sedation variability (FIG. 27). During POD 0-2, females were more likely to be sedated (p=0.05), and the probability of sedation increased as pain scores increased (p=0.003). Sedation was also influenced by an interaction between TAS and time (p=0.003), wherein the probability of sedation after a dose of codeine increased as TAS increased during the evening of POD 0 and the morning of POD 1. However, this trend was reversed by POD 2. No significant age effect was detected.

Heretofore, sedation measures after home-administered codeine have not been available. By asking parents to wait 45-60 minutes after codeine administration to measure sedation, the confidence was increased in establishing that codeine was at least one factor related to sedation. Pain intensity prior to codeine (p=0.003) was found to be a consistent strong predictor for sedation, but the directional relationship of TAS and sedation varied by time. The probability of sedation after a dose of codeine increased with TAS score on the day of surgery and the morning of POD 1

Example 29

Codeine-Related Pain Reduction After Tonsillectomy

In the same study, the effect of administration of codeine on the secondary outcome of pain management was evaluated.

Secondary Outcome: Pain Reduction

Pre- and post-codeine pain intensities varied by time (p=0.0006). Codeine reduced pain intensity by an average of 28 points (SE 2) during POD 0-2 (p<0.0001).

Figure 28A:
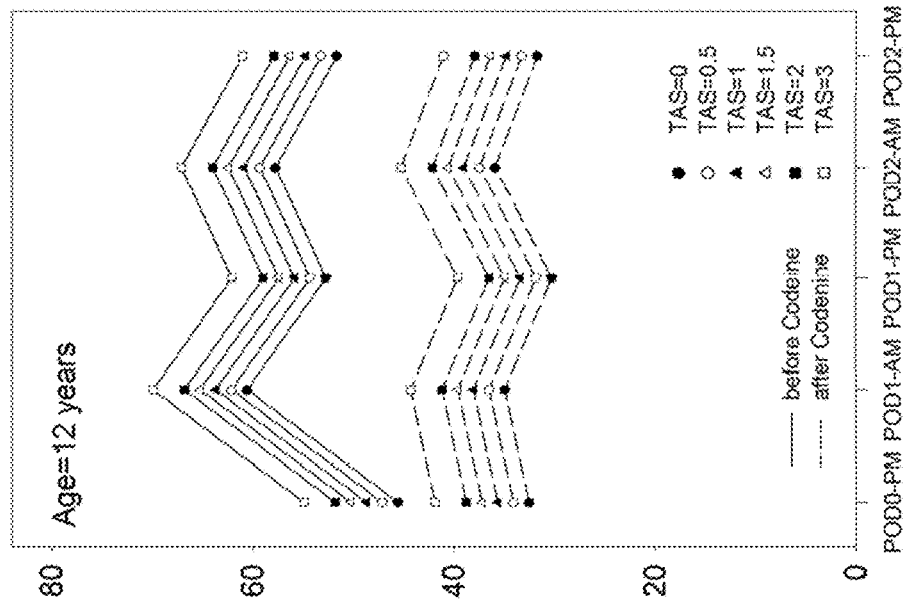
FIGS. 28A-28B depict the factors contributing to pain intensity before and after codeine administration in 7 year olds (28A) and in 12 year olds (28B).
Figure 28B:
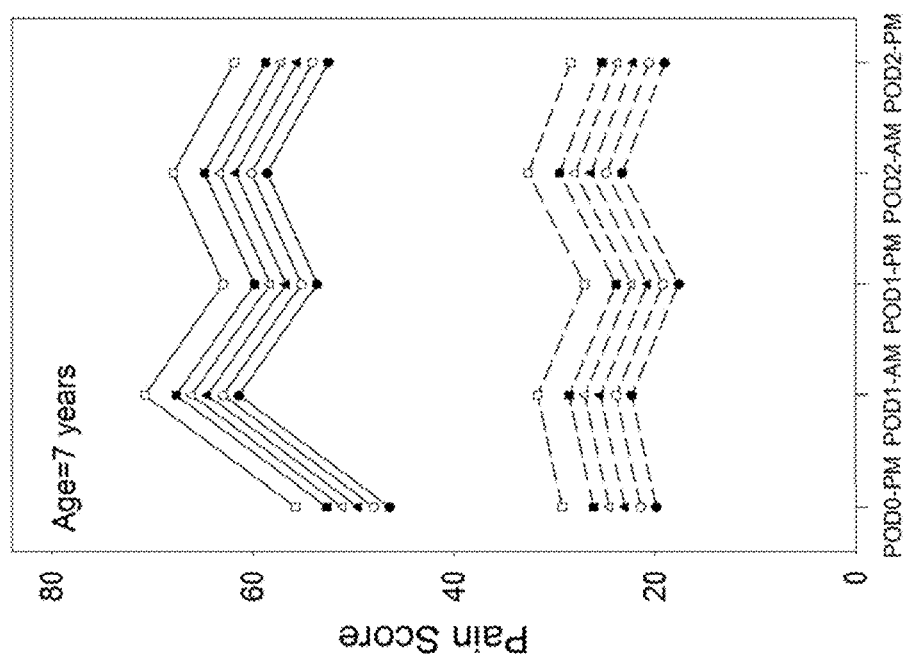

Pain reduction was also influenced by age and time. Younger children reported more pain reduction (p=0.0002). In addition, pain reduction on POD 0 was significantly less (p=0.0012). Significant association of TAS with pain intensities and pain reduction were not identified (FIG. 28).

Restricting analysis to POD 1-2, TAS continued to not be associated with pain reduction but approached significant association with pain intensity prior to codeine (p=0.05). A one unit increase in TAS predicted a five-point increase in pain score. When dichotomizing and comparing the functional group (TAS 2.0+3.0) with the nonfunctional group (TAS 0.0+0.05), the functional group had a predicted 10-point higher pain score (p=0.02).

Example 30

Increasing CYP2D6 TAS Association with Increasing Pain Intensity

CYP2D6 was not associated with pain reduction following codeine administration. This is similar to previous studies with small patient samples sizes, variable pain models and short hospital evaluation periods (Poulsen, L. et al. *Eur. J. Clin. Pharmacol.* 54:451-4 (1998); Williams, D. et al. *Br. J. Anaesth.* 89:839-45 (2002); Persson, K. et al. Br. J. Clin. Pharmacol. 39:182-6 (1995)). A more recent study of women administered codeine following cesarean section did show expected responses: the two patients with TAS=0 reported no analgesia while two patients with TAS>3 reported significant pain relief but discontinued codeine due to ADRs (Vandervaart, S. et al. *Ther. Drug. Monit.* 33:425-32 (2011)).

The Clinical Pharmacogenetics Implementation Consortium (CPIC) recently recommended avoiding codeine use in ultrarapid metabolizers, i.e. those with total activity score (TAS)>3 due to increased morphine formation and higher risk for toxicity (Crews, K. et al. *Clin. Pharmacol. Ther.* 91:321-6 (2012)). CPIC also recommended avoiding codeine in poor metabolizers due to greatly reduced morphine formation and insufficient pain relief. Yet, CYP2D6 testing is rarely done in clinical settings for prescribing decisions regarding medications for pain management. The findings described herein support CPIC recommendation for children with CYP2D6 TAS>3. These findings, in addition to other clinical studies (Poulsen, L. et al. *Eur. J. Clin. Pharmacol.* 54:451-4 (1998); Williams, D. et al. *Br. J. Anaesth.* 89:839-45 (2002); Persson, K. et al. Br. J. Clin. Pharmacol. 39:182-6 (1995)), do not support that CYP2D6 activity alone moderates patient reported pain relief.

Two previous studies (Poulsen, L. et al. *Eur. J. Clin. Pharmacol.* 51:298-95 (1996); Kirchheiner, J. et al. *Pharmacogenomics J.* 7:257-65 (2007)) support an association between the CYP2D6 phenotype and codeine ADRs, including sedation. Case reports of children's deaths when taking codeine following tonsillectomy alone or with adenoidectomy (T/TA) accentuate the clinical importance of considering CYP2D6 TAS as well as other factors, such as respiratory illness (Ciszkowski, C. et al. *N. Engl. J. Med.* 361: 827-8 (2009)) or obstructive sleep apnea as an indication for T/TA (Kelly, L. et al. *Pediatrics* 129:e1-5 (2012)) when prescribing codeine for pain management. Recent guidelines specifically recommend avoidance of codeine in CYP2D6 ultra rapid metabolizers (UMs, TAS>3) (Crews, K. et al. *Clin. Pharmacol. Ther.* 91:321-6 (2012); Swen, J. et al. *Clin. Pharmacol. Ther.* 83:781-7 (2008)).

Codeine, a weak opioid, can be considered a surrogate for more potent opioids that also are metabolized by CYP2D6; such as hydrocodone, oxycodone and tramadol, whose active metabolites have more than 10-fold mu opioid receptor binding capacities than morphine (Smith, H. *Clin. J. Pain* 27:824-38 (2011)). CPIC guidelines specifically recommend avoiding tramadol as well as codeine in CYP2D6 UMs (Crews, K. et al. *Clin. Pharmacol. Ther.* 91:321-6 (2012)) and the guidelines from the Netherlands recommend avoidance of oxycodone and tramadol as well as codeine in CYP2D6 UMs (Swen, J. et al. *Clin. Pharmacol. Ther.* 83:781-7 (2008)).

Heretofore, sedation measures after home administered codeine have not been reported. Sedation is an early warning sign before opioid-related respiratory depression. By asking parents to wait 45-60 minutes after codeine administration to measure sedation, the confidence that codeine was at least one factor related to sedation was increased. This is in contrast to the study that asked parents about overall daily sedation (Sutters, K. et al. *Pain Manag. Nurs.* 6:49-57 (2005)). As described herein, pain intensity prior to codeine (p=0.003) was found to be a consistent strong predictor for sedation, but the directional relationship of TAS and sedation varied by time. The probability of sedation after a dose of codeine increased with TAS score on day of surgery and the morning of POD 1 and is consistent with the greatest risk period for ADRs.

Decrease in predicted daily ADRs and sedation following codeine is not unexpected, as parents typically do not give maximum allowable daily doses of prescribed opioids (Sutters, K. et al. *Pain Manag. Nurs.* 6:49-57 (2005); Sutlers, K. et al. *J. Pediatr. Nurs.* 12:178-85 (1997); Sutlers, K. et al. *Clin. J. Pain* 26:95-103 (2010); Bean-Lijewski, J. et al. *Otolaryngol. Head Neck Surg.* 137:545-51 (2007); Howard, R. *JAMA* 290:2464-9 (2003)), do not adjust opioid frequency based on pain intensity (Fortier, M. et al. *Pediatrics* 124:e588-95 (2009)) and tend to reduce the number of daily doses over the post-operative period (Sutlers, K. et al. *Pain Manag. Nurs.* 6:49-57 (2005); Sutters, K. et al. *Clin. J. Pain* 26:95-103 (2010)).

Therefore, the sensitivity of TAS as a predictor for ADRs and sedation may decrease over time due to low codeine and morphine concentrations. Around-the-clock codeine (ATC) administration expected to achieve more consistent therapeutic concentrations can increase daily ADRs over time in patients who over metabolize codeine to morphine. Twice as many children receiving ATC compared with PRN codeine administration following T/TA were withdrawn from a study due to intolerable side effects (17.4% versus 6.7%) (Sutters, K. et al. *Pain Manag. Nurs.* 6:49-57 (2005)); however, CYP2D6 influence on ADR frequency was not considered.

The reversal in TAS relationship with sedation following codeine is complex. However, central effects of codeine in poor metabolizers have been reported with codeine-6-glucuronide, suggesting the active moeity (Lotsch, J. et al. *Clin. Pharmacol. Ther.* 79:35-48 (2006)). The sedative effect of codeine-6-glucuronide when codeine is repeatedly dosed needs further investigation.

The limited evidence of CYP2D6 association with codeine's analgesic property in clinical studies contrasts the often cited experimental pain studies in healthy adults whose pain threshold (Sindrup, S. et al. *Clin. Pharmacol. Ther.* 48:686-93 (1990)) and tolerance (Poulsen, L. et al. *Eur. J. Clin. Pharmacol.* 51:298-95 (1996); Eckhardt, K. et al. *Pain* 76:27-33 (1998)) to painful stimuli after codeine significantly varied between extensive metabolizers (EM=at least one full functioning CYP2D6 allele) and poor metabolizers (PMs=TAS 0.0). Pain detection and pain tolerance for brief periods of time is a necessary surrogate since inducing sustained pain for experimental purposes would be unethical. Yet, the results described herein and those of others indicate that experimental pain tolerance and clinical pain reduction studies are not necessarily comparable. Recommendations to avoid codeine in CYP2D6 PMs are based on the results in experimental pain studies (Crews, K. et al. *Clin. Pharmacol. Ther.* 91:321-6 (2012); Swen, J. et al. *Clin. Pharmacol. Ther.* 83:781-7 (2008); Galinkin, J. *AAP News* Sep. 1, 2011). Although hydrocodone or oxycodone in their parent forms can have analgesic properties, they cannot be safely recommended alternatives to codeine without also recommending CYP2D6 testing to assure these medications are not inadvertently prescribed to children with TAS>3.

The findings described herein of the increasing CYP2D6 TAS association with increasing pain intensity deserve further investigation. Supportive evidence can be found in prior studies. Using Sindrup et al.'s reported data (Sindrup, S. et al. *Clin. Pharmacol. Ther.* 48:686-93 (1990)), the EM's mean time for tolerating electrical stimulus was 0.56 compared to 0.67 in PMs (p=0.02) prior to codeine and when given placebo. A similar trend was found in Poulsen et al.'s reported median pain detection and tolerance (Poulsen, L. et al. *Eur. J. Clin. Pharmacol.* 51:289-95 (1996)) when CYP2D6 EMs and PM were given placebo. The two women who were CYP2D6 PMs had less pain intensity post-cesarean section, but investigators hypothesized this was due to older age (Vandervaart, S. et al. *Ther. Drug Monit* 33:425-32 (2011)).

Example 31

Pharmacogenomics Research Network (PGRN) Sequencing Platform (PGRN-SEQ)

The PharmacoGenomics Research Network (PGRN) is a national genomic research network (see www<dot>pgrn<dot>org). PGRN has selected a few important genes and developed a genetic sequencing platform known as PGRN-Seq.

The PGRN-Seq panel targets common and rare sequence variations in 84 "very important phamacogenes" associated with drug response; these genes are listed in Table 16. This panel encompasses three different types of genes, namely drug targets, those involved in drug transport, and those that impact drug metabolism. The genes selected were well-validated and were additionally associated with commonly prescribed drugs.

TABLE 16

Genes on the PGRN-Seq Platform

ABCA1
ABCB1
ABCB11
ABCC2
ABCG1
ABCG2
ACE
ADRB1
ADRB2
AHR
ALOX5
APOA1
ARID5B
BDNF
CACNA1C
CACNA1S
CACNB2
CES1
CES2
COMT
CRHR1
CYP1A2
CYP2A6
CYP2B6
CYP2C19
CYP2C9
CYP2D6
CYP2R1
CYP3A4
CYP3A5
DBH
DPYD
DRD1
DRD2

TABLE 16-continued

Genes on the PGRN-Seq Platform

EGFR
ESR1
FKBP5
G6PD
GLCCI1
GRK4
GRK5
HLA-B
HLA-DQB3
HMGCR
HSD11B2
HTR1A
HTR2A
KCNH2
LDLR
MAOA
NAT2
NPPB
NPR1
NR3C1
NR3C2
NTRK2
PEAR1
POR
PTGIS
PTGS1
RYR1
RYR2
SCN5A
SLC15A2
SLC22A1
SLC22A2
SLC22A3
SLC22A6
SLC47A1
SLC47A2
SLC6A3
SLC6A4
SLCO1A2
SLCO1B1
SLCO1B3
SLCO2B1
TBXAS1
TCL1A
TPMT
UGT1A1
UGT1A4
VDR
VKORC1
ZNF423

Using Nimblegen in-solution enrichment technology (Roche, Indianapolis, Ind.) and Illumina sequencing, the PGRN-Seq panel captures all of the exons of the 84 genes, the untranslated regions, and 2 kilobase pairs upstream of the exons. Twenty four samples are multiplexed per sequencing lane, which enables an average coverage per sample of around 500-fold. This high coverage helps to discover rare variants, such as a novel nonsense variant in the Ryanodine 1 Receptor, RYR1 gene. Some rare genetic variants (e.g. RYR1 gene) that are associated with life-threatening anesthesia-related complications, such as malignant hyperthermia, can be identified easily with preemptive genotyping before exposure to anesthesia. Many disruptive mutations have been found in RYR1 in patients with malignant hyperthermia.

The PGRN-Seq panel is used to identify common and rare genomic information predicting patient response to anesthetics, opioid analgesics, pain, and other commonly used perioperative medications. The PGRN-Seq panel is also used to incorporate clinically actionable genomic information with electronic medical records in order to improve patient care.

The PGRN-Seq panel is particularly applicable to the personalized pain and anesthesia research described herein given its targeted approach to genes relevant to drug action, transport, and metabolism. In addition, the PGRN-Seq panel has the most comprehensive coverage of targeted genes by complete sequencing to enable identification common and rare variants influencing outcomes. Such targeted gene sequencing is relatively inexpensive compared to cost-prohibitive whole genome sequencing.

The PGRN-Seq panel is used to identify mechanistic pathways contributing to clinical outcomes, providing insights into selection of appropriate drug among existing drugs and possibly future drug development. The PGRN-Seq panel is also used to contribute standardized genetic data to a federal database for future research.

Example 32

Genome-Wide Association Studies

Advances in commercially available genotyping technology (e.g. by companies such as Affymetrix and Illumina) have facilitated the use of genome-wide association studies (GWAS) to link specific genetic variants with human disease. These studies use allele frequencies in populations under consideration to find correlations between a phenotype (disease status) and individual genomic variants (typically SNPs), as well as CNVs and insertion-deletions (indels) (The International HapMap Consortium, Nature, 426: 789-96 (2003); LaFramboise, T., Nucl. Acids Res., 37:4181-93 (2009); Schaaf, C. et al., Annual Review of Genomics and Human Genetics, 12:25-51 (2011)).

The large scale of the source data and the need for data on very large cohorts (often tens of thousands of individuals) require efficient data management and pose challenges in data analyses. While a number of very efficient and high-quality GWAS analysis software packages are available (e.g. PLINK, SNPTEST, LAMP), the challenge of transparently managing genome-wide variant information in conjunction with demographic and phenotypic variables is difficult with off-the-shelf tools (Purcell, S., et al., Am. J. Hum. Genet., 81:559-75 (2007); Marchini, J., et al., Nature Reviews Genetics, 11:499-511 (2010); Li, M., et al., Am. J. Hum. Genet., 76:934-49 (2005)).

Genotyping data typically involves iterative rounds of filtering and quality control, which usually result in many versions of the same data, which in turn create challenges in documentation and tracking. Accordingly, as described herein, improved processes have been developed for managing large (genome-wide) genotype data sets. In order to provide a central, web-accessible repository for the typically large raw genotyping data (e.g. CEL files for Affymetrix and idat files for Illumina platforms), an application was developed (see <http colon slash slash>research<dot>cchmc<dot>org<slash>genotyping), which allows investigators to perform the following functions: 1) upload new data files that conform to a certain file format, wherein all files are parsed, and any metadata contained in the file is parsed out by the system; 2) control access to data, based on permissions granted by the owner of the data; 3) tag data files with keywords and controlled vocabulary; 4) upload text files or spreadsheets with supplemental information about the primary data; 5) use keyword, controlled vocabulary, and/or free-text searches to retrieve and download primary data; 6) use the interface to launch processing (genotype calling) algorithms on a Linux cluster computer, thus enabling access to very high-performance computing power for basic researchers otherwise unfamiliar with computing tools or languages. In particular, the CRLMM approach to genotype calling (open source software, see <http colon slash slash>www<dot>bioconductor<dot>org<slash> packages<slash slash>2.10<slash>bioc<slash>html<slash>crlmm<dot>html) has been implemented, and the Affy Power Tools are available to users as well.

A second application, called gwadb (Genome-Wide Association Database, see <http colon slash slash>research<dot>cchmc<dot>org<slash>gwadb2), has been developed as well and consists of a user-friendly, web-based interface to a relational database holding all relevant data (in particular, genotype calls) and metadata for GWAS analyses. This application enables clinical and translational researchers to perform GWAS analyses and related tasks on well-curated, well-documented data without requiring knowledge of Linux command lines. This is accomplished by storing raw or minimally processed genotyping data in the same database as basic demographics and phenotypic information. Users can therefore not only download any data in a number of commonly used file formats but also process these data through a number of pre-defined, parameterized workflows which run on a Linux cluster. The capability of executing these complex and often CPU-time and memory-intensive processes as a batch job on a cluster is essential for GWAS-type analyses, as the data sizes often make local processing close to impossible.

Currently, the processing workflows that are directly callable from gwadb's web interface include commonly-used tools, such as PLINK (for quality control, case-control analyses, basic data management, etc.), Eigenstrat (for cohort variability visualization), IMPUTE2 (for imputation of genotypes to the 1000 Genomes reference set), and KING (for automated pedigree imputation based on genotypes) (Price, A., et al., Nat. Genet., 38:904-9 (2006); Manichaikul, A., et al., Bioinformatics, 26:2867-73 (2010)); Howie, B., et al., PLoS Genet., 5:e1000529 (2009)). Each of these tools is essential to perform GWAS studies.

PLINK is widely used in the community and provides a large number of functions to summarize, manage, filter and analyze large-scale SNP data and has become a de facto standard tool in any analysis. Association p-values can be uploaded directly into a track of a local instance of the UCSC Genome Browser and further processed and visualized. The analysis of ancestry with tools such as Eigenstrat is equally essential, not only for cohort stratification but also as a quality control tool since it in effect allows for verification of self-reported ancestries. Imputation is a crucial tool when performing analyses across different genotyping platforms, and, due to its computational cost, it is especially convenient for end-users to run IMPUTE2 on the computational cluster from gwadb. GWAS studies also generally assume that all data used come from unrelated subjects, and KING is a convenient, fast computational tool that can verify kinships and uncover previously unknown familial relationships. This is especially useful when merging different cohorts in order to verify that no one is enrolled in both cohorts at the same time. As new applications and extensions are considered, more software tools can easily be incorporated into gwadb due to its flexible design, modular architecture, and the integration with a Linux computational cluster, which enables parallel large scale computation in the batch mode, as well as on-the-fly analysis whenever applicable.

Gwadb is implemented using open-source tools such as php and mysql. Furthermore, all communication to the server is encrypted with SSL, and strict guidelines are enforced concerning user names and passwords, thus ensuring security and compliance with security standards. These portals represent complete suites that integrate the management of disk-based storage for primary data, the management and integration of metadata about the primary data with clinical data points, as well as the processing of these data using state-of-the-art algorithms and computational equipment in a user-friendly web interface.

The HumanOmni5-Quad (Omni5) BeadChip (Illumina) provides the most comprehensive coverage of the genome, with 4.3 million genetic markers. This platform leverages powerful tag SNPs selected from the International HapMap and 1000 Genomes Projects that target genetic variation down to 1% minor allele frequency (MAF).

Using proven systems and arrays, the Omni5 BeadChip offers high-throughput sample processing and optimized content for whole-genome genotyping and CNV applications. This end-to-end DNA analysis solution includes convenient kit packaging, a streamlined PCR-free protocol, and integrated analysis software.

The Omni5 BeadChip is applied to experimental, analytical, and statistical studies relating to personalized pain and anesthesia. The Omni5 BeadChip has the most comprehensive coverage of the genome and is used for whole-genome screening of currently known and unknown genetic risk factors related to the study outcomes described herein. Because this platform has extensive and diverse ancestry informative markers, the Omni5 BeadChip is used to verify/validate self-reported race, stratify populations and risks of patients with similar genetic background, and identify effects of population admixture on research outcomes.

The Omni5 BeadChip is additionally advantageous given the availability of the extensive control population. Also, GWAS is relatively inexpensive compared to cost-prohibitive whole genome sequencing Specific genetic variants associated with study outcomes are then identified. If the gene is not part of the PGRN-Seq panels (Table 16), the gene is then sequenced to identify the most important genetic variant associated with specific outcomes. In this way, mechanistic pathways contributing to clinical outcomes are identified, providing insights into selection of appropriate therapeutic or alternative among existing therapeutics or alternatives. Future drug development based on the newly-identified mechanistic pathways is also enabled.

Example 33

Prediction of Adverse Effects Upon Clinical Opioid Administration

A patient in need of treatment for pain relief is subject to the sequencing platform and subsequently to the decision models described herein in order to determine the patient's risk or susceptibility to developing adverse effects from administered anesthesia, analgesic, and/or opioid. The results are used to determine whether to administer anesthesia, analgesic, or opioid, as well as to determine anesthesia, analgesic, or opioid selection, as well as to determine an appropriate dosage, as well as to determine potential side effects.

Example 34

Prediction of Adverse Effects Upon Home Opioid Administration

A patient in need of home pain management is subject to the sequencing platform and subsequently to the decision models described herein in order to determine the patient's risk or susceptibility to developing adverse effects from administered analgesic and/or opioid. The results are used to determine whether to administer an analgesic and/or opioid, as well as to determine analgesic and/or opioid selection, as well as to determine an appropriate dosage, as well as to determine potential side effects.

Example 35

Patient Screening for Potential Adverse Effects

The sequencing platform is used pre-emptively in children at increased likelihood of requiring surgery and subsequent pain management. For those children who have been subjected to the sequencing platform, results relating to relevant, clinically validated gene variants important in opioid response will be placed in the children's electronic medical record. If medication is subsequently required, the variants will be incorporated into a decision model for analgesic selection and dosing. The results are used to determine whether to administer an anesthetic, analgesic, and/or opioid, as well as to determine anesthetic, analgesic, and/or opioid selection, as well as to determine an appropriate dosage, as well as to determine potential side effects.

The various methods and techniques described above provide a number of ways to carry out the application. It is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features, and steps discussed above, as well as other known equivalents for each such element, feature, or step, can be employed in various combinations by one of ordinary skill in this art to perform methods in accordance with the principles described herein. Among the various elements, features, and steps, some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters are to be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that can have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for treating a human patient for post-operative pain, the method comprising the steps of
    a) obtaining a biological sample from a patient in need of treatment for post-operative pain, wherein the biological sample is obtained prior to administering an opioid analgesic to the patient;
    b) genotyping the biological sample from the patient to determine the patient's genotype at a single nucleotide polymorphism (SNP) of the ATP binding cassette C3 (ABCC3) gene identified by rs4793665, wherein the genotyping is performed using one or more of a PCR-based technique for nucleic acid amplification from the sample, gel electrophoresis, mass spectrometry, and microarray hybridization;
    c) identifying the presence of a T allele at ABCC3 rs4793665 in the biological sample; and
    d) administering an analgesic selected from fentanyl, hydromorphone, codeine, oxycodone, hydrocodone, tramadol, ondansetron, dexamethasone, methadone, alfentanil, remifentanil, acetaminophen, a non-steroidal anti-inflammatory drug (NSAID), dexmedetomidine, clonidine, and combinations and derivatives thereof for post-operative pain to the patient having the allele identified in step c).

2. The method of claim 1, wherein the patient is a pediatric patient.

3. The method of claim 1, wherein the analgesic is selected from the group consisting of acetaminophen, a non-steroidal anti-inflammatory drug (NSAID), dexmedetomidine, clonidine, and combinations and derivations thereof.

4. The method of claim 1, further comprising receiving at least one non-genetic risk factor selected from the patient's race, sex, and obstructive sleep apnea disease status.

5. The method of claim 4, wherein the non-genetic risk factor is race and the race is selected from Caucasian and African American.

6. The method of claim 5, wherein the race is Caucasian.

7. The method of claim 4, wherein the non-genetic risk factor is obstructive sleep apnea disease status.

* * * * *